US012600970B2

(12) United States Patent
Bennett et al.

(10) Patent No.: US 12,600,970 B2
(45) Date of Patent: Apr. 14, 2026

(54) COMPOSITIONS FOR MODULATING C9ORF72 EXPRESSION

(71) Applicant: Ionis Pharmaceuticals, Inc., Carlsbad, CA (US)

(72) Inventors: C. Frank Bennett, Carlsbad, CA (US); Susan M. Freier, San Diego, CA (US); Frank Rigo, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/330,084

(22) Filed: Jun. 6, 2023

(65) Prior Publication Data

US 2024/0200067 A1 Jun. 20, 2024

Related U.S. Application Data

(63) Continuation of application No. 16/546,283, filed on Aug. 20, 2019, now abandoned, which is a continuation of application No. 14/436,024, filed as application No. PCT/US2013/065073 on Oct. 15, 2013, now Pat. No. 10,443,052.

(60) Provisional application No. 61/714,132, filed on Oct. 15, 2012.

(51) Int. Cl.
*C12N 15/113* (2010.01)

(52) U.S. Cl.
CPC ........ *C12N 15/113* (2013.01); *C12N 2310/11* (2013.01); *C12N 2310/313* (2013.01); *C12N 2310/315* (2013.01); *C12N 2310/322* (2013.01); *C12N 2310/3233* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,801,154 | A | 9/1998 | Baracchini et al. |
| 5,998,148 | A | 12/1999 | Bennett et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 7,759,478 | B1 | 7/2010 | Bentwich et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| 8,927,513 | B2 | 1/2015 | Manoharan et al. |
| 9,012,421 | B2 | 4/2015 | Migawa et al. |
| 9,605,263 | B2 | 3/2017 | Rigo |
| 9,896,729 | B2 | 2/2018 | Pickering-Brown et al. |
| 9,963,699 | B2 | 5/2018 | Bennett et al. |
| 10,066,288 | B2 | 9/2018 | Hsiao |
| 10,138,482 | B2 | 11/2018 | Rigo |
| 10,221,414 | B2 | 3/2019 | Freier et al. |
| 10,443,052 | B2 | 10/2019 | Freier |
| 10,577,604 | B2 | 3/2020 | Bennett et al. |
| 10,815,483 | B2 | 10/2020 | Rigo |
| 2001/0053519 | A1 | 12/2001 | Fodor et al. |
| 2003/0228597 | A1 | 12/2003 | Cowsert et al. |
| 2004/0038274 | A1 | 2/2004 | Cook et al. |
| 2004/0171570 | A1 | 9/2004 | Allerson et al. |
| 2004/0181048 | A1 | 9/2004 | Wang |
| 2005/0130923 | A1 | 6/2005 | Bhat et al. |
| 2005/0255487 | A1 | 11/2005 | Khvorova et al. |
| 2006/0003322 | A1 | 1/2006 | Bentwich et al. |
| 2006/0270623 | A1 | 11/2006 | McSwiggen |
| 2007/0031844 | A1 | 2/2007 | Khvorova et al. |
| 2008/0039618 | A1 | 2/2008 | Allerson et al. |

(Continued)

FOREIGN PATENT DOCUMENTS

| | | |
|---|---|---|
| EP | 1752536 | 2/2007 |
| WO | WO 1996/014329 | 5/1996 |

(Continued)

OTHER PUBLICATIONS

Extended EP Search Report for 22197003.1 dated Jun. 30, 2023, 19 pages.

(Continued)

*Primary Examiner* — Sean McGarry
(74) *Attorney, Agent, or Firm* — McNeill PLLC

(57) ABSTRACT

Disclosed herein are compositions and methods for reducing expression of C9ORF72 mRNA and protein in an animal with C9ORF72 specific inhibitors. Such methods are useful to treat, prevent, or ameliorate neurodegenerative diseases in an individual in need thereof. Such C9ORF72 specific inhibitors include antisense compounds. Examples of neurodegenerative diseases that can be treated, prevented, and ameliorated with the administration C9ORF72 specific inhibitors include amyotrophic lateral sclerosis (ALS), frontotemporal dementia (FTD), corticalbasal degeneration syndrome (CBD), atypical Parkinsonian syndrome, and olivopontocerellar degeneration (OPCD).

24 Claims, No Drawings

Specification includes a Sequence Listing.

(56) References Cited

U.S. PATENT DOCUMENTS

| | | | |
|---|---|---|---|
| 2009/0012281 | A1 | 1/2009 | Swayze et al. |
| 2010/0216864 | A1 | 8/2010 | Staarup et al. |
| 2012/0149757 | A1 | 6/2012 | Krainer et al. |
| 2012/0214865 | A1 | 8/2012 | Bennett et al. |
| 2013/0035366 | A1 | 2/2013 | Swayze et al. |
| 2014/0255936 | A1 | 9/2014 | Rademakers |
| 2014/0303238 | A1 | 10/2014 | Linsley et al. |
| 2015/0148404 | A1 | 5/2015 | de Visser |
| 2015/0259679 | A1 | 9/2015 | Bennett et al. |
| 2015/0267197 | A1 | 9/2015 | Bennett et al. |
| 2016/0024496 | A1 | 1/2016 | Bennett et al. |
| 2016/0108396 | A1 | 4/2016 | Jensen et al. |
| 2016/0251655 | A1 | 9/2016 | Freier et al. |
| 2016/0304871 | A1 | 10/2016 | Rigo |
| 2017/0349897 | A1 | 12/2017 | Rigo |
| 2018/0318330 | A1 | 11/2018 | Prakash et al. |
| 2019/0264204 | A1 | 8/2019 | Rigo |
| 2019/0367916 | A1 | 12/2019 | Freier et al. |
| 2021/0230589 | A1 | 7/2021 | Rigo |

FOREIGN PATENT DOCUMENTS

| | | |
|---|---|---|
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/113016 | 12/2005 |
| WO | WO 2005/121368 | 12/2005 |
| WO | WO 2007/056113 | 5/2007 |
| WO | WO 2007/089584 | 8/2007 |
| WO | WO 2007/131237 | 11/2007 |
| WO | WO 2007/134181 | 11/2007 |
| WO | WO 2007/146511 | 12/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/007855 | 1/2009 |
| WO | WO 2009/049166 | 4/2009 |
| WO | WO 2009/060124 | 5/2009 |
| WO | WO 2010/019270 | 2/2010 |
| WO | WO 2010/148013 | 12/2010 |
| WO | WO 2011/005793 | 1/2011 |
| WO | WO 2011/135396 | 11/2011 |
| WO | 2011156673 A2 | 12/2011 |
| WO | WO 2012/005898 | 1/2012 |
| WO | WO 2012/012443 | 1/2012 |
| WO | WO 2012/012467 | 1/2012 |
| WO | WO 2012/087983 | 6/2012 |
| WO | WO 2012/092367 | 7/2012 |
| WO | WO 2012/135736 | 10/2012 |
| WO | WO 2013/030588 | 3/2013 |
| WO | WO 2013/036833 | 3/2013 |
| WO | WO 2013/075079 | 5/2013 |
| WO | WO 2013/082548 | 6/2013 |
| WO | WO 2013/086207 | 6/2013 |
| WO | WO 2013/173608 | 11/2013 |
| WO | WO 2014/062686 | 4/2014 |
| WO | WO 2014/062691 | 4/2014 |
| WO | WO 2014/062736 | 4/2014 |
| WO | WO 2014/114660 | 7/2014 |
| WO | WO 2015/054676 | 4/2015 |
| WO | WO 2016/024205 | 2/2016 |
| WO | WO 2016/050822 | 4/2016 |
| WO | WO 2016/060919 | 4/2016 |
| WO | WO 2016/168592 | 10/2016 |
| WO | WO 2017/079291 | 5/2017 |
| WO | WO 2017/180835 | 10/2017 |
| WO | WO 2018/064600 | 4/2018 |

OTHER PUBLICATIONS

"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O- Ethylene Glycol Substituted Ribonucleosides" Nucleosides & Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.

Ash et al., "Unconventional Translation of C9ORF72 GGGGCC Expansion Generates Insoluble Ploypeptides Specific to c9FTD/ALS" Neuron (2013) 77(4): 639-646.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.

Baloh, R.H., "Targeting RNA foci shows a therapeutic effect in iPSC-derived motor neurons from C9orf72 repeat patients" ALSMND meeting, Milan, Dec. 6, 2013.

Baloh, R.H., "Induced Pluripotent stem cell models from C9orf72 patients." Oral presentation, California Als PAC10 Research Summit, Los Angeles, CA, Nov. 11, 2012.

Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.

Baughn et al., "Sense and Anti-Sense RNA Foci in c9ALS/FTD: More Light in a House of Mirrors" Annals of Neurology (Oct. 14, 2013) 74(17): pS60.

Bennett et al., "Antisense oligonucleotides as a tool for gene functionalization and target validation," Biochimica et Biophysica Acta (1999) 1489: 19-30.

Bieniek et al., "Tau pathology in frontotemporal lobar degeneration with C9ORF72 hexanucleotide repeat expansion" Acta Neuropathol (2013) 125(2):289-302.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brettschneider et al., "Microglial activation correlates with disease progression and upper motor neuron clinical symptoms in Amyotrophic Lateral Sclerosis", Plos One (2012) 7:e39216.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chio et al., "Prevalence of SOD1 mutations in the Italian ALS population" Neurology (2008) 70:533-537.

(56) References Cited

OTHER PUBLICATIONS

Crooke et al., "Basic Principles of Antisense Therapeutics" Antisense Research and Application (1998) Chapter 1:1-50.
Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.
Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4dle-9569-9a1bleb21d80&cKey=c5c69155-5d2b-467c-8d1f-87299c514c7f&mKey=%7b70007181-01C9-4DE9-A0A2-EEBFA14CD9F1%7d.
Donnelly et al., "Development of C9ORF72 ALS Biomarkers and Therapeutics" American Neurological Association 2012 Annual Meeting, Poster Presentation, Boston, MA Oct. 10, 2012.
Donnelly et al., "Development of C9orf72 ALS Biomarkers and Therapeutics" Annals of Neurology (Oct. 10, 2012) 72(16):S67-S68.
Donnelly et al., "Limited availability of ZBP1 restricts axonal mRNA localization and nerve regeneration capacity" EMBO J. (2011) 30:4665-4677.
Donnelly et al., "RNA toxicity from the ALS/FTD C9ORF72 expansion is mitigated by antisense intervention" Neuron (2013) 80(2):415-428 [with Supplemental Information].
Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.
Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.
Elayadi et al., "Application of PNA and LNA oligomers to chemotherapy" Curr. Opinion Invens. Drugs (2001) 2:558-561.
European Search Report for application No. 13847957.1 dated Jul. 13, 2016.
European Search Report for application No. 13846313.8 dated May 11, 2016.
European Search Report for application No. 13847099.2 dated May 25, 2016.
Extended European Search Report for application No. 14852924.1 dated Jun. 20, 2017.
Fernandes et al., "Oligonucleotide-Based Therapy for FTD/ALS Caused by the C9orf72 Repeat Expansion: A Perspective" Journal of Nucleic Acids (2013) :1-11.
File History of U.S. Appl. No. 14/436,030, filed Apr. 15, 2015.
File History of U.S. Appl. No. 14/436,039, filed Apr. 15, 2015.
File History of U.S. Appl. No. 15/028,626, filed Apr. 11, 2016.
File History of U.S. Appl. No. 15/130,818, filed Apr. 15, 2016.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Ganesalingam et al., "Combination of neurofiliment heavy chain and complement C3 as CSF biomarkers for ALS" Journal of Neurochemistry (2011) 117: 528-537.
Gautschi et al., "Activity of a novel bcl-2/bcl-xLbispecific antisense oligonucleotide against tumors of diverse histologic origins" J. Natl. Cancer Inst. (2001) 93:463-471.
GenBank: Accession No. NT_008413 Jul. 24, 2012.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=18&satkey=24474174).
Gendron et al., "Poly(GP) proteins are a useful pharmacodynamic marker for C9ORF72-associated amyotrophic lateral sclerosis" Sci Tran Med (2017) 9(383):1-12.
Hirtz et al., "How common are the "common" neurologic disorders?" Neurology (2007) 68:326-337.
Ince et al., "Molecular pathology and genetic advances in amyotrophic lateral sclerosis: an emerging molecular pathway and the significance of glial pathology," Acta Neuro. (2011) 122:657-671.
International Search Report for application No. PCT/US2013/065073 dated Apr. 22, 2014.
International Search Report for application No. PCT/US2013/065067 dated Jan. 24, 2014.
International Search Report for application No. PCT/US2013/065131 dated Feb. 14, 2014.
International Search Report for application on. PCT/US2014/060194 dated Apr. 14, 2015.
International Search Report for application on. PCT/US2016/027747 dated Sep. 30, 2016.
International Search Report for application no. PCT/US17/27355 dated Jul. 26, 2017.
International Search Report for application No. PCT/US2016/060106 dated Feb. 1, 2017.
Jiang et al., "Antisense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.
Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.
Jeong et al., "Rapid Identification of Monospecific Monoclonal Antibodies Using a Human Proteome Microarray." Mol. Cell. Proteomics (2012) 11(6): O111.016253-1 to O111.016253-10.
Johnson et al., "Exome sequencing reveals VCP mutations as a cause of familial ALS" Neuron (2010) 68:857-864.
Jones et al., "RNA quantitation by fluorescence-based solution assay: RiboGreen reagent characterization" Analytical Biochemistry (1998) 265(2):368-374.
Klein et al., "Gain of RNA function in pathological cases: Focus on myotonic dystrophy" Biochimie (2011) 93(11):2006-2012.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Kurreck "Antisense technologies. Improvement through novel chemical modifications" Eur J Biochem (2003) 270: 1628-1644.
Kwiatkowski et al., "Mutations in the FUS/TLS gene on chromosome 16 cause familial amyotrophic lateral sclerosis" Science (2009) 323:1205-1208.
Laaksovirta et al., "Chromosome 9p21 in amyotrophic lateral sclerosis in Finland: a genome-wide association study" Lancet Neurol. (2010) 9:978-985.
Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.
Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.

(56) References Cited

OTHER PUBLICATIONS

Lagier-Tourenne, C. "Therapy Development for ALS/MND and Frontotemporal Dementia with C9orf72 Expansion: Antisense Oligonucleotide Mediated Reduction in Nuclear RNA Foci." ALS FD (Nov. 4, 2013) 14(sup2): p. 17.
Lagier-Tourenne et al., "Targeted Degradation of Sense and Antisense C9ORF72 RNA Foci as Therapy for ALS and Frontotemporal Degeneration" PNAS (2013) 110(47):E4530-E4539.
Lee et al., "Antisense Therapy in Neurology" Journal of Personalized Medicine (2013) 3(3): 144-176.
Leumann et al., "DNA Analogues: From Supramolecular Principles to Biological Properties" Bioorganic & Medicinal Chemistry (2002) 10:841-854.
Lillo et al., "Frontotemporal dementia and motor neurone disease: overlapping clinic-pathological disorders" J. Clin. Neurosci. (2009) 16:1131-1135.
Lindquist et al., "Corticobasal and ataxia syndromes widen the spectrum of C9ORF72 hexanucleotide expansion disease." Clin Genet (2013) 83:279-283.
Madson, "Antisense Against C9ORF72", http://alsn.mda.org/article/antisense-against-c90rf72 Jul. 1, 2012 (printed Oct. 28, 2015).
Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.
Mahoney et al., "Frontotemporal dementia with the C9ORF72 hexanucleotide repeat expansion: clinical, neuroanatomical and neuropathological features" Brain (2012) 135: 736-750.
Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Helv. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Mulders et al., "Triplet-repeat oligonucleotide-mediated reversal of RNA toxicity in myotonic dystrophy" PNAS (2009) 106(33):13915-13920.
Nelson et al., "The unstable repeats—three evolving faces of neurological disease." Neuron (2013) 77(5):825-43.
Neumann et al., "Ubiquitinated TDP-43 in frontotemporal lobar degeneration and amyotrophic lateral sclerosis" Science (2006) 314:130-133.
New England Biolabs 1998/99 Catalog (cover page and pp. 121 and 284).
O'Rourke et al., "C9orf72 BAC Transgenic Mice Display Typical Pathologic Features of ALS/FTD." Neuron (2015) 88(5):892-901.
Orum et al., "Locked nucleic acids: A promising molecular family for gene-function analysis and antisense drug development" Curr. Opinion Mol. Ther. (2001) 3:239-243.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Pearson et al., "Familial frontotemporal dementia with amyotrophic lateral sclerosis and a shared haplotype on chromosome 9p" J. Nerol. (2011) 258:647-655.
Rabin et al., "Sporadic ALS has compartment-specific aberrant exon splicing and altered cell-matrix adhesion biology" Hum Mol Genet. (2010) 19(2):313-328.
Ravits, J., "Expanding Neurodegenerations: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Renton et al., "A Hexanucleotide Repeat Expansion in C9ORF72 Is the Cause of Chromosome 9p21-Linked ALS-FTD" Neuron (2011) 72:257-268.
Reynolds et al., "Rational siRNA design for RNA interference" Nature Biotechnology (2004) 22(3):326-330.
Riboldi et al., "Antisense Oligonucleotide Therapy for the Treatment of C9ORF72 ALS/FTD Diseases." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sareen et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Sanghvi et al., "Heterocyclic Base Modifications in Nucleic Acids and Their Applications in Antisense Oligonucleotides" Antisense Research and Applications (1993) pp. 273-288.
Sha et al., "Treatment implications of C9ORF72" Alzheimers Res Ther (2012) 4(6): 46.
Singh et al., "LNA (locked nucleic acids): synthesis and high-affinity nucleic acid recognition" Chem. Commun. (1998) 4:455-456.
Singh et al., "Synthesis of 2'-amino-LNA: A novel conformationally restricted high-affinity oligonucleotide analogue with a handle" J. Org. Chem. (1998) 63: 10035-10039.
Simon-Sanchez et al., "The clinical and pathological phenotype of C9OFR72 hexanucleotide repeat expansions", Brain: Journal of Neurology (2012) 135:723-735.
Smith et al., "Comparison of biosequences" Adv. Appl. Math. (1981) 2(4):482-489.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Thomsen, "Dramatically improved RNA in 1-15 situ hybridization signals using LNA-modified probes" RNA (2005) 11(11): 1745-1748.
Todd et al. "RNA mediated neurodegeneration in repeat expansion disorders," Annals of Neurology (2009) 67(3):291-300.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Nat1. Acad. Sci. USA (2000) 97: 5633-5638.
Watts et al., "Silencing disease genes in the laboratory and the clinic" J Pathol (2012) 226(2): 365-379.
Wojciechowska et al., "Cellular toxicity of expanded RNA repeats: focus on RNA foci" Human Molecular Genetics (2011) 1-11.
Woolf et al., "Specificity of antisense oligonucleotides in vivo" PNAS (1992) 89: 7305-7309.
Zhang et al., "PowerBLAST: A New Network BLAST Application for Interactive or Automated Sequence Analysis and Annotation" Genome Res. (1997) 7:649-656.
Zhang et al., "The C9orf72 repeat expansion disrupts nucleocytoplasmic transport." Nature (2015) 525(7567):56-61.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

(56) References Cited

OTHER PUBLICATIONS

Boeve et al., "Characterization of frontotemporal dementia and/or amyotrophic lateral sclerosis associated with the GGGGCC repeat expansion in C9ORF72" Brain (2012) 135: 765-783.
Cook "Medicinal Chemistry of Antisense Oligonucleotides" Chapter 2—Medicinal Chemistry of Antisense Oligonucleotides, Antisense Drug Technology, 1st Edition (2001).
Lee et al., "Rnase H-mediated degradation of toxic RNA in myotonic dystrophy type 1" PNAS (2012) 109: 4221-4226.
Mori et al., "Bidirectional transcripts of the expanded C9orf72 hexanucleotide repeat are translated into aggregating dipeptide repeat proteins" Acata Neuropathol (2013) 126: 881-893.
Shao et al., "Rational design and rapid screening of antisense oligonucleotides for prokaryotic gene modulation" Nucleic Acids Res (2006) 34: 5660-5669.
Sohail et al., "Selecting optimal antisense reagents" Adv Drug Deliv Rev (2000) 44: 23-34.
Wheeler et al., "Targeting nuclear RNA for in vivo correction of myotonic dystrophy" Nature (2012) 488: 111-117.
Extended EP Search Report for 22197003.1 dated Jun. 30, 2023.
Ciura et al., "Loss of function of C9orf72 causes motor deficits in a zebrafish model of amyotrophic lateral sclerosis" Ann Neurol (2013) 74(2): 180-187.
GenBank Accession No. NG_031977.1 *Homo sapiens* chromosome 9 open reading frame 72 (C9orf72), RefSeqGene on chromosome 9 (available Mar. 28, 2013).
Gendron et al., "c9RAN translation: a potential therapeutic target for the treatment of amyotrophic lateral sclerosis and frontotemporal dementia" Expert Opinion on Therapeutic Targets (2013) 17: 991-995.
GeneToolsLLC "Morpholio Antisense Oligos" p. 1-2 available Jan. 7, 2012 according to Wayback Machine (2012).
Ho et al., "Modification of phosphorothioate oligonucleotides yields potent analogs with minimal toxicity for antisense experiments in the CNS" Molecular Brain Res (1998) 62: 1-11.
Kole et al., "RNA therapeutics: beyond RNA interference and antisense oligonucleotides" Nature Reviews Drug Discovery (2012) 11: 125-140.
Ostergaard et al., "Rational design of antisense oligonucleotides targeting single nucleotide polymorphisms for potent and allele selective suppression of mutant Huntintin in the CNS" Nucl Acids Res (2013) 41: 9634-9650.

SEQUENCE LISTING

```
Sequence total quantity: 370
SEQ ID NO: 1          moltype = RNA  length = 3339
FEATURE               Location/Qualifiers
source                1..3339
                      mol_type = mRNA
                      organism = Homo sapiens
```

-continued

```
SEQUENCE: 1
acgtaaccta cggtgtcccg ctaggaaaga gaggtgcgtc aaacagcgac aagttccgcc  60
cacgtaaaag atgacgcttg gtgtgtcagc cgtccctgct gcccggttgc ttctcttttg  120
ggggcggggt ctagcaagag caggtgtggg tttaggagat atctccggag catttggata  180
atgtgacagt tggaatgcag tgatgtcgac tctttgccca ccgccatctc cagctgttgc  240
caagacagag attgctttaa gtggcaaatc acctttatta gcagctactt ttgcttactg  300
ggacaatatt cttggtccta gagtaaggca catttgggct ccaaagacag aacaggtact  360
tctcagtgat ggagaaataa cttttcttgc caaccacact ctaaatggag aaatccttcg  420
aaatgcagag agtggtgcta tagatgtaaa gtttttttgtc ttgtctgaaa agggagtgat  480
tattgtttca ttaatctttg atggaaactg gaatggggat cgcagcacat atggactatc  540
aattatactt ccacagacag aacttagttt ctacctccca cttcatagag tgtgtgttga  600
tagattaaca catataatcc ggaaaggaag aatatggatg cataaggaaa gacaagaaaa  660
tgtccagaag attatcttag aaggcacaga gagaatggaa gatcagggtc agagtattat  720
tccaatgctt actggagaag tgattcctgt aatggaactg ctttcatcta tgaaatcaca  780
cagtgttcct gaagaaatag atatagctga tacagtactc aatgatgatg atattggtga  840
cagctgtcat gaaggctttc ttctcaatgc catcagctca cacttgcaaa cctgtggctg  900
ttccgttgta gtaggtagca gtgcagagaa agtaaataag atagtcagaa cattatgcct  960
ttttctgact ccagcagaga gaaaatgctc caggttatgt gaagcagaat catcatttaa  1020
atatgagtca gggctctttg tacaaggcct gctaaaggat tcaactggaa gctttgtgct  1080
gcctttccgg caagtcatgt atgctccata tcccaccaca cacatagatg tggatgtcaa  1140
tactgtgaag cagatgccac cctgtcatga acatatttat aatcagcgta gatacatgag  1200
atccgagctg acagccttct ggagagccac ttcagaagaa gacatggctc aggatacgat  1260
catctacact gacgaaagct ttactcctga tttgaatatt tttcaagatg tcttacacag  1320
agacactcta gtgaaagcct tcctggatca ggtctttcag ctgaaacctg gcttatctct  1380
cagaagtact ttccttgcac agtttctact tgtccttcac agaaaagcct tgacactaat  1440
aaaatatata gaagacgata cgcagaaggg aaaaaagccc tttaaatctc ttcggaacct  1500
gaagatagac cttgatttaa cagcagaggg cgatcttaac ataataatgg ctctggctga  1560
gaaaattaaa ccaggcctac actcttttat ctttggaaga cctttctaca ctagtgtgca  1620
agaacgagat gttctaatga ctttttaaat gtgtaactta ataagcctat tccatcacaa  1680
tcatgatcgc tggtaaagta gctcagtggt gtggggaaac gttcccctgg atcatactcc  1740
agaattctgc tctcagcaat tgcagttaag taagttacac tacagttctc acaagagcct  1800
gtgaggggat gtcaggtgca tcattacatt gggtgtctct tttcctagat ttatgctttt  1860
gggatacaga cctatgttta caatataata aatattattg ctatctttta aagatataat  1920
aataggatgt aaacttgacc acaactactg ttttttttgaa atacatgatt catggtttac  1980
atgtgtcaag gtgaaatctg agttggcttt tacagatagt tgactttcta tcttttggca  2040
ttctttggtg tgtagaatta ctgtaatact tctgcaatca actgaaaact agagcctttta  2100
aatgatttca attccacaga aagaaagtga gcttgaacat aggatgagct ttagaaagaa  2160
aattgatcaa gcagatgttt aattggaatt gattattaga tcctactttg tggatttagt  2220
ccctgggatt cagtctgtag aaatgtctaa tagttctcta tagtccttgt tcctggtgaa  2280
ccacagttag ggtgttttgt ttattttatt gttcttgcta ttgttgatat tctatgtagt  2340
tgagctctgt aaaaggaaat tgtattttat gttttagtaa ttgttgccaa ctttttaaat  2400
taattttcat tatttttgag ccaaattgaa atgtgcacct cctgtgcctt ttttctcctt  2460
agaaaatcta attacttgga acaagttcag atttcactgg tcagtcattt tcatcttgtt  2520
ttcttcttgc taagtcttac catgtacctg ctttggcaat cattgcaact ctgagattat  2580
aaaatgcctt agagaatata ctaactaata agatcttttt ttcagaaaca gaaaatagtt  2640
ccttgagtac ttccttcttg catttctgcc tatgtttttg aagttgttgc tgtttgcctg  2700
caataggcta taaggaatag caggagaaat tttactgaag tgctgttttc ctaggtgcta  2760
ctttggcaga gctaagttat cttttgtttt cttaatgcgt ttggaccatt ttgctggcta  2820
taaaataact gattaatata attctaacac aatgttgaca ttgtagttac acaaacacaa  2880
ataaatattt tatttaaaat tctggaagta atataaaagg gaaaatatat ttataagaaa  2940
gggataaagg taatagagcc cttctgcccc ccacccacca aatttacaca acaaaatgac  3000
atgttcgaat gtgaaaggtc ataatagctt tcccatcatg aatcagaaag atgtggacag  3060
cttgatgttt tagacaacca ctgaactaga tgactgttgt actgtagctc agtcatttaa  3120
aaaatatata aatactacct tgtagtgtcc catactgtgt tttttacatg gtagattctt  3180
atttaagtgc taactggtta ttttctttgg ctggtttatt gtactgttat acagaatgta  3240
agttgtacag tgaaataagt tattaaagca tgtgtaaaca ttgttatata tcttttctcc  3300
taaatggaga attttgaata aaatatattt gaaattttg                        3339

SEQ ID NO: 2           moltype = DNA  length = 30001
FEATURE                Location/Qualifiers
source                 1..30001
                       mol_type = genomic DNA
                       organism = Homo sapiens
SEQUENCE: 2
caaagaaaag ggggaggttt tgttaaaaaa gagaaatgtt acatagtgct ctttgagaaa  60
attcattggc actattaagg atctgaggag ctggtgagtt tcaactggtg agtgatggtg  120
gtagataaaa ttagagctgc agcaggtcat tttagcaact attagataaa actggtctca  180
ggtcacaacg ggcagttgca gcagctggac ttggagagaa ttacactgtg ggagcagtgt  240
catttgtcct aagtgctttt ctacccccta cccccactat tttagttggg tataaaaaga  300
atgacccaat ttgtatgatc aactttcaca aagcatagaa cagtaggaaa agggtctgtt  360
tctgcagaag gtgtagacgt tgagagccat tttgtgtatt tattcctccc tttcttcctc  420
ggtgaatgat taaaacgttc tgtgtgattt ttagtgatga aaaagattaa atgctactca  480
ctgtagtaag tgccatctca cacttgcaga tcaaaaggca cacagtttaa aaaacctttg  540
tttttttaca catctgagtg gtgtaaatgc tactcatctg tagtaagtgg aatctataca  600
cctgcagacc aaaagacgca aggtttcaaa aatctttgtg ttttttacac atcaaacaga  660
atggtacgtt tttcaaaagt taaaaaaaaa caactcatcc acatattgca actagcaaaa  720
atgacattcc ccagtgtgaa aatcatgctt gagagaattc ttacatgtaa aggcaaaatt  780
gcgatgactt tgcaggggac cgtgggattc ccgcccgcag tgccggagct gtcccctacc  840
agggtttgca gtggagtttt gaatgcactt aacagtgtct tacggtaaaa acaaaatttc  900
```

-continued

```
atccaccaat tatgtgttga gcgcccactg cctaccaagc acaaacaaaa ccattcaaaa  960
ccacgaaatc gtcttcactt tctccagatc cagcagcctc ccctattaag gttcgcacac  1020
gctattgcgc caacgctcct ccagagcggg tcttaagata aaagaacagg acaagttgcc  1080
ccgccccatt tcgctagcct cgtgagaaaa cgtcatcgca catagaaaac agacagacgt  1140
aacctacggt gtcccgctag gaaagagagg tgcgtcaaac agcgacaagt tccgcccacg  1200
taaaagatga cgcttggtgt gtcagccgtc cctgctgccc ggttgcttct cttttggggg  1260
cggggtctag caagagcagg tgtgggttta ggaggtgtgt gtttttgttt ttcccaccct  1320
ctctccccac tacttgctct cacagtactc gctgagggtg aacaagaaaa gacctgataa  1380
agattaacca gaagaaaaca aggagggaaa caaccgcagc ctgtagcaag ctctggaact  1440
caggagtcgc gcgctagggg ccggggccgg ggccggggcg tggtcggggc gggcccgggg  1500
gcgggcccgg ggcggggctg cggttgcggt gcctgcgccc gcggcggcgg aggcgcaggc  1560
ggtggcgagt gggtgagtga ggaggcggca tcctggcggg tggctgtttg gggttcggct  1620
gccgggaaga ggcgcgggta gaagcggggg ctctcctcag agctcgacgc atttttactt  1680
tccctctcat ttctctgacc gaagctgggt gtcgggcttt cgcctctagc gactggtgga  1740
attgcctgca tccgggcccc gggcttcccg gcggcggcgg cggcggcggc ggcgcaggga  1800
caagggatgg ggatctggcc tcttccttgc tttcccgccc tcagtacccg agctgtctcc  1860
ttcccgggga cccgctggga gcgctgccgc tgcgggctcg agaaaaggga gcctcgggta  1920
ctgagaggcc tcgcctgggg gaaggccgga gggtgggcgg cgcgcggctt ctgcggacca  1980
agtcggggtt cgctaggaac ccgagacggt ccctgccggc gaggagatca tgcgggatga  2040
gatgggggtg tggagacgcc tgcacaattt cagcccaagc ttctagagag tggtgatgac  2100
ttgcatatga gggcagcaat gcaagtcggt gtgctcccca ttctgtggga catgacctgg  2160
ttgcttcaca gctccgagat gacacagact tgcttaaagg aagtgactat tgtgacttgg  2220
gcatcacttg actgatggta atcagttgtc taaagaagtg cacagattac atgtccgtgt  2280
gctcattggg tctatctggc cgcgttgaac accaccaggc tttgtattca gaaacaggag  2340
ggaggtcctg cactttccca ggaggggtgg ccctttcaga tgcaatcgag attgttaggc  2400
tctgggagag tagttgcctg gttgtggcag ttggtaaatt tctattcaaa cagttgccat  2460
gcaccagttg ttcacaacaa gggtacgtaa tctgtctggc attacttcta cttttgtaca  2520
aaggatcaaa aaaaaaaaag atactgttaa gatatgattt ttctcagact ttgggaaact  2580
tttaacataa tctgtgaata tcacagaaac aagactatca tataggggat attaataacc  2640
tggagtcaga atacttgaaa tacggtgtca tttgacacgg gcattgttgt caccacctct  2700
gccaaggcct gccactttag gaaaaccctg aatcagttgg aaactgctac atgctgatag  2760
tacatctgaa acaagaacga gagtaattac cacattccag attgttcact aagccagcat  2820
ttacctgctc caggaaaaaa ttacaagcac cttatgaagt tgataaaata ttttgtttgg  2880
ctatgttggc actccacaat ttgctttcag agaaacaaag taaaccaagg aggacttctg  2940
tttttcaagt ctgccctcgg gttctattct acgttaatta gatagttccc aggaggacta  3000
ggttagccta cctattgtct gagaaacttg gaactgtgag aaatggccag atagtgatat  3060
gaacttcacc ttccagtctt ccctgatgtt gaagattgag aaagtgttgt gaactttctg  3120
gtactgtaaa cagttcactg tccttgaagt ggtcctgggc agctcctgtt gtggaaagtg  3180
gacggtttag gatcctgctt ctctttgggc tgggagaaaa taaacagcat ggttacaagt  3240
attgagagcc aggttggaga aggtggctta cacctgtaat gccagagctt tgggaggcgg  3300
aggcaagagg atcacttgaa gccaggagtt caagctcaac ctgggcaacg tagaccctgt  3360
ctctacaaaa aattaaaaac ttagccgggc gtggtgatgt gcacctgtag tcctagctac  3420
ttgggaggct gaggcaggag ggtcatttga gcccaagagt ttgaagttac cgagagctat  3480
gatcctgcca gtgcattcca gcctggatga caaaacgaga ccctgtctct aaaaaacaag  3540
aagtgagggc tttatgattg tagaattttc actacaatag cagtggacca accacctttc  3600
taaataccaa tcagggaaga gatggttgat tttttaacag acgtttaaag aaaaagcaaa  3660
acctcaaact tagcactcta ctaacagttt tagcagatgt taattaatgt aatcatgtct  3720
gcatgtatgg gattatttcc agaaagtgta ttgggaaacc tctcatgaac cctgtgagca  3780
agccaccgtc tcactcaatt tgaatcttgg cttccctcaa aagactggct aatgtttggt  3840
aactctctgg agtagacagc actacatgta cgtaagatag gtacataaac aactattggt  3900
tttgagctga tttttttcag ctgcatttgc atgtatggat tttctcacc aaagacgatg  3960
acttcaagta ttagtaaaat aattgtacag ctctcctgat tatacttctc tgtgacattt  4020
catttcccag gctatttctt ttggtaggat ttaaaactaa gcaattcagt atgatctttg  4080
tccttcattt tctttcttat tctttttgtt tgtttgtttg tttgtttttt tcttgaggca  4140
gagtctctct ctgtcgccca ggctggagtg cagtggcgcc atctcagctc attgcaacct  4200
ctgccacctc cgggttcaag agattctcct gcctcagcct cccgagtagc tgggattaca  4260
ggtgtccacc accacacccg gctaattttt tgtattttta gtagaggtgg ggtttcacca  4320
tgttggccag gctggtcttg agctcctgac ctcaggtgat ccacctgcct cggcctacca  4380
aagagctggg ataacaggtg tgacccacca tgcccggccc attttttttt tcttattctg  4440
ttaggagtga gagtgtaact agcagtataa tagttcaatt ttcacaacgt ggtaaaagtt  4500
tccctataat tcaatcagat tttgctccag ggttcagttc tgttttagga aatactttta  4560
ttttcagttt aatgatgaaa tattagagtt gtaatattgc ctttatgatt atccaccttt  4620
ttaacctaaa agaatgaaag aaaaatatgt ttgcaatata attttatggt tgtatgttaa  4680
cttaattcat tatgttggcc tccagtttgc tgttgttagt tatgacagca gtagtgtcat  4740
taccatttca attcagatta cattcctata tttgatcatt gtaaactgac tgcttacatt  4800
gtattaaaaa cagtggatat tttaaagaag ctgtacggct tatatctagt gctgtctctt  4860
aagactatta aattgataca acatatttaa aagtaaatat tacctaaatg aatttttgaa  4920
attacaaata cacgtgttaa aactgtcgtt gtgttcaacc atttctgtac atacttagag  4980
ttaactgttt tgccaggctc tgtatgccta ctcataatat gataaaagca ctcatctaat  5040
gctctgtaaa tagaagtcag tgctttccat cagactgaac tctcttgaca agatgtggat  5100
gaaattcttt aagtaaaatt gtttactttg tcatacattt acagatcaaa tgttagctcc  5160
caaagcaatc atatggcaaa gataggtata tcatagtttg cctattagct gctttgtatt  5220
gctattatta taaatagact tcacagtttt agacttgctt aggtgaaatt gcaattcttt  5280
ttactttcag tcttagataa caagtcttca attatagtac aatcacacat tgcttaggaa  5340
tgcatcatta ggcgatttg tcattatgca aacatcatag agtgtactta cacaaaccta  5400
gatagtatag cctttatgta cctaggccgt atggtatagt ctgttgctcc taggccacaa  5460
acctgtacaa ctgttactgt actgaatact atagacagtt gtaacacagt ggtaaatatt  5520
tatctaaata tatgcaaaca gagaaaaggt acagtaaaag tatggtataa aagataatgg  5580
tatacctgtg taggccactt accacgaatg gagcttgcag gactagaagt tgctctgggt  5640
```

-continued

```
gagtcagtga gtgagtggtg aattaatgtg aaggcctaga acactgtaca ccactgtaga  5700
ctataaacac agtacgctga agctacacca aatttatctt aacagttttt cttcaataaa  5760
aaattataac tttttaactt tgtaaacttt ttaatttttt aacttttaaa atacttagct  5820
tgaaacacaa atacattgta tagctataca aaaatatttt ttctttgtat ccttattcta  5880
gaagcttttt tctattttct attttaaatt ttttttttta cttgttagtc gtttttgtta  5940
aaaactaaaa cacacacact ttcacctagg catagacagg attaggatca tcagtatcac  6000
tcccttccac ctcactgcct tccacctcca catcttgtcc cactggaagg tttttagggg  6060
caataacaca catgtagctg tcacctatga taacagtgct ttctgttgaa tacctcctga  6120
aggacttgcc tgaggctgtt ttacatttaa cttaaaaaaa aaaaaagtag aaggagtgca  6180
ctctaaaata acaataaaag gcatagtata gtgaatacat aaaccagcaa tgtagtagtt  6240
tattatcaag tgttgtacac tgtaataatt gtatgtgcta tactttaaat aacttgcaaa  6300
atagtactaa gaccttatga tggttacagt gtcactaagg caatagcata ttttcaggtc  6360
cattgtaatc taatgggact accatcatat atgcagtcta ccattgactg aaacgttaca  6420
tggcacataa ctgtatttgc aagaatgatt tgttttacat taatatcaca taggatgtac  6480
ctttttagag tggtatgttt atgtggatta agatgtacaa gttgagcaag gggaccaaga  6540
gccctgggtt ctgtcttgga tgtgagcgtt tatgttcttc tcctcatgtc tgtttctca   6600
ttaaattcaa aggcttgaac gggccctatt tagcccttct gttttctacg tgttctaaat  6660
aactaaagct tttaaattct agccatttag tgtagaactc tctttgcagt gatgaaatgc  6720
tgtattggtt tcttggctag catattaaat atttttatct ttgtcttgat acttcaatgt  6780
cgttttaaac atcaggatcg ggcttcagta ttctcataac cagagagttc actgaggata  6840
caggactgtt tgcccatttt ttgttatggc tccagacttg tggtatttcc atgtcttttt  6900
ttttttttt tttttgacc ttttagcggc tttaaagtat ttctgttgtt aggtgttgta   6960
ttacttttct aagattactt aacaaagcac cacaaactga gtggctttaa acaacagcaa  7020
tttattctct cacaattcta gaagctagaa gtccgaaatc aaagtgttga caggggcatg  7080
atcttcaaga gagaagactc tttccttgcc tcttcctggc ttctggtggt taccagcaat  7140
cctgagtgtt cctttcttgc cttgtagttt caacaatcca gtatctgcct tttgtcttca  7200
catggctgtc taccatttgt ctctgtgtct ccaaatctct ctccttataa acacagcagt  7260
tattggatta ggccccactc taatccagta tgaccccatt ttaacatgat tacacttatt  7320
tctagataag gtcacattca cgtacaccaa gggttaggaa ttgaacatat ctttttgggg  7380
gacacaattc aacccacaag tgtcagtctc tagctgagcc tttcccttcc tgtttttctc  7440
ctttttagtt gctatgggtt aggggccaaa tctccagtca tactagaatt gcacatggac  7500
tggatatttg ggaatactgc gggtctattc tatgagcttt agtatgtaac atttaatatc  7560
agtgtaaaga agcccttttt taagttattt ctttgaattt ctaaatgtat gccctgaata  7620
taagtaacaa gttaccatgt cttgtaaaat gatcatatca acaaacattt aatgtgcacc  7680
tactgtgcta gttgaatgtc tttatcctga taggagataa caggattcca catctttgac  7740
ttaagaggac aaaccaaata tgtctaaatc atttggggtt ttgatggata tctttaaatt  7800
gctgaaccta atcattggtt tcatatgtca ttgtttagat atctccggag catttggata  7860
atgtgacagt tggaatgcag tgatgtcgac tctttgccca ccgccatctc cagctgttgc  7920
caagacagag attgctttaa gtggcaaatc acctttatta gcagctactt ttgcttactg  7980
ggacaatatt cttggtccta gagtaaggca catttgggct ccaaagacag aacaggtact  8040
tctcagtgat ggagaaataa cttttcttgc caaccacact ctaaatggag aaatccttcg  8100
aaatgcagag agtggtgcta tagatgtaaa gttttttgtc ttgtctgaaa agggagtgat  8160
tattgtttca ttaatctttg atggaaactg gaatggggat cgcagcacat atggactatc  8220
aattatactt ccacagacag aacttagttt ctacctccca cttcatagag tgtgtgttga  8280
tagattaaca catataatcc ggaaaggaag aatatggatg cataaggtaa gtgatttttc  8340
agcttattaa tcatgttaac ctatctgttg aaagcttatt ttctggtaca tataaatctt  8400
atttttttaa ttatatgcag tgaacatcaa acaataaatg ttatttattt tgcatttacc  8460
ctattagata caaatacatc tggtctgata cctgtcatct tcatattaac tgtggaaggt  8520
acgaaatggt agctccacat tatagatgaa aagctaaagc ttagacaaat aaagaaactt  8580
ttagaccctg gattcttctt gggagccttt gactctaata ccttttgttt cccttttcatt  8640
gcacaattct gtcttttgct tactactatg tgtaagtata acagttcaaa gtaatagttt  8700
cataagctgt tggtcatgta gcctttggtc tctttaacct ctttgccaag ttcccaggtt  8760
cataaaatga ggaggttgaa tggaatggtt cccaagagaa ttccttttaa tcttacagaa  8820
attattgttt tcctaaatcc tgtagttgaa tatataatgc tatttacatt tcagtatagt  8880
tttgatgtat ctaaagaaca cattgaattc tccttcctgt gttccagttt gatactaacc  8940
tgaaagtcca ttaagcatta ccagttttaa aaggcttttg cccaatagta aggaaaaata  9000
atatctttta aaagaataat tttttactat gtttgcaggc ttacttcctt ttttctcaca  9060
ttatgaaact cttaaaatca ggagaatctt ttaaacaaca tcataatgtt taatttgaaa  9120
agtgcaagtc attcttttcc tttttgaaac tatgcagatg ttacattgac tgttttctgt  9180
gaagttatct ttttttcact gcagaataaa ggttgttttg attttatttt gtattgttta  9240
tgagaacatg catttgttgg gttaatttcc taccccctgcc cccatttttt ccctaaagta  9300
gaaagtattt ttcttgtgaa ctaaattact acacaagaac atgtctattg aaaaataagc  9360
aagtatcaaa atgttgtggg ttgttttttt aaataaattt tctcttgctc aggaaagaca  9420
agaaaatgtc cagaagatta tcttagaagg cacagagaga atggaagatc aggtatatgc  9480
aaattgcata ctgtcaaatg tttttctcac agcatgtatc tgtataaggt tgatggctac  9540
atttgtcaag gccttggaga catacgaata agcctttaat ggagctttta tggaggtgta  9600
cagaataaac tggaggaaga tttccatatc ttaaacccaa agagttaaat cagtaaacaa  9660
aggaaaatag taattgcatc tacaaattaa tatttgctcc cttttttttt ctgtttgccc  9720
agaataaatt ttggataact tgttcatagt aaaaataaaa aaaattgtct ctgatatgtt  9780
ctttaaggta ctacttctcg aacctttccc tagaagtagc tgtaacagaa ggagagcata  9840
tgtacccctg aggtatctgt ctggggtgta ggcccaggtc cacacaatat ttcttctaag  9900
tcttatgttg tatcgttaag actcatgcaa tttacatttt attccataac tatttttagta  9960
ttaaaatttg tcagtgatat ttcttaccct ctcctctagg aaaatgtgcc atgtttatcc  10020
cttggctttg aatgcccctc aggaacagac actaagagtt tgagaagcat ggttacaagg  10080
gtgtggcttc ccctgcggaa actaagtaca gactatttca ctgtaaagca gagaagttct  10140
tttgaaggag aatctccagt gaagaaagag ttcttcactt ttacttccat ttcctcttgt  10200
gggtgaccct caatgctcct tgtaaaactc caatatttta aacatggctg ttttgccttt  10260
ctttgcttct ttttagcatg aatgagacag atgatacttt aaaaaagtaa ttaaaaaaaa  10320
aaacttgtga aaatacatgg ccataataca gaacccaata caatgatctc ctttaccaaa  10380
```

-continued

```
ttgttatgtt tgtacttttg tagatagctt tccaattcag agacagttat tctgtgtaaa  10440
ggtctgactt aacaagaaaa gatttccctt tacccaaaga atcccagtcc ttatttgctg  10500
gtcaataagc agggtcccca ggaatggggt aactttcagc accctctaac ccactagtta  10560
ttagtagact aattaagtaa acttatcgca agttgaggaa acttagaacc aactaaaatt  10620
ctgcttttac tgggattttg ttttttcaaa ccagaaacct ttacttaagt tgactactat  10680
taatgaattt tggtctctct tttaagtgct cttcttaaaa atgttatctt actgctgaga  10740
agttcaagtt tgggaagtac aaggaggaat agaaacttaa gagattttct tttagagcct  10800
cttctgtatt tagccctgta ggattttttt tttttttttt ttttttggtg ttgttgagct  10860
tcagtgaggc tattcattca cttatactga taatgtctga gatactgtga atgaaatact  10920
atgtatgctt aaacctaaga ggaaatattt tcccaaaatt attcttcccg aaaaggagga  10980
gttgcctttt gattgagttc ttgcaaatct cacaacgact ttattttgaa caatactgtt  11040
tggggatgat gcattagttt gaaacaactt cagttgtagc tgtcatctga taaaattgct  11100
tcacagggaa ggaaatttaa cacggatcta gtcattattc ttgttagatt gaatgtgtga  11160
attgtaattg taaacaggca tgataattat tactttaaaa actaaaaaca gtgaatagtt  11220
agttgtggag gttactaaag gatggttttt ttttaaataa aactttcagc attatgcaaa  11280
tgggcatatg gcttaggata aaacttccag aagtagcatc acatttaaat tctcaagcaa  11340
cttaataata tggggctctg aaaaactggt taaggttact ccaaaaatgg ccctgggtct  11400
gacaaagatt ctaacttaaa gatgcttatg aagactttga gtaaaatcat ttcataaaat  11460
aagtgaggaa aaacaactag tattaaattc atcttaaata atgtatgatt taaaaaatat  11520
gtttagctaa aaatgcatag tcatttgaca atttcattta tatctcaaaa aatttactta  11580
accaagttgg tcacaaaact gatgagactg gtggtggtag tgaataaatg agggaccatc  11640
catatttgag acactttaca tttgtgatgt gttatactga attttcagtt tgattctata  11700
gactacaaat ttcaaaatta caatttcaag atgtaataag tagtaatatc ttgaaatagc  11760
tctaaaggga atttttctgt tttattgatt cttaaaatat atgtgctgat tttgatttgc  11820
atttgggtag attatacttt tatgagtatg gaggttaggt attgattcaa gttttcctta  11880
cctatttggt aaggatttca aagtcttttt gtgcttggtt ttcctcattt ttaaatatga  11940
aatatattga tgacctttaa caaatttttt ttatctcaaa ttttaaagga gatcttttct  12000
aaaagaggca tgatgactta atcattgcat gtaacagtaa acgataaacc aatgattcca  12060
tactctctaa agaataaaag tgagctttag ggccgggcat ggtcagaaat ttgacaccaa  12120
cctggccaac atggcgaaac cccgtctcta ctaaaaatac aaaaatcagc cgggcatggt  12180
ggcggcacct atagtcccag ctacttggga ggatgagaca ggagagtcac ttgaacctgg  12240
gaggagaggt tgcagtgagc tgagatcacg ccattgcact ccagcctgag caatgaaagc  12300
aaaactccat ctcaaaaaaa aaaaaagaaa agaaagaata aaagtgagct ttggattgca  12360
tataaatcct ttagacatgt agtagacttg tttgatactg tgtttgaaca aattacgaag  12420
tattttcatc aaagaatgtt attgtttgat gttattttta tttttattg cccagcttct  12480
ctcatattac gtgattttct tcacttcatg tcactttatt gtgcagggtc agagtattat  12540
tccaatgctt actggagaag tgattcctgt aatggaactg ctttcatcta tgaaatcaca  12600
cagtgttcct gaagaaatag atgtaagttt aaatgagagc aattatacac tttatgagtt  12660
ttttggggtt atagtattat tatgtatatt attaatattc taattttaat agtaaggact  12720
ttgtcataca tactattcac atacagtatt agccacttta gcaaataagc acacacaaaa  12780
tcctggattt tatggcaaaa cagaggcatt tttgatcagt gatgacaaaa ttaaattcat  12840
tttgtttatt tcattacttt tataattcct aaaagtggga ggatcccagc tcttatagga  12900
gcaattaata tttaatgtag tgtcttttga aacaaaactg tgtgccaaag tagtaaccat  12960
taatggaagt ttacttgtag tcacaaattt agtttcctta atcatttgtt gaggacgttt  13020
tgaatcacac actatgagtg ttaagagata cctttaggaa actattcttg ttgttttctg  13080
attttgtcat ttaggttagt ctcctgattc tgacagctca gaagaggaag ttgttcttgt  13140
aaaaattgtt taacctgctt gaccagcttt cacatttgtt cttctgaagt ttatggtagt  13200
gcacagagat tgtttttttgg ggagtcttga ttctcggaaa tgaaggcagt gtgttatatt  13260
gaatccagac ttccgaaaac ttgtatatta aaagtgttat ttcaacacta tgttacagcc  13320
agactaattt ttttattttt tgatgcattt tagatagctg atacagtact caatgatgat  13380
gatattggtg acagctgtca tgaaggcttt cttctcaagt aagaattttt cttttcataa  13440
aagctggatg aagcagatac catcttatgc tcacctatga caagatttgg aagaaagaaa  13500
ataacagact gtctacttag attgttctag ggacattacg tatttgaact gttgcttaaa  13560
tttgtgttat ttttcactca ttatatttct atatatattt ggtgttattc catttgctat  13620
ttaaagaaac cgagtttcca tcccagacaa gaaatcatgg ccccttgctt gattctggtt  13680
tcttgtttta cttctcatta aagctaacag aatcctttca tattaagttg tactgtagat  13740
gaacttaagt tatttaggcg tagaacaaaa ttattcatat ttatactgat ctttttccat  13800
ccagcagtgg agtttagtac ttaagagttt gtgcccttaa accagactcc ctggattaat  13860
gctgtgtacc cgtgggcaag gtgcctgaat tctctataca cctatttcct catctgtaaa  13920
atggcaataa tagtaatagt acctaatgtg tagggttgtt ataagcattg agtaagataa  13980
ataaatataa gcacttagaa cagtgcctgg aacataaaaa cacttaataa tagctcatag  14040
ctaacatttc ctatttacat ttcttctaga aatagccagt atttgttgag tgcctacatg  14100
ttagttcctt tactagttgc tttacatgta ttatcttata ttctgtttta aagtttcttc  14160
acagttacag attttcatga aattttactt ttaataaaag agaagtaaaa gtataaagta  14220
ttcactttta tgttcacagt cttttccttt aggctcatga tggagtatca gaggcatgag  14280
tgtgtttaac ctaagagcct taatggcttg aatcagaagc actttagtcc tgtatctgtt  14340
cagtgtcagc ctttcataca tcattttaaa tcccatttga ctttaagtaa gtcacttaat  14400
ctctctacat gtcaatttct tcagctataa aatgatggta tttcaataaa taaatacatt  14460
aattaaatga tattatactg actaattggg ctgttttaag gctcaataag aaaatttctg  14520
tgaaaggtct ctagaaaatg taggttccta tacaaataaa agataacatt gtgcttatag  14580
cttcggtgtt tatcatataa agctattctg agttatttga agagctcacc tacttttttt  14640
tgtttttagt ttgttaaatt gttttatagg caatgttttt aatctgtttt ctttaactta  14700
```

-continued

```
cagtgccatc agctcacact tgcaaacctg tggctgttcc gttgtagtag gtagcagtgc  14760
agagaaagta aataaggtag tttattttat aatctagcaa atgatttgac tctttaagac  14820
tgatgatata tcatggattg tcatttaaat ggtaggttgc aattaaaatg atctagtagt  14880
ataaggaggc aatgtaatct catcaaattg ctaagacacc ttgtggcaac agtgagtttg  14940
aaataaactg agtaagaatc atttatcagt ttattttgat agctcggaaa taccagtgtc  15000
agtagtgtat aaatggtttt gagaatatat taaaatcaga tatataaaaa aaattactct  15060
tctatttccc aatgttatct ttaacaaatc tgaagatagt catgtacttt tggtagtagt  15120
tccaaagaaa tgttatttgt ttattcatct tgatttcatt gtcttcgctt tccttctaaa  15180
tctgtccctt ctagggagct attgggatta agtggtcatt gattattata ctttattcag  15240
taatgtttct gaccctttcc ttcagtgcta cttgagttaa ttaaggatta atgaacagtt  15300
acatttccaa gcattagcta ataaactaaa ggattttgca cttttcttca ctgaccatta  15360
gttagaaaga gttcagagat aagtatgtgt atctttcaat ttcagcaaac ctaatttttt  15420
aaaaaaagtt ttacatagga aatatgttgg aaatgatact ttacaaagat attcataatt  15480
tttttttgta atcagctact ttgtatattt acatgagcct taatttatat ttctcatata  15540
accatttatg agagcttagt atacctgtgt cattatattg catctacgaa ctagtgacct  15600
tattccttct gttacctcaa acaggtggct ttccatctgt gatctccaaa gccttaggtt  15660
gcacagagtg actgccgagc tgctttatga agggagaaag gctccatagt tggagtgttt  15720
tttttttttt ttttaaacat ttttcccatc ctccatcctc ttgagggaga atagcttacc  15780
ttttatcttg ttttaatttg agaaagaagt tgccaccact ctaggttgaa aaccactcct  15840
ttaacataat aactgtggat atggtttgaa tttcaagata gttacatgcc tttttatttt  15900
tcctaataga gctgtaggtc aaatattatt agaatcagat ttctaaatcc cacccaatga  15960
cctgcttatt ttaaatcaaa ttcaataatt aattctcttc tttttggagg atctggacat  16020
tctttgatat ttcttacaac gaatttcatg tgtagaccca ctaaacagaa gctataaaag  16080
ttgcatggtc aaataagtct gagaaagtct gcagatgata taattcacct gaagagtcac  16140
agtatgtagc caaatgttaa aggttttgag atgccataca gtaaatttac caagcatttt  16200
ctaaatttat ttgaccacag aatccctatt ttaagcaaca actgttacat cccatggatt  16260
ccaggtgact aaagaatact tatttcttag gatatgtttt attgataata acaattaaaa  16320
tttcagatat ctttcataag caaatcagtg gtctttttac ttcatgtttt aatgctaaaa  16380
tattttcttt tatagatagt cagaacatta tgcctttttc tgactccagc agagagaaaa  16440
tgctccaggt tatgtgaagc agaatcatca tttaaatatg agtcagggct ctttgtacaa  16500
ggcctgctaa aggtatagtt tctagttatc acaagtgaaa ccacttttct aaaatcattt  16560
ttgagactct ttatagacaa atcttaaata ttagcattta atgtatctca tattgacatg  16620
cccagagact gacttccttt acacagttct gcacatagac tatatgtctt atggatttat  16680
agttagtatc atcagtgaaa caccatagaa taccctttgt gttccaggtg ggtccctgtt  16740
cctacatgtc tagcctcagg actttttttt ttttaacaca tgcttaaatc aggttgcaca  16800
tcaaaaataa gatcatttct ttttaactaa atagatttga attttattga aaaaaaattt  16860
taaacatctt taagaagctt ataggattta agcaattcct atgtatgtgt actaaaatat  16920
atatatttct atatataata tatattagaa aaaaattgta tttttctttt atttgagtct  16980
actgtcaagg agcaaaacag agaaatgtaa attagcaatt atttataata cttaaaggga  17040
agaaagttgt tcaccttgtt gaatctatta ttgttatttc aattatagtc ccaagacgtg  17100
aagaaatagc tttcctaatg gttatgtgat tgtctcatag tgactacttt cttgaggatg  17160
tagccacggc aaaatgaaat aaaaaaattt aaaaattgtt gcaaatacaa gttatattag  17220
gcttttgtgc attttcaata atgtgctgct atgaactcag aatgatagta tttaaatata  17280
gaaactagtt aaaggaaacg tagtttctat ttgagttata catatctgta aattagaact  17340
tctcctgtta aaggcataat aaagtgctta atacttttgt ttcctcagca ccctctcatt  17400
taattatata attttagttc tgaaagggac ctataccaga tgcctagagg aaatttcaaa  17460
actatgatct aatgaaaaaa tatttaatag ttctccatgc aaatacaaat catatagttt  17520
tccagaaaat acctttgaca ttatacaaag atgattatca cagcattata atagtaaaaa  17580
aatggaaata gcctctttct tctgttctgt tcatagcaca gtgcctcata cgcagtaggt  17640
tattattaca tggtaactgg ctaccccaac tgattaggaa agaagtaaat ttgttttata  17700
aaaatacata ctcattgagg tgcatagaat aattaagaaa ttaaaagaca cttgtaattt  17760
tgaatccagt gaatacccac tgttaatatt tggtatatct ctttctagtc tttttttccc  17820
ttttgcatgt attttcttta agactcccac ccccactgga tcatctctgc atgttctaat  17880
ctgctttttt cacagcagat tctaagcctc tttgaatatc aacacaaact tcaacaactt  17940
catctataga tgccaaataa taaattcatt tttatttact taaccacttc ctttggatgc  18000
ttaggtcatt ctgatgtttt gctattgaaa ccaatgctat actgaacact tctgtcacta  18060
aaactttgca cacactcatg aatagcttct taggataaat ttttagagat ggatttgcta  18120
aatcagagac catttttttaa aattaaaaaa caattattca tatcgtttgg catgtaagac  18180
agtaaatttt ccttttattt tgacaggatt caactggaag ctttgtgctg cctttccggc  18240
aagtcatgta tgctccatat ccccaccacac acatagatgt ggatgtcaat actgtgaagc  18300
agatgccacc ctgtcatgaa catatttata atcagcgtag atacatgaga tccgagctga  18360
cagccttctg gagagccact tcagaagaag acatggctca ggatacgatc atctacactg  18420
acgaaagctt tactcctgat ttgtacgtaa tgctctgcct gctggtactg tagtcaagca  18480
atatgaaatt gtgtctttta cgaataaaaa caaaacagaa gttgcattta aaaagaaaga  18540
aatattacca gcagaattat gcttgaagaa acatttaatc aagcattttt ttcttaaatg  18600
ttcttctttt tccatacaat tgtgtttacc ctaaaatagg taagattaac ccttaaagta  18660
aatatttaac tatttgttta ataaatatat attgagctcc taggcactgt tctaggtacc  18720
gggcttaata gtggccaacc agacagcccc agccccagcc cctacattgt gtatagtcta  18780
ttatgtaaca gttattgaat ggacttatta acaaaaccaa agaagtaatt ctaagtcttt  18840
tttttcttga catatgaata taaaatacag caaaactgtt aaaatatatt aatggaacat  18900
ttttttactt tgcattttat attgttattc acttcttatt ttttttttaaa aaaaaaagcc  18960
tgaacagtaa attcaaaagg aaaagtaatg ataattaatt gttgagcatg gacccaactt  19020
gaaaaaaaaa atgatgatga taaatctata atcctaaaac cctaagtaaa cacttaaaag  19080
atgttctgaa atcaggaaaa gaattatagt atacttttgt gtttctcttt tatcagttga  19140
aaaaaggcac agtagctcat gcctgtaaga acagagcttt gggagtgcaa ggcaggcgga  19200
tcacttgagg ccaggagttc cagaccagcc tgggcaacat agtgaaaccc catctctaca  19260
aaaaataaaa aagaattatt ggaatgtgtt tctgtgtgcc tgtaatccta gctattccga  19320
aagctgaggc aggaggatct tttgagccca ggagtttgag gttacaggga gttatgatgt  19380
gccagtgtac tccagcctgg ggaacaccga gactctgtct tatttaaaaa aaaaaaaaaa  19440
```

-continued

```
aaaatgcttg caataatgcc tggcacatag aaggtaacag taagtgttaa ctgtaataac  19500
ccaggtctaa gtgtgtaagg caatagaaaa attggggcaa ataagcctga cctatgtatc  19560
tacagaatca gtttgagctt aggtaacaga cctgtggagc accagtaatt acacagtaag  19620
tgttaaccaa aagcatagaa taggaatatc ttgttcaagg gaccccccagc cttatacatc  19680
tcaaggtgca gaaagatgac ttaatatagg acccattttt tcctagttct ccagagtttt  19740
tattggttct tgagaaagta gtaggggaat gttttagaaa atgaattggt ccaactgaaa  19800
ttacatgtca gtaagttttt atatattggt aaattttagt agacatgtag aagttttcta  19860
attaatctgt gccttgaaac attttctttt ttcctaaagt gcttagtatt ttttccgttt  19920
tttgattggt tacttgggag cttttttgag gaaatttagt gaactgcaga atgggtttgc  19980
aaccatttgg tatttttgtt ttgtttttta gaggatgtat gtgtatttta acatttctta  20040
atcattttta gccagctatg tttgttttgc tgatttgaca aactacagtt agacagctat  20100
tctcattttg ctgatcatga caaaataata tcctgaattt ttaaattttg catccagctc  20160
taaattttct aaacataaaa ttgtccaaaa aatagtattt tcagccacta gattgtgtgt  20220
taagtctatt gtcacagagt cattttactt ttaagtatat gtttttacat gttaattatg  20280
tttgttattt ttaattttaa ctttttaaaa taattccagt cactgccaat acatgaaaaa  20340
ttggtcactg gaattttttt tttgactttt attttaggtt catgtgtaca tgtgcaggtg  20400
tgttatacag gtaaattgcg tgtcatgagg gtttggtgta caggtgattt cattacccag  20460
gtaataagca tagtacccaa taggtagttt tttgatcctc acccttctcc caccctcaag  20520
taggccctgg tgttgctgtt tccttctttg tgtccatgta tactcagtgt ttagctccca  20580
cttagaagtg agaacatgcg gtagttggtt ttctgttcct ggattagttc acttaggata  20640
atgacctcta gctccatctg gtttttatgg ctgcatagta ttccatggtg tatatgtatc  20700
acattttctt tatccagtct accattgata ggcatttagg ttgattccct gtctttgtta  20760
tcatgaatag tgctgtgatg aacatacaca tgcatgtgtc tttatggtag aaaaatttgt  20820
attcctttag gtacatatag aataatgggg ttgctagggt gaatggtagt tctattttca  20880
gttatttgag aaatcttcaa actgcttttc ataatagcta aactaattta cagtcccgcc  20940
agcagtgtat aagtgttccc ttttctccac aaccttgcca acatctgtga ttttttgact  21000
ttttaataat agccattcct agagaattga tttgcaattc tctattagtg atattaagca  21060
tttttcata tgctttttag ctgtctgtat atattcttct gaaaaatttt catgtccttt  21120
gcccagtttg tagtggggtg ggttgttttt tgcttgttaa ttagttttaa gttccttcca  21180
gattctgcat atccctttgt tggatacatg gtttgcagat atttttctcc cattgtgtag  21240
gttgtctttt actctgttga tagtttcttt tgccatgcag gagctcgtta ggtcccattt  21300
gtgtttgttt ttgttgcagt tgcttttggc gtcttcatca taaaatctgt gccagggcct  21360
atgtccagaa tggtatttcc taggttgtct tccagggttt ttacaatttt agattttacg  21420
tttatgtctt taatccatct tgagttgatt tttgtatatg gcacaaggaa ggggtccagt  21480
ttcactccaa ttcctatggc tagcaattat cccagcacca tttattgaat acggagtcct  21540
ttccccattg cttgtttttt gtcaactttg ttgaagatca gatggttgta agtgtgtggc  21600
tttatttctt ggctctctat tctccattgg tctatgtgtc tgtttttata acagtaccct  21660
gctgttcagg ttcctatagc cttttagtat aaaatcggct aatgtgatgc ctccagcttt  21720
gttctttttg cttaggattg ctttggctat ttgggctcct ttttgggtcc atattaattt  21780
taaaacagtt ttttctggtt ttgtgaagga tatcattggt agtttatagg aatagcattg  21840
aatctgtaga ttgctttggg cagtatggcc attttaacaa tattaattct tcctatctat  21900
gaatatggaa tgtttttcca tgtgtttgtg tcatctcttt atacctgatg tataaagaaa  21960
agctggtatt attcctactc aatctgttcc aaaaaattga ggaggaggaa ctcttcccta  22020
atgaggccag catcattctg ataccaaaac ctggcagaga cacaacagaa aaaagaaaac  22080
ttcaggccaa tatccttgat gaatatagat gcaaaaatcc tcaacaaaat actagcaaac  22140
caaatccagc agcacatcaa aaagctgatc tactttgatc aagtaggctt tatccctggg  22200
atgcaaggtt ggttcaacat acacaaatca ataagtgtga ttcatcacat aaacagagct  22260
aaaaacaaaa accacaagat tatctcaata ggtagagaaa aggttgtcaa taaaatttaa  22320
catcctccat gttaaaaacc ttcagtaggt caggtgtagt gactcacacc tgtaatccca  22380
gcactttggg aggccaaggc gggcatatct cttaagccca ggagttcaag acgagcctag  22440
gcagcatggt gaaaccccat ctctacaaaa aaaaaaaaaa aaaaaaatta gcttggtatg  22500
gtgacatgca cctatagtcc cagctattca ggaggttgag gtgggaggat tgtttgagcc  22560
cgggaggcag aggttggcag cgagctgaga tcatgccacc gcactccagc ctgggcaacg  22620
gagtgagacc ctgtctcaaa aaagaaaaat cacaaacaat cctaaacaaa ctaggcattg  22680
aaggaacatg cctcaaaaaa ataagaacca tctatgacag acccatagcc aatatcttac  22740
caaatgggca aaagctggaa gtattctcct tgagaaccgt aacaagacaa ggatgtccac  22800
tctcaccact ccttttcagc atagttctgg aagtcctagc cagagcaatc aggaaagaga  22860
aagaaagaaa gacattcaga taggaagaga agaagtcaaa ctatttctgt ttgcaggcag  22920
tataattctg tacctagaaa atctcatagt ctctgcccag aaactcctaa atctgttaaa  22980
aatttcagca aagttttggc attctctata ctccaacacc ttccaaagtg agagcaaaat  23040
caagaacaca gtcccattca caatagccgc aaaacgaata aaatacctag gaatccagct  23100
aaccagggag gtgaaagatc tctatgagaa ttacaaaaca ctgctgaaag aaatcagaga  23160
tgacacaaac aaatggaaat gttcttttt aacaccttgc tttatctaat tcacttatga  23220
tgaagatact cattcagtgg aacaggtata ataagtccac tcgattaaat ataagcctta  23280
ttctctttcc agagcccaag aaggggcact atcagtgccc agtcaataat gacgaaatgc  23340
taatattttt cccctttacg gtttctttct tctgtagtgt ggtacactcg tttcttaaga  23400
taaggaaact tgaactacct tcctgtttgc ttctacacat acccattctc tttttttgcc  23460
actctggtca ggtataggat gatccctacc actttcagtt aaaaactcct cctcttacta  23520
aatgttctct taccctctgg cctgagtaga acctagggaa aatggaagag aaaaagatga  23580
aagggaggtg gggcctggga agggaataag tagtcctgtt tgtttgtgtg tttgctttag  23640
cacctgctat atcctaggtg ctgtgttagg cacacattat tttaagtggc cattatatta  23700
ctactactca ctctggtcgt tgccaaggta ggtagtactt tcttggatag ttggttcatg  23760
ttacttacag atggtgggct tgttgaggca aacccagtgg ataatcatcg gagtgtgttc  23820
tctaatctca ctcaaatttt tcttcacatt ttttggtttg ttttggtttt tgatggtagt  23880
ggcttatttt tgttgctggt ttgttttttg tttttttttg agatggcaag aattggtagt  23940
tttatttatt aattgcctaa gggtctctac tttttttaaa agatgagagt agtaaaatag  24000
attgatagat acatacatac ccttactggg gactgcttat attctttaga gaaaaaatta  24060
catattagcc tgacaaacac cagtaaaatg taaatatatc cttgagtaaa taaatgaatg  24120
tatattttgt gtctccaaat atatatatct atattcttac aaatgtgttt atatgtaata  24180
```

-continued

```
tcaatttata agaacttaaa atgttggctc aagtgaggga ttgtggaagg tagcattata  24240
tggccatttc aacatttgaa cttttttctt ttcttcattt tcttcttttc ttcaggaata  24300
tttttcaaga tgtcttacac agagacactc tagtgaaagc cttcctggat caggtaaatg  24360
ttgaacttga gattgtcaga gtgaatgata tgacatgttt tcttttttaa tatatcctac  24420
aatgcctgtt ctatatattt atattcccct ggatcatgcc ccagagttct gctcagcaat  24480
tgcagttaag ttagttacac tacagttctc agaagagtct gtgagggcat gtcaagtgca  24540
tcattacatt ggttgcctct tgtcctagat ttatgcttcg ggaattcaga cctttgttta  24600
caatataata aatattattg ctatctttta aagatataat aataagatat aaagttgacc  24660
acaactactg tttttgaaa catagaattc ctggtttaca tgtatcaaag tgaaatctga  24720
cttagctttt acagatataa tatatacata tatatatcct gcaatgcttg tactatatat  24780
gtagtacaag tatatatata tgtttgtgtg tgtatatata tatagtacga gcatatatac  24840
atattaccag cattgtagga tatatatatg tttatatatt aaaaaaaagt tataaactta  24900
aaaccctatt atgttatgta gagtatatgt tatatatgat atgtaaaata tataacatat  24960
actctatgat agagtgtaat atatttttta tatatatttt aacatttata aaatgataga  25020
attaagaatt gagtcctaat ctgttttatt aggtgctttt tgtagtgtct ggtctttcta  25080
aagtgtctaa atgattttc ctttgactt attaatgggg aagagcctgt atattaacaa  25140
ttaagagtgc agcattccat acgtcaaaca acaaacattt taattcaagc attaacctat  25200
aacaagtaag ttttttttt tttttgaga aagggaggtt gtttatttgc ctgaaatgac  25260
tcaaaaatat ttttgaaaca tagtgtactt atttaaataa catctttatt gtttcattct  25320
tttaaaaaat atctacttaa ttacacagtt gaaggaaatc gtagattata tggaacttat  25380
ttcttaatat attacagttt gttataataa cattctgggg atcaggccag gaaactgtgt  25440
catagataaa gctttgaaat aatgagatcc ttatgtttac tagaaatttt ggattgagat  25500
ctatgaggtc tgtgacatat tgcgaagttc aaggaaaatt cgtaggcctg gaatttcatg  25560
cttctcaagc tgacataaaa tccctcccac tctccacctc atcatatgca cacattctac  25620
tcctacccac ccactccacc ccctgcaaaa gtacaggtat atgaatgtct caaaaccata  25680
ggctcatctt ctaggagctt caatgttatt tgaagatttg ggcagaaaaa attaagtaat  25740
acgaaataac ttatgtatga gttttaaaag tgaagtaaac atggatgtat tctgaagtag  25800
aatgcaaaat ttgaatgcat ttttaaagat aaattagaaa acttctaaaa actgtcagat  25860
tgtctgggcc tggtggctta tgcctgtaat cccagcactt tgggagtccg aggtgggtgg  25920
atcacaaggt caggagatcg agaccatcct gccaacatgg tgaaaccccg tctctactaa  25980
gtatacaaaa attagctggg cgtggcagcg tgtgcctgta atcccagcta cctgggaggc  26040
tgaggcagga gaatcgcttg aacccaggag gtgtaggttg cagtgagtca agatcgcgcc  26100
actgcacttt agcctggtga cagagctaga ctccgtctca aaaaaaaaaa aaaatatcag  26160
attgttccta cacctagtgc ttctatacca cactcctgtt agggggcatc agtggaaatg  26220
gttaaggaga tgtttagtgt gtattgtctg ccaagcactg tcaacactgt catagaaact  26280
tctgtacgag tagaatgtga gcaaattatg tgttgaaatg gttcctctcc ctgcaggtct  26340
ttcagctgaa acctggctta tctctcagaa gtactttcct tgcacagttt ctacttgtcc  26400
ttcacagaaa agccttgaca ctaataaaat atatagaaga cgatacgtga gtaaaactcc  26460
tacacggaag aaaaaccttt gtacattgtt tttttgtttt gtttcctttg tacatttttct  26520
atatcataat ttttgcgctt cttttttttt tttttttttt ttttttttcca ttatttttag  26580
gcagaaggga aaaaagccct ttaaatctct tcggaacctg aagatagacc ttgatttaac  26640
agcagagggc gatcttaaca taataatggc tctggctgag aaaattaaac caggcctaca  26700
ctcttttatc tttggaagac ctttctacac tagtgtgcaa gaacgagatg ttctaatgac  26760
tttttaaatg tgtaacttaa taagcctatt ccatcacaat catgatcgct ggtaaagtag  26820
ctcagtggtg tggggaaacg ttcccctgga tcatactcca gaattctgct ctcagcaatt  26880
gcagttaagt aagttacact acagttctca caagagcctg tgaggggatg tcaggtgcat  26940
cattacattg ggtgtctctt ttcctagatt tatgcttttg ggatacagac ctatgtttac  27000
aatataataa atattattgc tatcttttaa agatataata ataggatgta aacttgacca  27060
caactactgt tttttgaaa tacatgattc atggtttaca tgtgtcaagg tgaaatctga  27120
gttggctttt acagatagtt gactttctat cttttggcat tctttggtgt gtagaattac  27180
tgtaatactt ctgcaatcaa ctgaaaacta gagcctttaa atgatttcaa ttccacagaa  27240
agaaagtgag cttgaacata ggatgagctt tagaaagaaa attgatcaag cagatgttta  27300
attggaattg attattagat cctactttgt ggatttagtc cctgggattc agtctgtaga  27360
aatgtctaat agttctctat agtccttgtt cctggtgaac cacagttagg gtgttttgtt  27420
tattttattg ttcttgctat tgttgatatt ctatgtagtt gagctctgta aaaggaaatt  27480
gtattttatg ttttagtaat tgttgccaac tttttaaatt aattttcatt atttttgagc  27540
caaattgaaa tgtgcacctc ctgtgccttt tttctcctta gaaaatctaa ttacttggaa  27600
caagttcaga tttcactggt cagtcatttt catcttgttt tcttcttgct aagtcttacc  27660
atgtacctgc tttggcaatc attgcaactc tgagattata aaatgcctta gagaatatac  27720
taactaataa gatctttttt tcagaaacag aaaatagttc cttgagtact tccttcttgc  27780
atttctgcct atgtttttga agttgttgct gtttgcctgc aataggctat aaggaatagc  27840
aggagaaatt ttactgaagt gctgttttcc taggtgctac tttggcagag ctaagttatc  27900
ttttgttttc ttaatgcgtt tggaccattt tgctggctat aaaataactg attaatataa  27960
ttctaacaca atgttgacat tgtagttaca caaacacaaa taaatatttt atttaaaatt  28020
ctggaagtaa tataaaaggg aaaatatatt tataagaaag ggataaaggt aatagagccc  28080
ttctgccccc cacccaccaa atttacacaa caaaatgaca tgttcgaatg tgaaaggtca  28140
taatagcttt cccatcatga atcagaaaga tgtggacagc ttgatgtttt agacaaccac  28200
tgaactagat gactgttgta ctgtagctca gtcatttaaa aaatatataa atactacctt  28260
gtagtgtccc atactgtgtt ttttacatgg tagattctta tttaagtgct aactggttat  28320
tttctttggc tggtttattg tactgttata cagaatgtaa gttgtacagt gaaataagtt  28380
attaaagcat gtgtaaacat tgttatatat cttttctcct aaatggagaa ttttgaataa  28440
aatatatttg aaattttgcc tctttcagtt gttcattcag aaaaaaatac tatgatattt  28500
gaagactgat cagcttctgt tcagctgaca gtcatgctgg atctaaactt tttttaaaat  28560
taattttgtc ttttcaaaga aaaaatattt aaagaagctt tataatataa tcttatgtta  28620
aaaaaacttt ctgcttaact ctctggattt cattttgatt tttcaaatta tatattaata  28680
tttcaaatgt aaaatactat ttagataaat tgtttttaaa cattcttatt attataatat  28740
taatataacc taaactgaag ttattcatcc caggtatcta atacatgtat ccaaagtaaa  28800
aatccaagga atctgaacac tttcatctgc aaagctagga ataggtttga catttcact  28860
ccaagaaaaa gtttttttt gaaaatagaa tagttgggat gagaggtttc tttaaaagaa  28920
```

-continued

```
gactaactga tcacattact atgattctca aagaagaaac caaaacttca tataatacta  28980
taaagtaaat ataaaatagt tccttctata gtatatttct ataatgctac agtttaaaca  29040
gatcactctt atataatact attttgattt tgatgtagaa ttgcacaaat tgatatttct  29100
cctatgatct gcagggtata gcttaaagta acaaaaacag tcaaccacct ccatttaaca  29160
cacagtaaca ctatgggact agttttatta cttccatttt acaaatgagg aaactaaagc  29220
ttaaagatgt gtaatacacc gcccaaggtc acacagctgg taaaggtgga tttcatccca  29280
gacagttaca gtcattgcca tgggcacagc tcctaactta gtaactccat gtaactggta  29340
ctcagtgtag ctgaattgaa aggagagtaa ggaagcaggt tttacaggtc tacttgcact  29400
attcagagcc cgagtgtgaa tccctgctgt gctgcttgga gaagttactt aacctatgca  29460
aggttcattt tgtaaatatt ggaaatggag tgataatacg tacttcacca gaggatttaa  29520
tgagacctta tacgatcctt agttcagtac ctgactagtg cttcataaat gctttttcat  29580
ccaatctgac aatctccagc ttgtaattgg ggcatttaga acatttaata tgattattgg  29640
catggtaggt taaagctgtc atcttgctgt tttctatttg ttctttttgt tttctcctta  29700
cttttggatt tttttattct actatgtctt ttctattgtc ttattaacta tactctttga  29760
tttattttag tggttgtttt agggttatac ctctttctaa tttaccagtt tataaccagt  29820
ttatatacta cttgacatat agcttaagaa acttactgtt gttgtctttt tgctgttatg  29880
gtcttaacgt ttttatttct acaaacatta taaactccac actttattgt tttttaattt  29940
tacttataca gtcaattatc ttttaaagat atttaaatat aaacattcaa aacaccccaa  30000
t                                                                 30001

SEQ ID NO: 3            moltype = RNA  length = 1031
FEATURE                 Location/Qualifiers
source                  1..1031
                        mol_type = mRNA
                        organism = Homo sapiens
SEQUENCE: 3
attcccggga tacgtaacct acggtgtccc gctaggaaag agaggtgcgt caaacagcga  60
caagttccgc ccacgtaaaa gatgacgctt ggtgtgtcag ccgtccctgc tgcccggttg  120
cttctctttt gggggcgggg tctagcaaga gcaggtgtgg gtttaggaga tatctccgga  180
gcatttggat aatgtgacag ttggaatgca gtgatgtcga ctctttgccc accgccatct  240
ccagctgttg ccaagacaga gattgcttta agtggcaaat cacctttatt agcagctact  300
tttgcttact gggacaatat tcttggtcct agagtaaggc acatttgggc tccaaagaca  360
gaacaggtac ttctcagtga tggagaaata acttttcttg ccaaccacac tctaaatgga  420
gaaatccttc gaaatgcaga gagtggtgct atagatgtaa agtttttgt cttgtctgaa  480
aagggagtga ttattgtttc attaatcttt gatggaaact ggaatgggga tcgcagcaca  540
tatggactat caattatact tccacagaca gaacttagtt tctacctccc acttcataga  600
gtgtgtgttg atagattaac acatataatc cggaaaggaa gaatatggat gcataaggaa  660
agacaagaaa aatgtccaga agattatctt agaaggcaca gagagaatgg aagatcaggg  720
tcagagtatt attccaatgc ttactggaga agtgattcct gtaatggaaa ctgctttcct  780
ctatgaaatt cccccgggtt cctggaggaa atagatatag gctgatacag ttacccaatg  840
atggatgaat attgggggac cgcctggtca ttgaaaggct ttcttttctc caggaaagaa  900
atttttttcc ttttccataa aaagcttggg aatggaagac aacaattccc attctttttt  960
tgcgttccac ccctatgtga caacagaaat tttggggaa acaacaacga aaaaatttta  1020
tcccgcgcgc a                                                      1031

SEQ ID NO: 4            moltype = RNA  length = 3244
FEATURE                 Location/Qualifiers
source                  1..3244
                        mol_type = mRNA
                        organism = Homo sapiens
SEQUENCE: 4
gggcggggct gcggttgcgg tgcctgcgcc cgcggcggcg gaggcgcagg cggtggcgag  60
tggatatctc cggagcattt ggataatgtg acagttggaa tgcagtgatg tcgactcttt  120
gcccaccgcc atctccagct gttgccaaga cagagattgc tttaagtggc aaatcacctt  180
tattagcagc tacttttgct tactgggaca atattcttgg tcctagagta aggcacattt  240
gggctccaaa gacagaacag gtacttctca gtgatggaga aataactttt cttgccaacc  300
acactctaaa tggagaaatc cttcgaaatg cagagagtgg tgctatagat gtaaagtttt  360
ttgtcttgtc tgaaaaggga gtgattattg tttcattaat ctttgatgga aactggaatg  420
gggatcgcag cacatatgga ctatcaatta tacttccaca gacagaactt agtttctacc  480
tcccacttca tagagtgtgt gttgatagat taacacatat aatccggaaa ggaagaatat  540
ggatgcataa ggaaagacaa gaaaatgtcc agaagattat cttagaaggc acagagagaa  600
tggaagatca gggtcagagt attattccaa tgcttactgg agaagtgatt cctgtaatgg  660
aactgctttc atctatgaaa tcacacagtg ttcctgaaga aatagatata gctgatacag  720
tactcaatga tgatgatatt ggtgacagct gtcatgaagg ctttcttctc aatgccatca  780
gctcacactt gcaaacctgt ggctgttccg ttgtagtagg tagcagtgca gagaaagtaa  840
ataagatagt cagaacatta tgcctttttc tgactccagc agagagaaaa tgctccaggt  900
tatgtgaagc agaatcatca tttaaatatg agtcagggct ctttgtacaa ggcctgctaa  960
aggattcaac tggaagcttt gtgctgcctt tccggcaagt catgtatgct ccatatccca  1020
ccacacacat agatgtggat gtcaatactg tgaagcagat gccaccctgt catgaacata  1080
tttataatca gcgtagatac atgagatccg agctgacagc cttctggaga gccacttcag  1140
aagaagacat ggctcaggat acgatcatct acactgacga aagctttact cctgatttga  1200
atatttttca agatgtctta cacagagaca ctctagtgaa agccttcctg gatcaggtct  1260
ttcagctgaa acctggctta tctctcagaa gtactttcct tgcacagttt ctacttgtcc  1320
ttcacagaaa agccttgaca ctaataaaat atatagaaga cgatacgcag aagggaaaaa  1380
agccctttaa atctcttcgg aacctgaaga tagaccttga tttaacagca gagggcgatc  1440
ttaacataat aatggctctg gctgagaaaa ttaaaccagg cctacactct tttatctttg  1500
gaagaccttt ctacactagt gtgcaagaac gagatgttct aatgactttt taaatgtgta  1560
acttaataag cctattccat cacaatcatg atcgctggta aagtagctca gtggtgtggg  1620
gaaacgttcc cctggatcat actccagaat tctgctctca gcaattgcag ttaagtaagt  1680
```

-continued

```
tacactacag ttctcacaag agcctgtgag ggatgtcag gtgcatcatt acattgggtg  1740
tctcttttcc tagatttatg cttttgggat acagacctat gtttacaata taataaatat  1800
tattgctatc ttttaaagat ataataatag gatgtaaact tgaccacaac tactgttttt  1860
ttgaaataca tgattcatgg tttacatgtg tcaaggtgaa atctgagttg gcttttacag  1920
atagttgact ttctatcttt tggcattctt tggtgtgtag aattactgta atacttctgc  1980
aatcaactga aaactagagc ctttaaatga tttcaattcc acagaaagaa agtgagcttg  2040
aacataggat gagctttaga aagaaaattg atcaagcaga tgtttaattg gaattgatta  2100
ttagatccta ctttgtggat ttagtccctg ggattcagtc tgtagaaatg tctaatagtt  2160
ctctatagtc cttgttcctg gtgaaccaca gttagggtgt tttgtttatt ttattgttct  2220
tgctattgtt gatattctat gtagttgagc tctgtaaaag gaaattgtat tttatgtttt  2280
agtaattgtt gccaactttt taaattaatt ttcattattt ttgagccaaa ttgaaatgtg  2340
cacctcctgt gcctttttc tccttagaaa atctaattac ttggaacaag ttcagatttc  2400
actggtcagt cattttcatc ttgttttctt cttgctaagt cttaccatgt acctgctttg  2460
gcaatcattg caactctgag attataaaat gccttagaga atatactaac taataagatc  2520
ttttttcag aaacagaaaa tagttccttg agtacttcct tcttgcattt ctgcctatgt  2580
ttttgaagtt gttgctgttt gcctgcaata ggctataagg aatagcagga gaaattttac  2640
tgaagtgctg ttttcctagg tgctactttg gcagagctaa gttatctttt gttttcttaa  2700
tgcgtttgga ccattttgct ggctataaaa taactgatta atataattct aacacaatgt  2760
tgacattgta gttacacaaa cacaaataaa tattttattt aaaattctgg aagtaatata  2820
aaagggaaaa tatatttata agaaagggat aaaggtaata gagcccttct gccccccacc  2880
caccaaattt acacaacaaa atgacatgtt cgaatgtgaa aggtcataat agctttccca  2940
tcatgaatca gaaagatgtg gacagcttga tgttttagac aaccactgaa ctagatgact  3000
gttgtactgt agctcagtca tttaaaaaat atataaatac taccttgtag tgtcccatac  3060
tgtgtttttt acatggtaga ttcttattta agtgctaact ggttattttc tttggctggt  3120
ttattgtact gttatacaga atgtaagttg tacagtgaaa taagttatta aagcatgtgt  3180
aaacattgtt atatatcttt tctcctaaat ggagaatttt gaataaaata tatttgaaat  3240
tttg                                                             3244

SEQ ID NO: 5           moltype = RNA  length = 761
FEATURE                Location/Qualifiers
source                 1..761
                       mol_type = mRNA
                       organism = Homo sapiens
SEQUENCE: 5
cacgaggctt tgatatttct tacaacgaat ttcatgtgta gacccactaa acagaagcta  60
taaaagttgc atggtcaaat aagtctgaga aagtctgcag atgatataat tcacctgaag  120
agtcacagta tgtagccaaa tgttaaaggt tttgagatgc catacagtaa atttaccaag  180
cattttctaa atttatttga ccacagaatc cctattttaa gcaacaactg ttacatccca  240
tggattccag gtgactaaag aatacttatt tcttaggata tgttttattg ataataacaa  300
ttaaaatttc agatatcttt cataagcaaa tcagtggtct ttttacttca tgttttaatg  360
ctaaaatatt ttcttttata gatagtcaga acattatgcc tttttctgac tccagcagag  420
agaaaatgct ccaggttatg tgaagcagaa tcatcattta aatatgagtc agggctcttt  480
gtacaaggcc tgctaaagga ttcaactgga agctttgtgc tgcctttccg gcaagtcatg  540
tatgctccat atcccaccac acacatagat gtggatgtca atactgtgaa gcagatgcca  600
ccctgtcatg aacatattta taatcagcgt agatacatga gatccgagct gacagccttc  660
tggagagcca cttcagaaga agacatggct cangatacga tcatctacac tgacgaaagc  720
tntactcctg atttgaatat ttttcaagat gtcttacaca g                     761

SEQ ID NO: 6           moltype = RNA  length = 1901
FEATURE                Location/Qualifiers
source                 1..1901
                       mol_type = mRNA
                       organism = Homo sapiens
SEQUENCE: 6
acgtaaccta cggtgtcccg ctaggaaaga gaggtgcgtc aaacagcgac aagttccgcc  60
cacgtaaaag atgacgcttg atatctccgg agcatttgga taatgtgaca gttggaatgc  120
agtgatgtcg actctttgcc caccgccatc tccagctgtt gccaagacag agattgcttt  180
aagtggcaaa tcacctttat tagcagctac ttttgcttac tgggacaata ttcttggtcc  240
tagagtaagg cacatttggg ctccaaagac agaacaggta cttctcagtg atggagaaat  300
aacttttctt gccaaccaca ctctaaatgg agaaatcctt cgaaatgcag agagtggtgc  360
tatagatgta aagtttttg tcttgtctga aaagggagtg attattgttt cattaatctt  420
tgatggaaac tggaatgggg atcgcagcac atatggacta tcaattatac ttccacagac  480
agaacttagt ttctacctcc cacttcatag agtgtgtgtt gatagattaa cacatataat  540
ccggaaagga agaatatgga tgcataagga aagacaagaa aatgtccaga agattatctt  600
agaaggcaca gagagaatgg aagatcaggg tcagagtatt attccaatgc ttactggaga  660
agtgattcct gtaatggaac tgctttcatc tatgaaatca cacagtgttc ctgaagaaat  720
agatatagct gatacagtac tcaatgatga tgatattggt gacagctgtc atgaaggctt  780
tcttctcaag taagaatttt tcttttcata aaagctggat gaagcagata ccatcttatg  840
ctcacctatg acaagatttg gaagaaagaa aataacagac tgtctactta gattgttcta  900
gggacattac gtatttgaac tgttgcttaa atttgtgtta tttttcactc attatatttc  960
tatatatatt tggtgttatt ccatttgcta tttaaagaaa ccgagtttcc atcccagaca  1020
agaaatcatg gccccttgct tgattctggt ttcttgtttt acttctcatt aaagctaaca  1080
gaatcctttc atattaagtt gtactgtaga tgaacttaag ttatttaggc gtagaacaaa  1140
attattcata tttatactga tctttttcca tccagcagtg gagtttagta cttaagagtt  1200
tgtgccctta aaccagactc cctggattaa tgctgtgtac ccgtgggcaa ggtgcctgaa  1260
ttctctatac acctatttcc tcatctgtaa aatggcaata atagtaatag tacctaatgt  1320
gtagggttgt tataagcatt gagtaagata aataatataa agcacttaga acagtgcctg  1380
gaacataaaa acacttaata atagctcata gctaacattt cctatttaca tttcttctag  1440
aaatagccag tatttgttga gtgcctacat gttagttcct ttactagttg ctttacatgt  1500
```

-continued

```
attatcttat attctgtttt aaagtttctt cacagttaca gattttcatg aaattttact  1560
tttaataaaa gagaagtaaa agtataaagt attcactttt atgttcacag tcttttcctt  1620
taggctcatg atggagtatc agaggcatga gtgtgtttaa cctaagagcc ttaatggctt  1680
gaatcagaag cactttagtc ctgtatctgt tcagtgtcag cctttcatac atcattttaa  1740
atcccatttg actttaagta agtcacttaa tctctctaca tgtcaatttc ttcagctata  1800
aaatgatggt atttcaataa ataaatacat taattaaatg atattatact gactaattgg  1860
gctgttttaa ggcaaaaaaa aaaaaaaaaa aaaaaaaaaa a                      1901

SEQ ID NO: 7           moltype = RNA  length = 562
FEATURE                Location/Qualifiers
source                 1..562
                       mol_type = mRNA
                       organism = Homo sapiens
SEQUENCE: 7
agacgtaacc tacggtgtcc cgctaggaaa gagagatatc tccggagcat ttggataatg  60
tgacagttgg aatgcagtga tgtcgactct ttgcccaccg ccatctccag ctgttgccaa  120
gacagagatt gctttaagtg gcaaatcacc tttattagca gctacntttt gcttactggg  180
acaatattct tggtcctaga gtaaggcaca tttgggctcc aaagacagaa caggtacttc  240
tcagtgatgg agaaataact tttcttgcca accacactct aaatggagaa atccttcgaa  300
atgcagagag tggtgctata gatgtaaagt tttttgtctt gtctgaaaag ggagtgatta  360
ttgtttcatt aatctttgat ggaaactgga atggggatcg cagcacatat ggactatcaa  420
ttatacttcc acagacagaa cttagtttct acctcccact tcatagagtg tgtgttgata  480
gattaacaca tataatccgg aaaggaagaa tatggatgca taaggaaaga caagaaaatg  540
tccagaagat tatcttagaa gg                                            562

SEQ ID NO: 8           moltype = RNA  length = 798
FEATURE                Location/Qualifiers
source                 1..798
                       mol_type = mRNA
                       organism = Homo sapiens
SEQUENCE: 8
gggctctctt ttgggggcgg ggtctagcaa gagcagatat ctccggagca tttggataat  60
gtgacagttg gaatgcagtg atgtcgactc tttgcccacc gccatctcca gctgttgcca  120
agacagagat tgctttaagt ggcaaatcac ctttattagc agctactttt gcttactggg  180
acaatattct tggtcctaga gtaaggcaca tttgggctcc aaagacagaa caggtacttc  240
tcagtgatgg agaaataact tttcttgcca accacactct aaatggagaa atccttcgaa  300
atgcagagag tggtgctata gatgtaaagt tttttgtctt gtctgaaaag ggagtgatta  360
ttgtttcatt aatctttgat ggaaactgga atggggatcg cagcacatat ggactatcaa  420
ttatacttcc acagacagaa cttagtttct acctcccact tcatagagtg tgtgttgata  480
gattaacaca tataatccgg aaaggaagaa tatggatgca taaggaaaga caagaaaatg  540
tccagaagat tatcttagaa ggcacagaga gaatggaaga tcagggtcag agtattattc  600
caatgcttac tggagaagtg attcctgtaa tgggactgct ttcatctatg aaatcacaca  660
gtgttcctga agaaatagat atagctgata cagtactcca tgatgatgat atttggtgac  720
agctgtcatg aaaggctttc ttctcaagta ggaatttttt cttttcataa aagctgggat  780
gaagccagat tcccatct                                                 798

SEQ ID NO: 9           moltype = RNA  length = 169
FEATURE                Location/Qualifiers
source                 1..169
                       mol_type = mRNA
                       organism = Homo sapiens
SEQUENCE: 9
aaacagcgac aagttccgcc cacgtaaaag atgatgcttg gtgtgtcagc cgtccctgct  60
gcccggttgc ttctcttttg ggggcggggt ctagcaagag cagatatctc cggagcattt  120
ggataatgtg acagttggaa tgcggtgatg tcgactcttt gcccaccgc              169

SEQ ID NO: 10          moltype = RNA  length = 176
FEATURE                Location/Qualifiers
source                 1..176
                       mol_type = mRNA
                       organism = Homo sapiens
SEQUENCE: 10
aaaacgtcat cgcacataga aaacagacag acgtaaccta cggtgtcccg ctaggaaaga  60
gaggtgcgtc aaacagcgac aagttccgcc cacgtaaaag atgacgcttg atatctccgg  120
agcatttgga taatgtgaca gttggaatgc agtgatgtcg actctttgcc caccgc       176

SEQ ID NO: 11          moltype = DNA  length = 38001
FEATURE                Location/Qualifiers
source                 1..38001
                       mol_type = genomic DNA
                       organism = Mus musculus
SEQUENCE: 11
caaacacaca cacacacaca cacacacaca cacacacaca cacacacaca cacacactgg  60
catatcaagt ctctgttagg ctaggcgcat cctctcccac tgaggtcaga caagactgcc  120
cagctagaag aacatatccc acggacaggc aacagctttt gggacagcca cgctccagtt  180
gtttgggact cataaaagac taaactcaca cctgctacaa aagtgcaggg aggcctaggt  240
ccagcctgtg tgtgctcttt gcttagtggt gtctctgaga gccctaagga tcaaagtttg  300
ttgactctgt tggtcttcct gtggagttcc tatccccttc gtccccctcc ccaccctgca  360
atctttccct caactcttct ttaggcctgg tggtggtggt gtggtggcat ggaggaggtg  420
```

-continued

```
gtggaggggg tgggggtctt taatcccggt tcttgtgaga ccgaagcagg gacgatttcg  480
gagctctgtg agtttgaggc cagcctggtc tatagatcta gttccaggac agtcagagct  540
acatagagaa accctgcccc gaggggggggg gggcgcgggg aatggttaaa gattattgca  600
ggacccagct gatctgtgga agaggtaacg ggtgtttatg tttttcgaaa ctcattgaac  660
aatgcacttc aattgtgcgc actttagaaa tataaagcca ccacgcgaaa agctgcgccc  720
caacttaaag gcaatttcca aggtacttct gggtccttgc ggttcagtgg ctgtctaggt  780
tcagaaacga aactggatcc ccgccccgcc cccccgcccc ccccctcccc agcgccctga  840
ggcagtttcg atttcctatg gccagccggc taggcagctt tttcatcggg actccttgga  900
aagtccccac ttcgttcatc tctggcggat ttgcgggagc cagggcgctc atcgatcgcc  960
tggagccaca gaatgacagc ggagcagcgg cagaatctgc aagcattcag agactatatc  1020
aagaagattc tggaccccac ctacatcctc agctacatga gttcctggct cgaggatggt  1080
gagtggtccc caactggggc tctcaggctc tccaccttag cgaggggaaa acatcactca  1140
gatcagaaac aattgaaggc tctgcccccc cccctccccc gcgctgtcct taagttaatt  1200
tgtgtaaccc ggtgtatgtg agactcccag gccatattag agtagacagc atagggattt  1260
gatggtcagg aacaaaattc ctgcaagctg tagtaacttg cataaggatg ccactctttt  1320
ctttctttca atgctgggga aatagtttgt ttctcttatt tacaccttct agactgctgt  1380
gtgcctccct ttgtcctgtc atgagaaact gagaaatcag aatgcgcccg cccctcctta  1440
gattcctgta cagagcaaag agcaaggctt tgggctcggg ccaaaggtgg aggtgggggc  1500
cgcaggaagc aagaggactg actgacacgc acatttctgt caaaggatgt tgctcacagg  1560
aagtccgtgg aagaaaactt tctccagact ccgtgtgttc agagtttaac acagttgttc  1620
atatctagct ttggggattt gattggtgga taatagactc tttgtaaatt gcactgggtg  1680
tttccacctg agcaaacaga cctccccacc tcacccccac ccccagggag aagggagagg  1740
gcgtttgaag ggtgaccga gggcgtgcgg cagctacttt tcattttgcc agttaaagcc  1800
tagatgtctt tcctggcgtt ggacgacggt ggcaactgca ggttaattct gactctcttg  1860
agttccgaag cctaacaggc tatgcagaga ggagtaaaag agcactaccc agggctaccc  1920
acatcccggt tgtgttagag agaagcagca aaaaagccct aatgattggg ggcggggtct  1980
gaggagagga aacccaccca agaggtttct taacaccagg gtcacttgcc tttcaatcct  2040
ttaatctgat ctttagtcat ttacattagc atacaaagta actagtttca atactgaaac  2100
aaagtaacta gtttgttcag ccattcctgc cattgctctt tgttcttatt taattgcctc  2160
ttctgtggct cttccacccc ctttacctgt ccctctctgg atgccctccc ccccaaatgg  2220
taccccgttc tgctttctta taacatgagg ttcatcacac tccctccctc cctccctccc  2280
ccatttaaag tatcatcctt tcctctcagg gtgcctgttt tagtttcatg aattttaggg  2340
ttttggtttt ttgtctgttt agttatgaga ttttttttaaa aatgtggatt atgttgaatt  2400
tgtagattgt tcttggtgct agaggccttt ttatagtatt atttccaccc atcttgggag  2460
atctttctga aatcttccag tgtcttcaag aatttttttt tcccactgcc ttagaagttt  2520
gcattgtagc tatcgttcac ctctttggtt agggtttgtt gttatttgtt tgtttgaggc  2580
tattgtgaat agaactccct ccttccccca tatctttctg ggccaggttg ttcttagtat  2640
gtaagtaagc tactggtttc tgtatgttta tttagaaccc tgcctcttgg ttgacttttt  2700
atgagggctg agagtttgtg gtagtctttg gggggtcttt ataggattat ataagaatca  2760
tttgactcat tcctttccta tttgtctaac ttttgtttgt ttgtttgttt gttttttttga  2820
gacagggttt ctctgtatag ccctggcagt cctggaactc actttgtaga ccaggctggc  2880
ctcgaactca gaaatctgcc tgcctctgcc tcccgagtgc tgggattaaa ggcgtgcacc  2940
accacacccg gccatcattt ccaagttaaa gatttgatct acattagacg ccgccacgca  3000
gaaaaccttg agacttggtg gaaaggccaa aggccattaa aataaatttt cttttttctt  3060
tcttccattc tttcctttat tccttccttc ctttcttttt gtttcttttc ttttcttttt  3120
cctttttcct gagacagggt ttctctgtat agccctggca tcctggaact cactctgtag  3180
accaggctgg cctcgaactc agaaatccac cagcctttgc ctcccaagtg ttgggattaa  3240
aggcattcgc caccactgcc caaatatttt atttatttat ttatttattt atttttatat  3300
atgtgatgag tacactggaa attccatcaa aaagagcagg tttgactggt gtcactagat  3360
ttactattga tagggatccc taaaggagag ctaaggtaaa gggctctccc tctcctaggt  3420
cttctgcata ccttccttga gtgttctggg ccagatctcc taagctctaa gaatgtgctg  3480
aaaacacact gggaactggc tccctccttg ggaatttgta ctccctctgc tgtgggaaac  3540
ttggatataa gaggctacag gaggacagtg agttataccc caggcacaga gttagcgtgt  3600
acattcaaaa cgcataccat tttgaaagta gcagctgcta gcatttcctg tcacctggtc  3660
aacctggtct ctttagctgc ccccacccctt ccactttttct gctgtgtttc ttttactctc  3720
ttagcaaaaa ttggaatgaa agaccacaaa tgtatttgta attcaaaatg cttgctgcat  3780
cagctatact cgttactgtt gccatagggc gttcattccc acccaccccc aaccccttag  3840
tccagcagtt gcttcagagt tttgaagaag aggaggaagc ctttcttctt ccatgtgaca  3900
ccctccactg cgacttctgc ttactgtggg gaacttgagt ggaggacggg agtgtgcata  3960
gatgaaagag tggaggacgg gagtgtgcat agatgaagga gtggaggacg ggagtgtgca  4020
tacatgaagg agtggaggac gggagtgtgc atacatgaag gagtggagga cgggagtgtg  4080
catacatgaa ggagtggagg acgggagtgt gcatacatga aggagtggag gatgggagtg  4140
tgcatacatg aaggagtgga ggacgggagt gtgcatacat gaaggagtgg aggacgggag  4200
tgtgcataca tgaaggagag gaggacggga gtgtgcatag atgaaggaga ggaggacggg  4260
agtgtgcata gatgaaggag aggaggacgg gagtgtgcat agatgaagga gaggaggacg  4320
ggagtgtgca tagatgaagg agaggaggac gggagtgtgc atagatgaag gagtggagga  4380
cgggagtgtg catacatgaa ggagtggagg acgggagtgt gcatacatga aggagtggag  4440
gacgggagtg tgcatacatg aaggagtgga ggacgggagt gtgcatacat gaaggagtgg  4500
aggacgggag tgtgcataca tgaaggagag gaggacggga gtgtgcatag atgaaggaga  4560
ggaggacggg agtgtgcata gatgaaggag aggaggacgg gagtgtgcat agatgaagga  4620
gaggaggacg ggagtgtgca tacatgaagg aaaggaggac gggagtgtgc atagatgaag  4680
gagtggagga cgggagtgtg catacatgaa ggagtggagg acgggagtgt gcatacatga  4740
aggagtggag gacgggagtg tgcatatgaa ggagtggagg acgggagtgt gcatacatga  4800
aggagtggag gacgggagtg tgcatagatg aaggagagga ggacgggagt gtgcatagat  4860
gaaggagagg aggacgggag agtgcataga tgaaggagtg gaggacggga gtgtgcatac  4920
atgaaggagt ggaggacggg agtgtgcata catgaaggag tggaggacgg gagtgtgcat  4980
agatgaagga gaggaggacg ggagtgtgca tagatgaagg agaggaggac gggagagtgc  5040
atagatgaag gagtggagga cgggagtgtg catagatgaa ggagtggagg acgagagtgt  5100
gcatacatga aggagtggag gacgggagtg tgcgaggatg gatgagtgga gtctgctgcc  5160
```

-continued

```
tctcaaaggt cttctggttc catgagttgt tatgactccc agacccacat gggaaggtct  5220
ggtctgttat cttccagtga ctagtgcttc tgcaggctac tcacttgccc ttgcttctgt  5280
ttgcagagga ggtgcagtac attcaggctg agaagaacaa caagggccca atggaagctg  5340
cctcactctt cctccagtac ctgttgaagc tgcagtcaga gggctggttc caggcctttt  5400
tggatgccct gtaccatgca ggttggttcc ttcttcttcc tcacagttca gagtacttca  5460
ctctgctgcc tcagaaggct gaggggagaa aagtgactcg ttctgtgaca tctgtgtgtg  5520
gcttctgcct caggcgggaa atgtaaagac tattttgaat cagataagag aatggtttat  5580
accagaaata tccaaagcaa tctacagagt tgtaactact aggagaggtg acaatattag  5640
tagcatgccg gtatctttca agaggagaac gagtaaataa atcggtttta taatgtttac  5700
agtgctccat tatactgcaa tgaagcgtgt ggacatgtct gtaaatgaca acccagctga  5760
actgtaggca cgcagcattt aaatttgaat atcataaact ataatagcta taaagttcca  5820
catgagtcaa actaaacata tagggaagga aactggatct tgggcgaccc tggctgacca  5880
gtcctgggga gtaagcttaa taaactctcc ctgtctgact gagatcggtg tcctgtggtt  5940
tgtgaggcaa ttcctggact ctaacactta ggcaattaca tttcttgccc ctctgccact  6000
ctagcttatt cactggtgaa agaaggagaa tactttagtg ttaccaacaa tggggggggg  6060
ggggcggggg atgggaaatg ggaaaaagca ggcccggccc agtgtagtaa gaaagaaaca  6120
ccaaagaaag ccaagggctc ctgttgcttt cattgtattg gagtgtttgt cagtcggctg  6180
ggggatgggg tggggggtgg ggaagcacac ctttaatccc agctctgggg aggcagaggc  6240
aggcagatcc ctgtgagctc caccagtcat ggctggcctc agcaagaact gtatccatca  6300
catcctaaca caggtgtgtt gaattaacat ggtactgtta aagcaaacac gctgccttcc  6360
tcgggtgctg cggtccctag gaagccacac attggcagca tgttggcagc agttgtataa  6420
aaactaatgc tttttttcc ttttcttttt aattcggtaa aagggtttaa atgtcatttg  6480
ttataaaact tggtttcctg ctatttccag gattaacaat tgacttattc tttctatttc  6540
ctgctttata gaccatcatt ttgatacatt atctatttgc atctcagtga tacatgctta  6600
tcttaccctt ttatttcgtt ttaagaattg tgtgtgtgtg tgtgtgtgtg tgtgtgtgtg  6660
tgtgtgtgtg tgtgtgtgtg tgtctgagag tgggcatgca tttatgagtg cattgcctag  6720
aggtcagaca ttcccctgga gctggagtta atggcagttg tgagggactg acgtgggtgc  6780
tgggatctga ccccagtccc ctgcaagaac acgatgaacc ttacttgcta agccatctcc  6840
ccagccctta gctgttgcag ttactctcca ttccaaataa gccctggcaa tgaaaacaag  6900
acttaattca tatgaataca tgctgtgcac ctagattggg cagatctacc gctacactac  6960
catcttctcc atctatgaga ctccccctt tttttttctt tttttctttt ttgtggtttt  7020
ggtttttga gacagggttt ctctgtatag ccctggctgt cctggaactc actttgtaga  7080
ccaggctggc ctcgaactca gaaatccgcc tgcctctgcc tcccaagtgc tgggaattaa  7140
ggcgtgcgcc accaggcggt ttctccaggc tgtgtgcttc tgctccactt ttcttcctcc  7200
tcctctgtgg tatcctctcc ctcttcctct ttctccttct ctcttcccac cttcctctcc  7260
aacttccctt tatcagccca atcaccagct ctcctttatt ttactaattg aggtgggaag  7320
caggtttaca ggaaatcacc ggagtgctga ctcattcctt gttcgcagcc actcaatgca  7380
gaatggaatt accatcaaat ataattagcc ccagggctat ccacaacact tacctagcac  7440
atcaaatggc ccagcagggg atcaagagaa aaggaaactc aacttctgct tatttcctc  7500
atctcttatg tagccccatc agagaagctg ttgttttcct tttgtgggct ctaactaatt  7560
tgaatattat atttaagatc tattctctta agtaaaaatg gcacagctaa ctttaactgt  7620
aaaattatat gaggtttact aggaaaagtc ttgagtttaa gcaagaaagg gaattttaaa  7680
acatttgtat tggaacataa gtgctggaac atctctcttt gcaagtgagg tgctttgtgt  7740
gtacaaccct aagagtttct tttttttttt tttttaattt atttacttca tatttcagac  7800
agatctcatt tcaggtggtt gtgagccacc atgtggttgc tgggatttga actcaggacc  7860
tctggaagag cagtcagtgc tcctctgcgc tgagccatct ctccagcccc cctaagagtt  7920
tcataaagga atagtctgca ttaataaatt cagaaaaggc tcagaatata aagccaatat  7980
catcaagtag gtttccagtt tatgtattaa caaataatgc aaaaaagatt ttaagcaagc  8040
gattcctttt ataacagcac caagaacaat aaagttagga atgccagtgc tcctaactgc  8100
tgaaccacct cagcaatgca aacttttaca tcttagcact aagtccagct cctaattcgt  8160
gaatgtaaga tgtcattcat gtccgtgtcc ctatggttcg tttcagaagt ggtttatggt  8220
cttcgggtca taggtctttc ccctgctcag ctttgcttat tcctaacttt atttaaagtt  8280
ctcactgttg ttataaaagg aatcacttgg ggctggcgag atggctcagt gggtaagagc  8340
acccgactgc tcttccgaag gtcctgagtt caaatcccag caaccacatg gtggctcaca  8400
accatccgta acgagatctg actccctctt ctggagtgtc ggaagacagc tacagtgtat  8460
ttacatataa taaataaata aataaataaa tcttcaaaaa aattctaaaa aaatatggaa  8520
aaaaaaggaa tcacttagtt aaaaatctca ttcctagccg gttgtggtgg cacatacctt  8580
taatcccagc acttgggtgg cagaggcagg cggatttcta agtttgaggt ctacaaagtg  8640
agttccaggt ctctgaaaac cacaaaaaaa aaaaaaaaaa atagcactgg ctgctcttcc  8700
gaaggttctg agttcaaatc cctccaacca catagtggct cacaaccata tgtaatggga  8760
tctgatgccc tcttctggtg tgtctgaaga cagtaacagt gtacttacat ataataaata  8820
aataaatctt tgggtgggag tgagcggggc tggagagaga aggaaaagta tctgaagaca  8880
actacagtgt acttacatat aatagataaa taaatcttta aaaaaatcaa taaatgaaag  8940
atgccaatat tacccagagt tggcacagtg ataccttca taatgccaaa ttttggtggc  9000
aggattgttt gtttattaaa caggaataga aaaatttact ctcaaatttg tatgaaatct  9060
taaatggtca aaatattgga aagagaaact cacttggaaa ccttggggga cttatacttc  9120
ctggtgtcaa aacagtacag aacctccata aagccagata attagaccat tagcccagaa  9180
gtaaactctg aaggatatgg ccaaaggttc ttcaacaagg gtaccatgac cacccaaaag  9240
ggggaaaaaa aacccagtcc ctttaatatg aaaatacatt ggggtaagtg ggtatacata  9300
tgggaatgag aggtatcagg cataatcttg tgctatgatg tgaatttgaa atgttctcat  9360
cacattcatg ttttgagtgc ttggtcccca gcttgtgggg ttttaggagg tagagcctag  9420
ctagccaaag taacacgtgt atacgttcat gcatgtgtgc acacaggtat gagggtactt  9480
gtgtgtagcc cagaggctga cattcagtgt cttccttagg agctctccac cgtatgtttt  9540
tgggaatgga tctctcatta gacccagaat ttaccctctc gggctcgact ggctgggatt  9600
atagggtcat gctgctacac ttggctttt acatgatagc tggggacagg aactcaggtc  9660
ccagccttgt gtggtgagca cttttctact aagcaccttc ttggtcctgg agctattttg  9720
attgttttag tttttgggt ctatagggg gagaaaaaaa aaaaaaccac attgtcttcc  9780
cagggccttg aatgaagtaa atgagggtct gagaggcagg cacgcctggt ggatctgtcc  9840
aaaaacccca gagtacggca ttcttggatt cttttagtca gaagtcattt tccttctcca  9900
```

-continued

```
tttgcccatt gacttaatct tttcttggaa tggtgtggaa ggaaacactt ttcaagggca  9960
ggatgtaaga tttgtatttc ctctggtctt ctttactgtt tcctcttgag aagataaaca  10020
tgatgaattt gactaattta aaagtaaatt gagatgacaa agagatggct ctgtgattaa  10080
gagcacttgc tgatcttgca gaggacccag gtttggttcc tagacttaca tggtagctca  10140
caaccatctg taacttcagt tccaggaatc tgaccctctc ttctgctctc caaagatacc  10200
agacacactc acgatacaca gacacatgca aagtaaaata gaaataaata ttaaaaaaaa  10260
atatattgtg ggttgttgtt aaagtgcgtg aggggcattt tgaagatttt attctaaggt  10320
caaatacaag gcctcatatc tgtccttagg acttgaccct gaaagataat gaattttagg  10380
agacctaaac tgttgggtac caaaaatgag tattactccc attttggaaa atcatgaata  10440
gctgtattag ttgactttaa ctactgtgag taaatgcccg aggaaataaa aagcagaaaa  10500
atgagagcca agaggatctg tagcttctgc acccgtgcgt ggtgaggcag ggcaccatgg  10560
cgggagcatg tgggaaaagc cgcactttct ggtagacagg tggcaaaggg tgccgggcag  10620
gggccctgga caagatgcat tcttcaaagc acatctccag tgactcactt ctcccagaga  10680
gggtacagtt ctcagttgct ccttctgtat gaactcaatg tgctgccagt ggtgacgcca  10740
ggactcgaag gatgtggtca ccaggtcccg cagggtgtgg tcacctctaa agactgtcac  10800
cagctggtgt ccaagcctgc aacctgtcag cctcatggtc tggctcccca gactgtccag  10860
tgactgaggc catttgcaga tggttttcag ttcccttgcc actgatttga acaggattcc  10920
catgattttg acttcaaagc atttttatgt tggatttgct taagaaatcc ccatttctct  10980
tttctttttc aggttactgt ggactttgtg aagccatcga aagttgggac tttcaaaaaa  11040
ttgaaaagtt agaggaacac agattacttt taagacgttt agaaccagaa tttaaggcca  11100
cagttgatcc aaatgatatc ctttctgaac tatccgaatg tttgattaat caggaatgtg  11160
aagaaatcag acaggtaaac caatgccagg tactaaattt gaagaaaaat gcagagacat  11220
tggaaatgcc catttttctg tcttgtttta ggcccaagga taattgaaac ccataaaagc  11280
tctcatctag cagatataat gactagaata gaatttttaa agtgaatggg gtaatttttg  11340
tgctagacta ttagaaaatt atttaaccta tttgcagtta aagttgcccc cttactttaa  11400
aaaaaatagt ggtttatgca taatgcaaat cacaccaaac agtgcaacaa ttaaaaggaa  11460
aaatatgtca ggctcttggg catagataca tttattacag tctcgcagtc acttaactag  11520
tgatgtgatg ccaggcagtt ctctaagcat ctgtggggtt tttgttgttg ttgttgttgt  11580
tgtttgtttg tttgttttc atgtctaaag taagaaaatt tatcttttgt tttttgtttt  11640
tttgtttttt tagatttctt tattttattt tattatatgt gagtacactg tagctgtctt  11700
cagacactcc agaagagggc gtcagatctt gttacggatg gttgtgagcc actatgtggt  11760
tgctgggatt tgaactcagg accttcggaa gaacagtcgg tgctctcaac ccctgagcca  11820
tctctccagc cccctttgt ttttgttttt gtttttgttt ttgttttttt gtttgtttgg  11880
ttttttgtc gttgttgttg tttgtttgtt ttgtttttc gagatagggt ttctctgtgt  11940
agccctggct gtcctggaac tcactctgta gaccaggctg gccttgaact cagaaatccg  12000
cctgcctctg cctcccgagt actgggatta aaggcatgca ccaccacgcc cgacgaaaat  12060
gtaccttatt agcactcttt tagggctaaa tgagaggtca tgcacaaaat gtgtatgtca  12120
gcttgatgca tagcagtcta tgcacaatgc atttcagtta tcattagaaa gaaaagtcat  12180
agaacatctg cttagaaaag agacctgctg ctgtgctgtt aggcatttcc aaatggctct  12240
gtgtgccgat acatccttag ggtgaatggt tagcgtctgg gttaacgctt ttaccccagg  12300
attgctcttg gtcagggata taaggattca gaagatgaga acatttgcct tggcatattg  12360
ataacacatt ataaaggaca aaggtgaaga aaggaatatc ttaaaagcta gtgctggaca  12420
gggcaaaaag atgatgctaa ctaagcccta ctcaactata cttcacagtg atttcaatca  12480
gataccgctt ccacaaaagc ttgccagagg aaaggctgag ctgcctgatc agtgtgctgc  12540
atttgtctcc cccagatccg agacactaaa gggagaatgg caggtgcgga gaagatggcc  12600
gaatgtctta tcagatccga caaggaaaac tggccaaagg tcttgcaact tgctttggag  12660
aaagacaaca gcaagtttag tgaattgtgg attgttgata aaggtggggt gctccaagaa  12720
agaaccctgg accctgctgc gctcctccca gttctcccca ctttactttc catcagaggc  12780
gctgttcact tcagatacca aaggctatat ccctaggata caagcagtgg aaagctgaat  12840
tctgggagga agggaactac atggcatgga attaacccga ccaggtcaaa gaatctaggg  12900
aaggcttcca gccccaattt gttatcagag aaatagcttg agaattctag acctaaaggt  12960
tcaaactgca agacttacct ccctatcaga gcagaggctg agtgttgggg gtgatagcta  13020
tggactggtg ctcttgcccg gaagccatct ggactccgac agagcaagag taaacgaaga  13080
ttttctgtgt ttaagccaac ctcatttggc ttccggaaac tcacttcttg ctttaaacag  13140
accttgataa atacctgagt ttctagtttc ctttctcacc tagatttcct tagaacataa  13200
attattccag aaactctcta catcgttggt cagagatgga atcctgtctc tttagtgtgc  13260
tcaggaatga cgcccctgcg ttattggcgt gagttccgga gtggggaggg gctccggatg  13320
caaactgctg agagccccgg gttccacact tggagtcgcg tagttccaga tgaaactgga  13380
attcaattgc caagttgagc ttcaaactca gaataatcct tgcagttgtt ttaagccgtc  13440
aaagtggggc tctctagatg gctcagtgga taaggttcct gccactgatc ctgaagaccc  13500
aaattcaacg tccagggcct acatgataga accaatcccc aaacagtgtc ctcatccctc  13560
ggcacactca ctgtgtcgtg tgtgacacac acagtaaaca aatccatttc aaaaataaat  13620
aaaatgttaa gaaagtgcaa gaccgtgatt gtaagagctc aacggaaatt tagatgttta  13680
gtgttagtgt taggactttt tgggacttcc ccaaccaaaa ccataatcac attgcgcatg  13740
cttttaatcc cagcactcag gaggcagagg caggtggatt tctgagttcg aggccagcct  13800
ggtctacaga gtgagttcca ggacagccag ggctatacag agaaaccctg cctcgaccac  13860
cacccccttc caaaaaaaaa aaaaaaagat tctaagctgt aagctgttat ttgtgtttat  13920
gattgtttgc ttgcctgttt atcacaaagg tttcaaaagg gctgaaagca aggctgatga  13980
ggatgatgga gcggaggcgt ccagcatcca gattttcatt caggaagagc cagagtgtca  14040
gaatctcagt cagaatcccg ggcctccttc aggtaccaag catcgtttgc tctcatccat  14100
gatggtgtcc cccagcactt tgatgccctt tgaaaaaaag tctttttaaa ggatgattaa  14160
gaaaagaaag aatttgtggg gcaataggga cttcataatt agaatccctg ctcctgtctt  14220
ccatggcctc tgcatggcct tcaaccctcc ccctcctctc ccctcccctc cccctccctc  14280
cagtatgtat gccttcatct gtaccgtgtt cccagaactt cagtgtccat gacttctcaa  14340
agcagccttg ctctctaaag aacacttctg ctcactaagc aatggctttg agaatctggg  14400
ctgacagctg gttttcctcg gctgttttg atgatctgtt cttactttgt tccaagtggc  14460
tttgttttga attaggccat tcttgctgtc ctttttcttg ataaagtttc cacgattaag  14520
aaagaattca tggggctgga gagatagatg gttcagcgtt taagagcacc gactgttctt  14580
tcagagatcc cgagttcaat tcctagcaac cacatagtga ctccagcgtc tgggttaatg  14640
```

-continued

```
tttttacccc atctgtaatg ggctctggtg tactcttctg gtgtgtcaga ggacagcgac  14700
aatgtgtata ttcatataca ttaaataata aataaatctt caaagagaaa agaaggaagg  14760
aagaagtaac agagagagag agagagagag agagagagag agagagagag agagagagag  14820
agagaacaca ctttggccaa gatcccaaac ctcaaacagg ggcattgttg ctagagtcag  14880
aactcatgtc cactgaatgg cagttgcacc atgattcctt gtagcatgaa cccttcgata  14940
actttgtccc ctctatatta cagaagcgtc ttctaataat ttacacagcc cattgaaacc  15000
aagaaattac caactggagc ttgccctgcc tgccaagaaa gggaaaaata caataatatg  15060
tgcccctact ggtaagtcag ttgctgtcac tcacagaact ctctggcttc gctttttctt  15120
ccccctttgg gggctgtaaa aggaggagtt ttccccgtgg cccatgctgc ccatgggaga  15180
gctggtctag cagcttaagg aacctggaca gcgataagga gggagataag tgtcttcttt  15240
agtttgcttt tggttcttgc tacctgagtg cacgttactt aggaagtagc ttggcacttt  15300
tcagccattg tttaaactgt cattgttagt gcggaggagg gattattagt ttatttgtat  15360
cccagtggtc atagagaagc caaaataagt accattctgg aaaaacagct aacacaggtt  15420
atctgttggt tttttttct tttctttttt tttcttttt cttccctact aaaaggttgt  15480
ggaaaaacct ttgtgtcgct tcttatatgt gaacaccatc ttaaaaaatt cccatgtgga  15540
caaaaaggga aagtggtctt cttcgctaac caaattcctg tctatgagca gcaggcaact  15600
gtgttctcac gatattttga aagacttggg tatgtactac tacaatcaat ctaactgctt  15660
tgatttttgg tttttgtttt gtttatgttt gtattttaaa ttctagcccc tttggctggt  15720
tttgggggct ttgttgtgtc tggttttggg ggctttgttg tgtctggttt tgggggcttt  15780
gttgtgtctg gttttggggg ctttgttgtg tgtttctga gacagtgtat cacgtagcct  15840
tgagttgtct ccaacccact gtgtagctga ggttggccta gaagagatga tcttcttgct  15900
tctacaagtg ctgagattac agtgtgcact ggcatgcctg gctgttctct gatttctttt  15960
cttttttttt tttttaagat ttatttattt attatatgta agtacactgt agctgtcttc  16020
agacactcca gaagagggca tcagatctca ttatgggtgg ttgtgagcca ccatgtggtt  16080
gctgggattt gaacttcgga ccttcggaag agcagtcagg tgctcttacc cactgagcca  16140
tctcaccagc cctctctgat tttcaaagct atgattaaag gaaaatcgcc atggacttaa  16200
cttttagagg tagttccttt gtgcaataac atttttggtt taactttacc agaaatgcta  16260
agccctcatg tcatgctctg acagttaatg aacttggtgg ccaaatttaa catgtaggcg  16320
atacacaggt catccttaat gatgttatac ttgattggct attactcttt tcaaaatcat  16380
ttctctctta atgacttgaa agaataaata cactgtgatc agctataacc tcttgcattt  16440
cctgactccc cggctttgtg tcaggcctgt gagaaagttc aaggtactac ccagttgtac  16500
tcttttgggc ttgggctgac ttctttaatt gctgctctga cctagacttc tactttgtct  16560
ccttgttcat tcacatcaag gttgatgata agggatttct gtcattcccc aggtacaaca  16620
ttgcgagcat ttctggggca acatctgata gcgtctcagt gcagcacatc attgaagaca  16680
atgatatcat catcctgaca ccccagattc ttgtgaacaa tctcaacaac ggagccatcc  16740
cctcgttgtc tgtcttcact ctgatgatat ttgatgagtg tcataacact agcaaaaacc  16800
acccatacaa tcagatcatg ttcagatacc tagaccacaa acttggagag tcacgggacc  16860
cactgcctca ggtatttcca atcttctaag aagaaccaca gtttttcaga gtcccactta  16920
gttgctcttt tgtagccaca tttgagcttg ccctcctcgg ggtctcagtc catcggtaca  16980
actcagtggt caatgttggt tcattcattt gaccaacagt tgtcccttgg tgtccagggt  17040
agatgccctt cacaaaaaac aaaatctagg ctgcttaagt ctcttgtatg agatgacatt  17100
gcatttatat ataatctaca cactttcctc ttgcatactt taaatcttct ctagattact  17160
gatattgtac agtatgatga aaattttata taaatagttc tagtactgta atttttaggg  17220
aataaaggtg ggaaattcat acatgtttag tacttatgaa gttttaaaaa atatttttga  17280
tccatggttg tatgaattca catttatata acctctggat ttggagggcc agctgtataa  17340
accatgggct tccatggacc ttgtgcattg ttctaggctc tgggacacca atacagaaga  17400
tatagtcctg gctctcatac agttaagttt gcagggagcc aggaacatag tagtcacagc  17460
ttatcatgag gtatgctgca gagacaggta aagggtgttg tcagaacata aggggtaata  17520
aggcatagaa atgaagggaa ctgacagggg cttgccaggt agatagcttc tggtttctag  17580
taagagggtg ctgtgtgtcc aggggctcag ggaaatggaa gggcctgaca tgccccagaa  17640
ccttaaaact ctacagtatc acttgagggt agagtgtgaa gcagggaaca acagtcaagc  17700
tgattgttat gacagatgac ccagagacac caggagggca gagcgtcagt gggcaagtgg  17760
atggcttagc acagggaaca agcagcagcc ttctgatgtc atatgagaag agtcacttca  17820
gagtcattct tacatgtgac aagaggagta caaattctcc ttctgtctat cataggagag  17880
ggggtgcttt gctgaaagtc aacgatatag aaacaggagg gggctagaga ggatgaggac  17940
ggtttgactc aggcactgat agatgcaata aagaatgacg gtagtgtatc tatcaggggc  18000
cccaagaagc tgtaaaccat gaattatata caattctttt gctccaacaa taaccttttt  18060
aggacgtgca ggttaaagga catttagtac aggacccaca gtttgttatt ctcgagtatc  18120
gttgctagga agcagatttc ttaccgtcca gctaatcatt taggtgaatg cttactgaag  18180
ggtgttatca tactgaatct acacagctct cttgtacacg actcactgat tgttgaaggt  18240
atttgtccag gcgcacaaaa tgcatgtgat atgaatgagc ctggaatgga ctttttcttc  18300
ccattgtgat gtttagtaag agactggggg ataaaaaaaa cagggtagcc ctgcctggaa  18360
aggtttcctc tctgttctgg atgacacgct agatttattt ccgagctttg ctccaggggg  18420
gtctttgtgc tggagaatgt cagagagcca gtggtggggt gctccttaca ggtcgttggg  18480
ctgactgcct ccgtcggcgt tggagatgct aagaccgcgg aggaagccat gcaacatatc  18540
tgtaaactct gtgccgccct ggatgcctcc gtgattgcca cagtcagaga caacgttgca  18600
gaactggaac aggtcgttta taagccccag aaaagtaagt ggaggtcagc agcccacacc  18660
tcgcgacttt gtaaccttct gtcccctctg cgtcagagac agtggatgaa gtttgatgct  18720
gtatttgttt ggtaaaagca tagtggttac attgcctatc tttctcccta gtcaacctct  18780
tctccctagc gacgcatgag tctcaaaggt agccagaaag ggacaaacat ccctactctt  18840
taccagcagc tgagtgaagg aggcagtggg aagattcaag cattttgaaa gcctcaatag  18900
ctagtggcgg aatcaggtct ctgtgctccg ggccctaggc aggggctatg tggccatctt  18960
gttcttgtat gtatctgatc attgtagtgg catgacccga atcatgacag ttcaaaaggc  19020
cagaacatgt ttttaaaatg agcttcatta gaagatggtt attacttatt aactacctgt  19080
gtaagcaggg aggtaccgta gttacccacg gctggatctt ggcctgagca ctcgttctgt  19140
gagttgacag caggatcaat ggcagggtca atggcaggat gagcaatggg ggggtggggg  19200
ttgggatggc acaaccctgg ttctttctga gagtcccccg tggagagtgt gaagaaggtg  19260
cctccccacc cacgcccacc ccttagcaac actcaagggt ttttctacag tttgagccct  19320
tggagcttag tctacttcaa agtcattttg tgtcactttc tccgtctatg caaaccctct  19380
```

-continued

```
acgagctatt ctgagggtgt gtcccagctc ctgcgcgcct tcctttttcc cttattattc  19440
atcttgcggc agcttccccg gagagaatga ggtttcctcc cctctttgag agatgccttc  19500
ctggcctgca cctgcttccc agggctctga tgggcgggtt taggagcaca cctttgtttc  19560
ctttaaggag tgggtgggtt ggggagcagg gggagggggg agggagggga taggggggttt  19620
ttggagggga aaccaggaaa gggaataaca tttgaaatgt aaataacgaa aatatcttta  19680
aagaaaagaa aagaaaagga aagaaagaaa gaacctgcct tctgtgcagc atagggtagc  19740
tcttgtcagc tctctgtcac tgaaacagga catgtgacag gcagttcttt ttctgccaaa  19800
agtacacaaa tgtgaacgat aagctcaatg ggggcactct tgggggctcg gaggtgcgca  19860
ggagaatagg aaatcaggaa aacggggctg gagtatggta tttgccgaaa ccagaaggct  19920
gccagacctg ccacagtaga ggcaccagga aagctgactg agacgctggc ttagactaga  19980
ccaggagaga cactagaatc agaagcagtt ccgaggtcag aggcttctga ccgcctgctg  20040
tgatttgggc cacgtgagct tggagcctgt ggctttaaag gacttaccca ggatggagca  20100
gcttcgggaa atggctgcat aggacctggg tttccttcag cttactcaca tgcctttgac  20160
cccagtttcc aggaaagtgg catcccggac ttcgaacacg tttaaatgca tcatctctca  20220
gctgatgaag gagacagaga agctagccaa ggatgtctcc gaggaacttg gtaagcctgt  20280
gccaagtcct ggagagagaa atctcatgtt tcctgtccct tccatttaga ggtactcatg  20340
gattgctcgt tagtgtcttc agttttgggt gagattatac tcagaggtgg actgacttat  20400
ttattcacac atatttcttt ctgtctctgt atcttcttta tctcttcatt cttttttgcc  20460
atcatttttt tctccattcc tttttaaaaa gatttatttt tatttgatat gtgtagatgt  20520
ttttgtctgc atgtatgtat gtatatcaca tgtatcagat acccgggaac tggagttaca  20580
gacagttgtg agctaccaca tctgctggga atcgaaccca tgtcctctag aagggtagct  20640
ggtgcgcata accactgagg agccccccatt tctctagctg tttttaagac aaggtttttt  20700
tccctgtgtc cctggttggc ctgaaacttg ctatgaagac aaggctggct ttgaacttgc  20760
aggggtcccc ttgcttcagc ttctgagtcc tggggtctct ggcaagcgcc accatacctg  20820
gctcagatat agactttctt aatcctaggt tgtttaggaa ccttatagga gttctttaat  20880
tctctcttgc cttttctttt ttaaatacaa aacacatcca cctggacata catacctgag  20940
aaatactgtc tttaaatcat cttctaaatt tcctttcttc cttttttttcc cctcttgaga  21000
tagaatctct gtgttcagtg taggctggcc ttgaactggg aactctgccc ctcctcctcc  21060
tcctcctcct cccaagatgt gcatcatcac tgagctgcca ttagagtgcc attgtccctt  21120
ccaagagcag ttcccccagt gacctaacac tctctcactg tcctcagctc ttgaaagtgt  21180
caccacctcc taacctcaca cactgaggac caaccagcct tttgccacat gagcatccag  21240
aaggcactta gacagtagct aaggcacagc actgggggag gagtttgaat aatgaatcca  21300
ctatgggtcc taaagtagta gggtagcaag catgctctct cctctagagt tttggaaact  21360
ctctgtaagg taaagagtaa agagaccagg tagtcagtac atggctcacc taggaacaag  21420
ataacatggt ctgactaaag tggtggatgg acagacggac aggaatagag ttgtatgact  21480
tacttttttg ttttgttttt gtttttaaaa cagtctgtct gtatagctct gactgtcctg  21540
gaactctctt tgctggcctc aaactcacag agatctgcct gcctctgcct ccggaggcat  21600
tcacacttta gaatcttttc ccacctcctc acattgagta tctgtcaata gctgcctcac  21660
ttcttctgga acttggacgt ttttcattgt gaactgggtg tggtggcacc atctctactc  21720
ccagcagctg ggagcctgag tctgaggcca gcttaggcta catactgagc tcctgtcctt  21780
ggggcggagg ctgggaagaa cttgtcactg tttcttgttg gtacccgtcc tgtgttctgt  21840
tattgcaaat gtgagggaag ccatttaaca cacaaatgca tttcacttct ttgaactgta  21900
ctgtgcttgt ctcaagaagc ccaggacaca aaacaataga gcaagcatct ggggctgttc  21960
ccacttcgcc tttccccccc tacccacacc aatcttcccc tgagtctgaa tcgctgtgaa  22020
tcccacagta gaaccaagca gtcaagacat gcacatgcgc acacagatgc ttccgggata  22080
actgtgtttg actccgcctt gtggttggtg ctgcaagtgc tgctctgaga tcaggtgttt  22140
gggcttcata gcaacataga gcatgctggg aagggtcctg gtgctcccat ttttatataa  22200
ctgtctccga tgaagctctt gagacgtgct actctaatgg tatcttcatt ttgaaaggca  22260
aagtgtgtcc ctccttctct tcctcctcct ccttcttcct taccccctctt cttcgttctc  22320
tgttatttct gaactacttt ggctgtcagc cccttaagcc tgcagagcat agacaccaca  22380
gagctaggct tgaattcttg cctcacccac acaatatgag ctttatgaca ttgggggtaa  22440
attagtttc ctttttataga agatttattt acttaaaaaa aaattatgtg catgtgcatg  22500
tgcgggatgg tgttgttgcc tccaggggtc agaagagggc gctgaatgcc ctggaactgg  22560
atttacaggt cgttggaagc cacccaatgt gagtgcaggg aactgaactt gggtcctcta  22620
caagggccta actattgagc caccacttct gctccttact caatctttct gaatctgttt  22680
cctctttttt tttttaaag atttatttat ttattatatg taagtacact gtagctaagc  22740
tatcttcaga cactccagaa gagggagtcg gatcttgtta cggatggttg tgaaccacca  22800
tgtggttgct gggacttgaa ctcaggacct ttggaagaac agtcggtgtt cttatccact  22860
gagccatctc tccagcctgt ttcctcttta aaaaaaaaaa ttaaataatg acctcatgaa  22920
attagaaaat ttcaatgcaa ttatgaagct tgattttggg tcatttagta aatagttatt  22980
ttacacactc ctccccccca cccccgcgc acgcacacag gcacacacac acacacacac  23040
acacacacac acacacacac acatagctta agacccagtc tacttcagga taaacatctt  23100
tcttataatg aataagaaag aaaatcagag gaccggtgct tgcaaatctt ttatttatct  23160
atttatgttc ttaccctgta ggaaagcttt ttcaaattca aaacagagaa ttcggcaccc  23220
agaaatatga acagtggatt gtcggcgtcc acaaagcgtg ctcagtgttt cagatggcag  23280
acaaagagga ggagagccgg gtctgcaaag cgctcttcct gtacacatca catttgcggg  23340
tacattgctg ctctccaggg cttattctca tcaccgcgcc tcctgggatc tgtactgagg  23400
cagctgagag aacatcagcg tctcaagtct aagagcttag tgaggaactt ttcccgaaag  23460
tcatcactaa ccttatttgt tttctgaaac ttatcatcaa gtctccaaaa actggattaa  23520
aggctcagag tctatgccac acctccctcc agcttgtgac tggtgaccac catctaactg  23580
agctcaaaaa agtggctcct gtggccatat cctgaagctt tcgtggtctt aattttgtta  23640
taaagtcata tattagaatc tcaggggctc tggttaacac agagggaagg agtaactgta  23700
agagccctca gctctgtttg ctatgctctg ggaactattt aaagacttac tccacaccat  23760
gggattgtgg gatctaacgc ttaatggact ttcagcatag gtggtaaggg ccatcgttat  23820
gcaaggccca tgtacacttt aagtatgact tggaatttaa ggggaatgtc aaagctaact  23880
tgcttttgtt attgtttctc aagatatgct gtttctcctc tcccaaggtg gagttttata  23940
atccaaagtg aatctacttt taattttcta gctgagccaa aaatagaagc cagcttttgg  24000
ttcagaggtt tttattgtag acccactaag ggccattcgc cattaaaccc tcagctgtac  24060
tgtatgagaa agattttctg caaaccagtt ttgtgctaaa tacagcgagt tgaacttgag  24120
```

-continued

```
tgtagtgacc atatgcgacc tcagaaatgt attgagaatc acttttcatt tcaaacagaa  24180
atacaacgat gcactcatca tcagtgagga tgcacagatg acagacgctc taaattacct  24240
caaagccttc ttccacgatg tccgagaagc agcattcgat gagaccgagc gagagcttac  24300
tcggaggttt gaaggtgagg gagatttctg aagtcaggag tccctggggt ctggtggctt  24360
ttgtggcagt gtgcacatcg tagttagcat acgtagccat catgttgggt ttaaggtgag  24420
atttgtaggg gctgtgacgg agcatgacct tagcatggct gaaatcccca gcactaaaaa  24480
acgaacctat gctgaaactt tagagccaac caaccgacaa caggagggtt tggcttcaga  24540
gaaatctaat gcctgtggat ggatctgatg cttgccccac ttttcacttg ggaaaatggg  24600
aaacagtggg atttggaaag ggtgcttcct ctaggtggta ggtagtgcta ttctgattaa  24660
ctcagtaatt cagaaggttt aataacaaca gctcgtgtct gatggtgtca agattgtgct  24720
gtatgtatgt ccttccttcc ttccttcctt ccttccttcc ttccttcctt ccttccttcc  24780
ttccttcctt cctccctccc tccctccctc cctccccct ttctcttctc ttctcttctc  24840
ttctcttctc ttctcttctc ttctcttctc ttctcttctc ttctcttctc ttctcttctc  24900
cttctcttct tcctcctcct tcatcttctt ctttcttcct cctcttcctt ctccttcttc  24960
ttcaaaacac agtctgtata gccccggctg tcctgaaact cactttgtac accaggctgg  25020
cctcgaactc agaaatctgc ctgcctctgc ctcctgagtg ctgggattaa aggcgtgtgc  25080
caccatgccc agtttgtgca catatatgtg catatgttta ttataaattt tactgataca  25140
ggagatggca tagcacaaaa cacacaaata ataaacacgg agttcatgtt ccacagaatg  25200
cctttggagg tcttttcagt acccttgtgt ccagagccaa ccagagacag caattaccca  25260
atatggagtt ctgaaatgaa agtcagtttt atttcctgtt aatggcagaa ataagaacaa  25320
aacgaaacag cagaagcatt ttggaagctt gcttgtttct cagtgatggg agcaacattt  25380
ttctgagcca gataatagtt tttcaaacac gggtgggaca tttctgcatt tttacgtgat  25440
gcataaacag tagctaaatt taatccccat tatatactta gcactttaca aagtctagcc  25500
agacaataaa ggatgaagca agtgctatct tcatttccat ggtatgggta cttctaggat  25560
caccaatctc caaccatcac catgttgctg aacttgtgta aaattgagca gtaacacaca  25620
ctgacatttc taccattcat acactacagg taagtacaca ctcaagagcg tagataatag  25680
taaactgtaa taaaatgagt taggaaatta ataagcgtgg ctatttgtta catttgtttt  25740
tagtcattga gctgcaagca taaagagttg aaattttaat aatagttata tttaaaacca  25800
ggtccacaag tctgaagaac ttaataactg accataatct ggtttgatct ggttctatct  25860
agtacaccac cagtgtgtgt gtgcgtgtgt gctcctatgc atacttatac attaaaaaaa  25920
aaaaagatat cctatgcttc aatttttaac ataaaataac cttctgacag ctgggtggtg  25980
gtggtggtgc atgtctttaa ttgcagcact caggaggcag gggcaggtgg gtctctgggt  26040
tcaaggccag tctggtttac agagccagtt ctaggacagc cagggctaca cagagaaacc  26100
ttgtttcaag acaaaacgaa acaaaacaac cacaaataaa aaatatatct ttttgatgtt  26160
tccaaatcag caggtgtata taactcttta actttaatag taacagtgta tttacctcag  26220
tttggtagcc tgggatccat tgagctgttt ctcactaagc agtgttttgg ttgttggttt  26280
tttttttttt tttttttttt ttttgtattt agttcatagt ttcaacactg attgtccttg  26340
gaatcttctt cagagttttt tttttttttt tttttaaag atttatttat ttattatttt  26400
atttaagtac actttagctg acttcagaca caccagaaga gggtgtcaga tctcattacg  26460
gatgttagtg agccaccatg tggttgctgg gatttgaact ctggaccttc ggaagaacag  26520
tcggtgctct taaccactga gccatctctc cagccccaga gttttctaaa tagaactatg  26580
agtcaattcc tatctgtgga ttgctgtatc aaagaacatg tgagttttgt attgctgcgc  26640
tgcttttcta aaggggattc ctgatgaaac gagtgtttac tgctctgatc tctggtgaac  26700
agtggaaagg ttaaccgaaa tagaaggcca ctgtttgttc taaagcttta acatttgtaa  26760
gccttttgca aaatgctctc tatttgcaga aaaactagag gaattagaaa aagtttccag  26820
ggatcccagc aatgagaatc ctaaactaag agacctctac ttggtcttac aagaagagta  26880
ccacttaaag ccagagacca agaccattct cttcgtgaag accagagcac tcgtggatgt  26940
aagtgtgtgt gtttacagat tagctctagt ttattgaaaa ggttgcccgt tcttcactgc  27000
cttataatca agtatccata catgtgtgga cctgttctga tgatttgttc ttacaccaat  27060
tgtcattgtt tgtattgacc cacagttata agtcttggtc ctatagagga agccctgcat  27120
ccttttttaaa aatttaaaat ttccacttcc agtcatcctg taggttttga ttaatgacta  27180
atgtgtctta tatacctcac agttatcttc atatcatctt ttaaaaataa tttactcaga  27240
ttttaaaaac cagttttaaa attgggcaat gggctggaga tacagctcaa tggtcaaatg  27300
cttgttcagc atgcatgact ttaatcccca gttctggaaa aagatagata tctctctgtt  27360
tatgtagaat gccttgagtc tggccacagc gcctccctct gtttatgtag aatgcctgca  27420
ttgtttctgc tgagtagtag attacccata gagccagagg cagaaaaagt caagctttat  27480
tattttatga gatccgtgga tcaggatctg gaaaggactg gatacttatg cctcaaggtc  27540
tcctgaggcc acagtcagct cggcactcaa ggctgacctc tcggctcctt ttgcaggttg  27600
ttggcaggct tgtgaagatg agcctccaac atggcagctg cccctgccta cagtgagatg  27660
agagactgag gagaagaggg cctagtagac agacactgcc attttataaa gtccatcttg  27720
gacctgatgt cccaccacat ctcccatatt tcagagataa actacagatt atttttagaa  27780
tataggatgt agaagtcatt aagggtcgct tgtcatgtga tctttgctgt cttcttttgt  27840
taatgaatgt gggtgtttac catgtgcgtg tcgtgcccac agagtccagg aagggggcat  27900
gacatgccct ggaactggag ttaacagaca gttgtaagtt gccatgtagg tgctgggaat  27960
tgaactcagg tcctctggaa gaacaaccag tgctcttaac caccgagcca tctctccagc  28020
cccctttgct gtgttttatt agcattttgt catttttagt atagaggtcc tgcatacatt  28080
ttgttagatt catacctagg tattaatttt agtgttgtca ttccgaaatt gtactttcaa  28140
atatttctca ctgtgggcta ggaagacatc tcagtaaagt gtctaaagta caggcatcag  28200
gacctggctt ccagcaacct ggtaaaaaag ccgagtacag tagagtactc ttgtaatccc  28260
agccctgggg acagagataa gcacaaccct aactggcaat gcccaggtcc cagggagtta  28320
ctcattactc agtcttaggc agaacgaagg tgggtggctg ttaagaaatg atacctaggg  28380
ctggtgagat ggctcagtgg gtaagagcac ctgactgctc ttccgaaggt ccagagttca  28440
aatcccagca accacatggt ggctcacaac catccgtaac gagatctgac tccctcttct  28500
ggtgtgtctg aagacagcta cagtgtactt acatataata aataaataaa tctttaaaaa  28560
aaaaaaaaaa aaaaaagaaa tgatacctga ggttgacctc cacatgcatg tacacacaca  28620
cacacacaca cacatgcgtg cgtggacata ctcccctcca acacagtcag ccatgtacac  28680
ctccacacaa cacacagttc ttccaattgc agctgtctgc tgatatttac tgtgtaatta  28740
atttacatgg attgatcttt caccttaaag ccttgctaaa tttcacttac tctatgtctg  28800
aagcttgtct ttttaatcac ttaaaatatc tcctacatta agccataatg aggcagagtt  28860
```

-continued

```
ctatatcact agcatcaatt gttgtttgga atttaggatt tgccagtctg aaatccattt  28920
ttatctttag ttgtattctc tttttgcata tacatccatt atatcaaatt gatgtgaggt  28980
ttaaagttta caagtggtgt ctaactggcc gttgcttttc acttttaggc tctgaagaaa  29040
tggattgaag aaaatcctgc actaagcttt ctaaagcctg gcatactgac tgggcgtggc  29100
agaacaaacc gggcaacagg tatttatgtc tattgaatta gatttagtat actatgtata  29160
taaaatgtat aaacactaca ttgtttttagt gtttctatca gtcagagctc aaccagagaa  29220
ataaagctac tagattatgc atatgtatgt ggtatatatg taagtatgta tgcttatttg  29280
tttgtttgtt tatttatgta cttagagata gggtttctct gtgtaaccct tgctctcctg  29340
gaactcactc tgtggaccag gctggccttg aattcagaaa tccgcctgcc tctgcctccc  29400
gagtgctggg attaaaggtg tgcgccacca ctgcctggcc tatactgtta ttctttaccc  29460
agtagatttt ttttccccat ctactgcctc tttaatagtt ttaaaaaaac agtccaggca  29520
atcctgaact ctagctagtg tggtctaggg aggaaggtta tcatttccca taagaaccct  29580
atgtggctag ctctcatcac agctacgtcc caagtcatat ctcacgactg tatgacctgc  29640
cctcgctgtt cttcctgcca gtgttgttta cactaaacaa gtctccaccc cttctctctc  29700
cgtcctcagg cattgctctt gtacttttcc attgtggaat ttcccgatct cataaacata  29760
gaatggactc aagtgttgaa tgtgtggttt cgagtctaac actaccctaa tgtggctgga  29820
ttttcaaagt tcttttgccat ctctccaaca tgaatccaac ttgattttca agctttgcta  29880
ctgacatata aatcgagcct tgaataatat tttgtgtgct catccatgca tgcatggatc  29940
catggatcca atcatgtgtc caaccactca tccacccatc cgtgcatgca tccatctttc  30000
cgtcatgcat ttagacctta ctcagctcct gcttctgtga agaagcagcc atccctgtca  30060
tctaacaccc gaggtgcccc tccccccgcc acgttcccat cttacagatc tcacccccact  30120
tcctccacaa tggcttcctg ctcatcatcc ttatagataa agatggaatc tttaagcgtc  30180
atatttctac ctgctcagcc ataacccata attgctgacc gagtgttgga tggatgaatg  30240
aattggttag gatgattctg ctattgttgt tttctggatg attctttctt gttttatagc  30300
taacctggga aaaaaggtgg acttttacaa aaagccacag gttgcttggt gtttggacat  30360
tttcagattc ccttatctgt agcattttta cttcctactt tgagacacat gttgtaatgt  30420
ttatgcctta ctatcttcat ctgtcaaatg gaacaataaa tagttgtccc cagctcatag  30480
gttaacgaga atggtgaaac ctgagctttt ttttttttt ttttttttt tgtgaaaatg  30540
actttggcac ttttagatgg ttcaaaatta gtagccagtt tatgagtgag ttgtacagtg  30600
acctctttat ccaacacagg aatgacgctc ccggcacaga agtgtgtgct ggaggcattc  30660
agagccagcg gagataacaa tattctgatt gctacctcgg tcgctgatga aggcattgac  30720
attgctgagt gcaatctcgt cattctctat gagtacgtgg gcaacgtcat caagatgatc  30780
caaaccagag gtgagagcgg ctgatgtcat tcccgccccg cacccgcttt tctcctttcc  30840
tcagctgtac catgtgattg acagcacagc tgactctggt actcgaaatc taaaagctga  30900
ctgccttggt caggattggg tggttatagg tttacccata atactccatt gcaactctcc  30960
acaatggtac tgcaatttta cccagcgttc aatggcatag tcgtgaaaat atcatatcca  31020
ctaggccaga ggctttgcca gtcggcaagt agacctttga tgggtgtggt gagtagctct  31080
ctgtactcca gagtctggtc ccacctgaac cagagtctga cttcctttcc ctttcttgtt  31140
tccccaagaa cagcccccac attccctttc cggaataacg tctctgtgcc tgtcactcat  31200
cagtcacatc catttttcgt cctcctccac cgcttactgt gcggttcagc cagccagact  31260
ccgcttcctg ctcgtccagt ttctcagata ctgtcgctct acatgttagg tcctatctct  31320
gtctctgcca cacacaacct aattcttcta cctagaacaa gcactccttt aaatgcccac  31380
taccgtttat atctgtctct gcaagagcat gacaattgca ttcctttctc cgcattgcag  31440
aagggtcagg tgcgcgtgca cggtgccact gctgcgggct catgccagat tatctgtaaa  31500
ttagtgttgc tggcagtgca gagcaatcag actatgccat tggagacccc atgaaaactg  31560
ccagagatgg cttatctgtg tgctgagcac actggctaga acctgcattt gagtctactc  31620
ttcggttcag cttccctaga aagtaggatg cagtgaatca aagttgaact cgagaaatac  31680
tcctcacatc tctttccagt aacctcagag tttgacatta acacacaaag aaaacgtttt  31740
ctgcaggccg aggaagagca cgagatagca agtgcttcct cctgaccagc agcgctgacg  31800
tgattgaaaa agaaaaggcg aacatgatca aggaaaaaat aatgaatgaa tccatcttaa  31860
gactgcagac atgggatgaa atgaaatttg gaaagacggt aagtctcttt ttctgtgcta  31920
ctcttatgga atctgactag aaataacaaa tgaccatggt tggtcctgag tgtgtgtgtg  31980
tgtgtgtgtg tggtatgtgt ttgtggccat gtgcatttat ttatctttgt gtgctagttt  32040
tggccattca aataaccttt ctgttcgcat gtaggttcac cgcatacagg tgaatgaaaa  32100
actcctcaga gacagtcagc acaaaccaca acctgttcct gacaaagaaa acaagaaact  32160
gctgtgtgga aagtgcaaga attttgcgtg ctacacagct gacattcgag tggttgaggt  32220
gagtggccct ggtgatttag caccggttaa atcttaccat cttccggaga aatggttgta  32280
gcaagaacac tatgttgtgg ggtttcgagt gttgaccatg gtcctgtatt aagaaataaa  32340
atcctgctag gtggtggtgg cacacgcctt taatcccagt acttgggagg cagaggcagg  32400
cggatttctg agttcgaggc cagcctggtc tacagggtga gttccaggac agccagggct  32460
acacagagaa accctgtctt ggaaaaacca aaaaaaaaaa aaaaaaaaag aaataaaatc  32520
ctgcttctat gtgggaacca gaaaggctga tgttatttaa gtccaaaaca gaaaatggtg  32580
cttaacggcg agaagaggag gggggtctaa ttgtagctgc cccagacagt caggcaggat  32640
ggataaggtt tcccgttcca ctgcacagca gggtgaatac tgcttatagt ttctgattca  32700
ttacaactct tacaaagaat tagacgagag gaattcatag cttcagacat aaagagatga  32760
aaactgtcca ggcagaaggg aatgctaatt actctggcga gatcattaga tacttagaaa  32820
ttatcacact gcacaccccta agtgaggaca actgtgtgct ttgaaagaca gtctcactca  32880
gaccaggctg gcttcaactt gagattcttc tgtgactcag cctcccccagt gcagggactc  32940
taggcatgca ccaccactct ctccaaagag atagtttttc ccagtgcagg gatagaaaat  33000
gaaggctctg ctagatacag tgttatgtcc ttggttagtt ccagggagga ggaagggcta  33060
ggcataaaaa tctgtcattg atttcttagt tttaacaaat gtgcaactgc attcaaaatg  33120
gaactgggct aaaggcattt gcaaatcttc tgaggcatct ctgtaacttt actgtatgtc  33180
aaagattatg ccaaagaaat gttaaggctc tgattttgaa gtgtacatgg ttctagtata  33240
aacctgccag caaatgaatg gtaaagtggg aaaatactat gaatatgaaa ttataaagat  33300
gcttttgtta tggctacata caacatgagc agtgatatct ttgtcatgac caatgtgggt  33360
ccacctttcc taaaggggaa aaaaggctaa tatataaaaa tgacatattc tgctagtgaa  33420
ttctctcttc ctgttttgtt ttctaaactt ccttattgga acagagaatg cttttataat  33480
gaaaacaaaa cacctcattt taaaaaatat aacacttgta ggttagcttt ctacttttttc  33540
acccccttaaa cttttttttt tttttttga gacaggatct ctctctatag cactgggtat  33600
```

-continued

```
cttgaaactc attatatgga gattcccttg tccctgcctc ccaaacgctg ggacgtaaag  33660
gcatgtacca ttacacaagg tcttcttaaa acttttaact aaggcaaaaa acctccagag  33720
acgaatcttg cagtcatcat tcctgctacc gatggcgggg gcagatggct gtgctagcta  33780
ggggaggggt acagtcctta ttatgagtga catccacttt ctgagtctga ttctttagat  33840
gcagaaggtc ctttcagctc caaattcaag gcttctcctt cccagtggcc tggagaacga  33900
gatgcttggt ctgcgcttgc gtctgtaggg tacactcttt ttttttaat tggatattt  33960
ctttatttac ataaagaaca ccttcagttc ccctacactg gggcatctaa gccttcatag  34020
gaccaaggac ctctcttccc attgatgcat gacaaggcca tcctctgcaa cgcacgcagc  34080
tggagccatg tgtactcctt tgtggatggc ttagtcgctg ggagctcttg ggggactggt  34140
tggttgatat tgtttttctc cctgtggggt tccttcagtt gtagggtact ctcttaagtc  34200
aagtctaagt ggggtctgtg gacagcatgg ctcctgagcc tgttcacaca catacccctgt  34260
gacccctggg tgtcaccagc cctgtgcttt ggtgccttcc tggcctctgg tgaacttgaa  34320
ctttgtatgt gaactcctct ttgcttctga gttggaaagc tgggtttcct cctttctcag  34380
gtgccagacg cccaggaaat gggtcctaat cggcctgggg aagactgtct atatagtttt  34440
tttttcttcc aacttgtaaa ataaatggga tcccactcat tcctgacttt tagctactga  34500
gtggcttcta agtcattttc agacccgttt ctaacattgt gcgctccatc tcttcctcct  34560
agacgtccca ctacactgtc cttggagacg cttttaagga gcgctttgtg tgtaagccac  34620
accctaaacc aaagatctat gacaattttg agaagaaagc aaagatattc tgcgccaaac  34680
agaactgtag ccacgactgg ggaatttttg tgagatacaa gacgttcgag attccagtca  34740
taaaaattga aagtttcgtc gtggaagata ttgtgagcgg agttcagaac cggcactcaa  34800
agtggaagga ctttcatttt gaaaggatac agttcgatcc tgcagaaatg tccgtatgac  34860
ctcaggcttc tccgtctcgt gccgcaggga gccgtgcctt aagcatggag ttgatgagcc  34920
aatgctttct tacccaagct tgcacaatcc tttcttacac aagcctgcac tgtgttgaat  34980
gccagataac ctgactggtt ggtttcaagc tggtgctgtc cacacaaagc acacacgcct  35040
gaactgcggc gccgaatagt ttcttcacca ataactcata gcgtagccct tggccatggt  35100
ggggaggggt taaacttgtc ccttttacac ttttcagaac tgcccgacag ggaacgtgca  35160
gccactcggt acaccgagac gcatgatggc tggcgtgctg gaagggttcc cgttctctgt  35220
ctgctcgatc tgctgtaagc tgcctttgcc cttaatgaca gtgcccttaa gaacagtgac  35280
ttagttcttt ttcaggccac cagactgact gccagatccc ttctgtccct tctgtccctt  35340
gcactgattc ctttccggat ttgaccctgc caccctgtca ccctctgcag agtctcctgg  35400
tttctgtctc ttccttggtt tctttgctga ctcaaatttg gtagttgcaa ggttcagtat  35460
gcacacatat atatttaaaa tgacatataa tttaaaatgt aaaagactat agttgacagc  35520
tatgcttact gagatggtat ttctgttctg ttcattacta tacatcttac ccttgctctc  35580
atctgttctt ttaacttggg ccatttcccg tctttgaata gacatctcaa accctgtctg  35640
tatgtctgtc tgtttcccac ctgtttgaga cagggtctct ctgtagacca gaaactccat  35700
atgtagacta tgctggcctt gaactcacag atccccctgc ctctcaagtg ttgaaattaa  35760
aatctttcac catgcctggc tctagctatt ttcaataaag gctcatgttt aaagtttgaa  35820
ctacttccaa ttcattccct gacgtggctt gttgttgttg tttacttttg gagacactgt  35880
tcctctctgt agccctggct gtgtagacca ggctgccctt ggtcacagag atctgccagc  35940
ttctgcctcc ggagcactga gattgaaggc ctgcatcacc atgcctggct tgccctttct  36000
tcttaaacat tatatattca aatggcattt ccgtgtttct tctcaaggtg tgccagtgct  36060
tcagagagct tagtttgggg ttcttcagat caagagacaa gtgtctgagc gctgttactg  36120
ccaacagagc aaagtactct tcagttcagg gaaggaacag tgctggtttt gtaggcagta  36180
cagtggtttt aacaccttcc tagaacttac ttgtaattca tcagttgtag accatcaatg  36240
gcctaaacca aactgcagag atcatctgac cacataactc cccttccagg acatttacat  36300
ttgaagacta tcccaagccc acccagagca cagtgggtta cccaaactcc ccaggtcaac  36360
cctggaggtc aacagtatga catgggatag cacaccactt ctcacagatg cctagagaaa  36420
ttacccagca acataactct ttggggaaaa aacacctata gggattaggc ttttaattga  36480
tagaataggt agaaaaaaag atatgtagta gttcttgata gtggttactg gtaaaattct  36540
tagtgcaata aaatgaattt gccgagagct gactttcttt tttttcttgt tttttgaga  36600
cagggtttct ctgtatagct ttggctgtcc tggaatgcac tctgtagtcc aggctggcct  36660
tcgaactcag aaatccgcct tcctctgcct cccaagtgtt gggattaaag gcgtgcgcca  36720
ccacgcctgg ctgagagctg actttcattt atgtctttta gtctatgttg cctttctttg  36780
ctgctacagt ttaagaactc tacagcttgt ataagatacc tactggaaat tatttgagaa  36840
aaaaaacttg taaacattac aataatttaa ttaattaaaa atttatgtat tttatgtata  36900
tgggtgtttt tttctgcaag tctgtgtgca cattagaaga gggcattgga tcctctctat  36960
tgttatagtt ttatgctgct gctgttgttg ctgtgtgtgt gtgtgtgtgt gtgtgctatg  37020
aattgaactc aggacctctg gaagagcagt cagtgctctt aactgctgag ctatctctcc  37080
agtcctggca atgataaatc agttgaagtg aaatagtcct cccccccctt tttttttttt  37140
gccaatgggg aaaagcagac taaatctgag accaaatgaa gttttgagtt gtacactgac  37200
ttaagccact gccaagcata ccctggaatg gagcaaaccc tgggttacta agtactgaat  37260
gaatacaaca ggaaggtttt gagagatggg aaaatgcttg tctttggact tccctgatgg  37320
aagttgcatc tggactctcc catgagcaca tcaccagtcc ccactagagt cctcacaggt  37380
tgccatccat gtgtcctttt tgaggctgag atacaacttg ttctgcaacc acagaccttg  37440
ctgttttgtg gtcagtattg gtatcatagc attttcatcc tgacctggag ccttcagtca  37500
aaggcctcat tgtgcagtaa ggacgctgga ctcctgactc ctatacttaa aacagacttg  37560
gtaatttcaa acaagtcaac cagatgccag tatttctgca tgcatgtctt gtgggatggt  37620
gttgtgaggt cccctgacag atgcactgag tggccaggga gacttttgta ccctttttcca  37680
ttttaacagc ccacgggtca ctgtgttgct tccatcatat taacatcaac ttgaaccagt  37740
ggttcctgaa acacttcagt tcattggacc ttgctaatta gcatcctgta aaaacccacc  37800
aacaaatatc aactagacag gtagaatcca agtgaactgt acactcctgg atcatgccag  37860
taactgtttt aataatacac cataaaatat aactacgact tcattttaca aatctgtgtt  37920
taataaacag gtacaggctt gttgggtgcg aacttttaaa actcctaata aaaatgccag  37980
ctatgattat ctttgtttat g                                            38001
```

```
SEQ ID NO: 12          moltype = RNA  length = 3435
FEATURE                Location/Qualifiers
source                 1..3435
                       mol_type = mRNA
```

```
                        organism = rattus norvegicus
SEQUENCE: 12
cgtttgtagt gtcagccatc ccaattgcct gttccttctc tgtgggagtg gtgtctagac  60
agtccaggca gggtatgcta ggcaggtgcg ttttggttgc ctcagatcgc aacttgactc  120
cataacggtg accaaagaca aaagaaggaa accagattaa aaagaaccgg acacagaccc  180
ctgcagaatc tggagcggcc gtggttgggg gcggggctac gacggggcgg actcgggggc  240
gtgggagggc ggggccgggg cggggcccgg agccggctgc ggttgcggtc cctgcgccgg  300
cggtgaaggc gcagcggcgg cgagtggcta ttgcaagcgt ttggataatg tgagacctgg  360
gatgcaggga tgtcgactat ctgcccccca ccatctcctg ctgttgccaa gacagagatt  420
gctttaagtg gtgaatcacc cttgttggcg gctacctttg cttactggga taatattctt  480
ggtcctagag taaggcacat ttgggctcca aagacagacc aagtactcct cagtgatgga  540
gaaatcactt ttcttgccaa ccacactctg aatggagaaa ttcttcggaa tgcggagagt  600
ggggcaatag atgtaaagtt ttttgtctta tctgaaaagg gcgtcattat tgtttcatta  660
atcttcgacg ggaactggaa cggagatcgg agcacttacg gactatcaat tatactgccg  720
cagacggagc tgagtttcta cctcccactg cacagagtgt gtgttgacag gctaacgcac  780
atcattcgaa aaggaaggat atggatgcac aaggaaagac aagaaaatgt ccagaaaatt  840
gtcttggaag gcaccgagag gatggaagat cagggtcaga gtatcatccc tatgcttact  900
ggggaggtca tccctgtgat ggagctgctt gcgtctatga gatcacacag tgttcctgaa  960
gacctcgata tagctgatac agtactcaat gatgatgaca ttggtgacag ctgtcatgaa  1020
ggctttcttc tcaatgccat cagctcacat ctgcagacct gcggctgttc tgtggtggta  1080
ggcagcagtg cagagaaagt aaataagata gtaagaacac tgtgcctttt tctgacacca  1140
gcagagagga agtgctccag gctgtgtgaa gccgaatcgt cctttaaata cgaatctgga  1200
ctctttgtac aaggcttgct aaaggatgcg actggcagtt ttgtactacc tttccggcaa  1260
gttatgtatg ccccttatcc caccacacac atcgatgtgg atgtcaacac tgtcaagcag  1320
atgccaccgt gtcatgaaca tatttataat caacgcagat acatgaggtc agagctgaca  1380
gccttctgga gggcaacttc agaagaggac atggctcagg acaccatcat ctacacagat  1440
gagagcttca ctcctgattt gaatattttc caagatgtct tacacagaga cactctagtg  1500
aaagcctttc tggatcaggt cttccatttg aagcctggcc tgtctctcag gagtactttc  1560
cttgcacagt tcctcctcat tcttcacaga aaagccttga cactaatcaa gtacatagag  1620
gatgacacgc agaaggggaa aaagcccttt aagtctcttc ggaacctgaa gatagatctt  1680
gatttaacag cagagggcga ccttaacata ataatggctc tagctgagaa aattaagcca  1740
ggcctacact ctttcatctt cgggagacct ttctacacta gtgtccaaga acgtgatgtt  1800
ctaatgactt tttaaacatg tggtttgctc cgtgtgtctc atgacagtca cacttgctgt  1860
tacagtgtct cagcgctttg gacacatcct tcctccaggg tcctgccgca ggacacgtta  1920
cactacactt gtcagtagag gtctgtacca gatgtcaggt acatcgttgt agtgaatgtc  1980
tcttttccta gactagatgt accctcgtag ggacttatgt ttacaaccct cctaagtact  2040
agtgctgtct tgtaaggata cgaatgaagg gatgtaaact tcaccacaac tgctggttgg  2100
ttttgttgtt tttgtttttt gaaacttata attcatggtt tacatgcatc acactgaaac  2160
cctagttagc tttttacagg taagctgtga gttgactgcc tgtccctgtg ttctctggcc  2220
tgtacgatct gtggcgtgta ggatcacttt tgcaacaact aaaaactaaa gcactttgtt  2280
tgcagttcta cagaaagcaa cttagtctgt ctgcagattc gtttttgaaa gaagacatga  2340
gaaagcggag ttttaggtga agtcagttgt tggatcttcc tttatagact tagtccttta  2400
gatgtggtct gtatagacat gcccaaccat catgcatggg cactgaatat cgtgaactgt  2460
ggtatgcttt ttgttggttt attgtacttc tgtcaaagaa agtggcattg gtttttataa  2520
ttgttgccaa gttttaaggt taattttcat tatttttgag ccaaattaaa atgtgcacct  2580
cctgtgcctt tcccaatctt ggaaaatata atttcttggc agaaggtcag atttcagggc  2640
ccagtcactt tcgtctgact tccctttgca cagtccgcca tgggcctggc ttagaagttc  2700
ttgtaaacta tgccagagag tacattcgct gataaaatct tctttgcaga gcaggagagc  2760
ttcttgcctc tttcctttca tttctgcctg gactttggtg ttctccacgt tccctgcatc  2820
ctaaggacag caggagaact ctgaccccag tgctatttct ctaggtgcta ttgtggcaaa  2880
ctcaagcggt ccgtctctgt ccctgtaacg ttcgtacctt gctggctgtg aagtactgac  2940
tggtaaagct ccgtgctaca gcagtgtagg gtatacacaa acacaagtaa gtgttttatt  3000
taaaactgtg gacttagcat aaaaagggag actatattta ttttttacaa aagggataaa  3060
aatggaaccc tttcctcacc caccagattt agtcagaaaa aaacattcta ttctgaaagg  3120
tcacagtggt tttgacatga cacatcagaa caacgcacac tgtccatgat ggcttatgaa  3180
ctccaagtca ctccatcatg gtaaatgggt agatccctcc ttctagtgtg ccacaccatt  3240
gcttcccaca gtagaatctt atttaagtgc taagtgttgt ctctgctggt ttactctgtt  3300
gttttagaga atgtaagttg tatagtgaat aagttattga agcatgtgta aacactgtta  3360
tacatctttt ctcctagatg gggaatttgg aataaaatac ctttaaaatt caaaaaaaaa  3420
aaaaaaaaaa aaaaa                                                   3435

SEQ ID NO: 13           moltype = RNA  length = 36
FEATURE                 Location/Qualifiers
source                  1..36
                        mol_type = other RNA
                        note = 6 nucleotide repeat from intron1 of c9orf72
                        organism = Homo sapiens
SEQUENCE: 13
ggggccgggg ccggggccgg ggccggggcc ggggcc                            36

SEQ ID NO: 14           moltype =   length =
SEQUENCE: 14
000

SEQ ID NO: 15           moltype = DNA  length = 22
FEATURE                 Location/Qualifiers
source                  1..22
                        mol_type = other DNA
                        organism = synthetic construct
```

```
SEQUENCE: 15
tgtgacagtt ggaatgcagt ga                                          22

SEQ ID NO: 16          moltype = DNA  length = 25
FEATURE                Location/Qualifiers
source                 1..25
                       mol_type = other DNA
                       organism = synthetic construct
SEQUENCE: 16
gccacttaaa gcaatctctg tcttg                                       25

SEQ ID NO: 17          moltype = DNA  length = 21
FEATURE                Location/Qualifiers
source                 1..21
                       mol_type = other DNA
                       organism = synthetic construct
SEQUENCE: 17
tcgactcttt gcccaccgcc a                                           21

SEQ ID NO: 18          moltype = DNA  length = 20
FEATURE                Location/Qualifiers
source                 1..20
                       mol_type = other DNA
                       organism = synthetic construct
SEQUENCE: 18
gggtctagca agagcaggtg                                             20

SEQ ID NO: 19          moltype = DNA  length = 21
FEATURE                Location/Qualifiers
source                 1..21
                       mol_type = other DNA
                       organism = synthetic construct
SEQUENCE: 19
gtcttggcaa cagctggaga t                                           21

SEQ ID NO: 20          moltype = DNA  length = 24
FEATURE                Location/Qualifiers
source                 1..24
                       mol_type = other DNA
                       organism = synthetic construct
SEQUENCE: 20
tgatgtcgac tctttgccca ccgc                                        24

SEQ ID NO: 21          moltype = DNA  length = 22
FEATURE                Location/Qualifiers
source                 1..22
                       mol_type = other DNA
                       organism = synthetic construct
SEQUENCE: 21
tcctgtaatg gaactgcttt ca                                          22

SEQ ID NO: 22          moltype = DNA  length = 22
FEATURE                Location/Qualifiers
source                 1..22
                       mol_type = other DNA
                       organism = synthetic construct
SEQUENCE: 22
ggtatctgct tcatccagct tt                                          22

SEQ ID NO: 23          moltype = DNA  length = 16
FEATURE                Location/Qualifiers
source                 1..16
                       mol_type = other DNA
                       organism = synthetic construct
SEQUENCE: 23
ccccggcccc ggcccc                                                 16

SEQ ID NO: 24          moltype = DNA  length = 20
FEATURE                Location/Qualifiers
source                 1..20
                       mol_type = other DNA
                       organism = synthetic construct
SEQUENCE: 24
caagccaccg tctcactcaa                                             20

SEQ ID NO: 25          moltype = DNA  length = 28
FEATURE                Location/Qualifiers
source                 1..28
                       mol_type = other DNA
```

```
                        organism = synthetic construct
SEQUENCE: 25
gtagtgctgt ctactccaga gagttacc                                      28

SEQ ID NO: 26           moltype = DNA  length = 30
FEATURE                 Location/Qualifiers
source                  1..30
                        mol_type = other DNA
                        organism = synthetic construct
SEQUENCE: 26
cttggcttcc ctcaaaagac tggctaatgt                                    30

SEQ ID NO: 27           moltype =   length =
SEQUENCE: 27
000

SEQ ID NO: 28           moltype =   length =
SEQUENCE: 28
000

SEQ ID NO: 29           moltype =   length =
SEQUENCE: 29
000

SEQ ID NO: 30           moltype = DNA  length = 20
FEATURE                 Location/Qualifiers
source                  1..20
                        mol_type = other DNA
                        organism = synthetic construct
SEQUENCE: 30
agcgggacac cgtaggttac                                               20

SEQ ID NO: 31           moltype = DNA  length = 20
FEATURE                 Location/Qualifiers
source                  1..20
                        mol_type = other DNA
                        organism = synthetic construct
SEQUENCE: 31
gtgggcggaa cttgtcgctg                                               20

SEQ ID NO: 32           moltype = DNA  length = 20
FEATURE                 Location/Qualifiers
source                  1..20
                        mol_type = other DNA
                        organism = synthetic construct
SEQUENCE: 32
gtcacattat ccaaatgctc                                               20

SEQ ID NO: 33           moltype = DNA  length = 20
FEATURE                 Location/Qualifiers
source                  1..20
                        mol_type = other DNA
                        organism = synthetic construct
SEQUENCE: 33
ggtgggcaaa gagtcgacat                                               20

SEQ ID NO: 34           moltype = DNA  length = 20
FEATURE                 Location/Qualifiers
source                  1..20
                        mol_type = other DNA
                        organism = synthetic construct
SEQUENCE: 34
atctctgtct tggcaacagc                                               20

SEQ ID NO: 35           moltype = DNA  length = 20
FEATURE                 Location/Qualifiers
source                  1..20
                        mol_type = other DNA
                        organism = synthetic construct
SEQUENCE: 35
aagcaatctc tgtcttggca                                               20

SEQ ID NO: 36           moltype = DNA  length = 20
FEATURE                 Location/Qualifiers
source                  1..20
                        mol_type = other DNA
                        organism = synthetic construct
SEQUENCE: 36
acttaaagca atctctgtct                                               20
```

```
SEQ ID NO: 37          moltype = DNA  length = 20
FEATURE                Location/Qualifiers
source                 1..20
                       mol_type = other DNA
                       organism = synthetic construct
SEQUENCE: 37
ttgccactta aagcaatctc                                              20

SEQ ID NO: 38          moltype = DNA  length = 20
FEATURE                Location/Qualifiers
source                 1..20
                       mol_type = other DNA
                       organism = synthetic construct
SEQUENCE: 38
cccagtaagc aaaagtagct                                              20

SEQ ID NO: 39          moltype = DNA  length = 20
FEATURE                Location/Qualifiers
source                 1..20
                       mol_type = other DNA
                       organism = synthetic construct
SEQUENCE: 39
actctaggac caagaatatt                                              20

SEQ ID NO: 40          moltype = DNA  length = 20
FEATURE                Location/Qualifiers
source                 1..20
                       mol_type = other DNA
                       organism = synthetic construct
SEQUENCE: 40
gccttactct aggaccaaga                                              20

SEQ ID NO: 41          moltype = DNA  length = 20
FEATURE                Location/Qualifiers
source                 1..20
                       mol_type = other DNA
                       organism = synthetic construct
SEQUENCE: 41
ccaaatgtgc cttactctag                                              20

SEQ ID NO: 42          moltype = DNA  length = 20
FEATURE                Location/Qualifiers
source                 1..20
                       mol_type = other DNA
                       organism = synthetic construct
SEQUENCE: 42
tggagcccaa atgtgcctta                                              20

SEQ ID NO: 43          moltype = DNA  length = 20
FEATURE                Location/Qualifiers
source                 1..20
                       mol_type = other DNA
                       organism = synthetic construct
SEQUENCE: 43
tctgtctttg gagcccaaat                                              20

SEQ ID NO: 44          moltype = DNA  length = 20
FEATURE                Location/Qualifiers
source                 1..20
                       mol_type = other DNA
                       organism = synthetic construct
SEQUENCE: 44
ccatcactga gaagtacctg                                              20

SEQ ID NO: 45          moltype = DNA  length = 20
FEATURE                Location/Qualifiers
source                 1..20
                       mol_type = other DNA
                       organism = synthetic construct
SEQUENCE: 45
atttctccat cactgagaag                                              20

SEQ ID NO: 46          moltype = DNA  length = 20
FEATURE                Location/Qualifiers
source                 1..20
                       mol_type = other DNA
                       organism = synthetic construct
SEQUENCE: 46
```

```
aaaagttatt tctccatcac                                              20

SEQ ID NO: 47          moltype = DNA  length = 20
FEATURE                Location/Qualifiers
source                 1..20
                       mol_type = other DNA
                       organism = synthetic construct
SEQUENCE: 47
tggcaagaaa agttatttct                                              20

SEQ ID NO: 48          moltype = DNA  length = 20
FEATURE                Location/Qualifiers
source                 1..20
                       mol_type = other DNA
                       organism = synthetic construct
SEQUENCE: 48
gtgtggttgg caagaaaagt                                              20

SEQ ID NO: 49          moltype = DNA  length = 20
FEATURE                Location/Qualifiers
source                 1..20
                       mol_type = other DNA
                       organism = synthetic construct
SEQUENCE: 49
ctccatttag agtgtggttg                                              20

SEQ ID NO: 50          moltype = DNA  length = 20
FEATURE                Location/Qualifiers
source                 1..20
                       mol_type = other DNA
                       organism = synthetic construct
SEQUENCE: 50
tgcatttcga aggatttctc                                              20

SEQ ID NO: 51          moltype = DNA  length = 20
FEATURE                Location/Qualifiers
source                 1..20
                       mol_type = other DNA
                       organism = synthetic construct
SEQUENCE: 51
ccactctctg catttcgaag                                              20

SEQ ID NO: 52          moltype = DNA  length = 20
FEATURE                Location/Qualifiers
source                 1..20
                       mol_type = other DNA
                       organism = synthetic construct
SEQUENCE: 52
acaaaaaact ttacatctat                                              20

SEQ ID NO: 53          moltype = DNA  length = 20
FEATURE                Location/Qualifiers
source                 1..20
                       mol_type = other DNA
                       organism = synthetic construct
SEQUENCE: 53
ccttttcaga caagacaaaa                                              20

SEQ ID NO: 54          moltype = DNA  length = 20
FEATURE                Location/Qualifiers
source                 1..20
                       mol_type = other DNA
                       organism = synthetic construct
SEQUENCE: 54
aagattaatg aaacaataat                                              20

SEQ ID NO: 55          moltype = DNA  length = 20
FEATURE                Location/Qualifiers
source                 1..20
                       mol_type = other DNA
                       organism = synthetic construct
SEQUENCE: 55
gtttccatca aagattaatg                                              20

SEQ ID NO: 56          moltype = DNA  length = 20
FEATURE                Location/Qualifiers
source                 1..20
                       mol_type = other DNA
                       organism = synthetic construct
```

-continued

```
SEQUENCE: 56
attgatagtc catatgtgct                                             20

SEQ ID NO: 57          moltype = DNA  length = 20
FEATURE                Location/Qualifiers
source                 1..20
                       mol_type = other DNA
                       organism = synthetic construct
SEQUENCE: 57
agtataattg atagtccata                                             20

SEQ ID NO: 58          moltype = DNA  length = 20
FEATURE                Location/Qualifiers
source                 1..20
                       mol_type = other DNA
                       organism = synthetic construct
SEQUENCE: 58
ggaggtagaa actaagttct                                             20

SEQ ID NO: 59          moltype = DNA  length = 20
FEATURE                Location/Qualifiers
source                 1..20
                       mol_type = other DNA
                       organism = synthetic construct
SEQUENCE: 59
atgtgttaat ctatcaacac                                             20

SEQ ID NO: 60          moltype = DNA  length = 20
FEATURE                Location/Qualifiers
source                 1..20
                       mol_type = other DNA
                       organism = synthetic construct
SEQUENCE: 60
tgcatccata ttcttccttt                                             20

SEQ ID NO: 61          moltype = DNA  length = 20
FEATURE                Location/Qualifiers
source                 1..20
                       mol_type = other DNA
                       organism = synthetic construct
SEQUENCE: 61
ttccttatgc atccatattc                                             20

SEQ ID NO: 62          moltype = DNA  length = 20
FEATURE                Location/Qualifiers
source                 1..20
                       mol_type = other DNA
                       organism = synthetic construct
SEQUENCE: 62
cttgtctttc cttatgcatc                                             20

SEQ ID NO: 63          moltype = DNA  length = 20
FEATURE                Location/Qualifiers
source                 1..20
                       mol_type = other DNA
                       organism = synthetic construct
SEQUENCE: 63
acattttctt gtctttcctt                                             20

SEQ ID NO: 64          moltype = DNA  length = 20
FEATURE                Location/Qualifiers
source                 1..20
                       mol_type = other DNA
                       organism = synthetic construct
SEQUENCE: 64
tctggacatt ttcttgtctt                                             20

SEQ ID NO: 65          moltype = DNA  length = 20
FEATURE                Location/Qualifiers
source                 1..20
                       mol_type = other DNA
                       organism = synthetic construct
SEQUENCE: 65
ataatcttct ggacattttc                                             20

SEQ ID NO: 66          moltype = DNA  length = 20
FEATURE                Location/Qualifiers
source                 1..20
                       mol_type = other DNA
```

```
                        organism = synthetic construct
SEQUENCE: 66
ctctgaccct gatcttccat                                                20

SEQ ID NO: 67           moltype = DNA  length = 20
FEATURE                 Location/Qualifiers
source                  1..20
                        mol_type = other DNA
                        organism = synthetic construct
SEQUENCE: 67
ttggaataat actctgaccc                                                20

SEQ ID NO: 68           moltype = DNA  length = 20
FEATURE                 Location/Qualifiers
source                  1..20
                        mol_type = other DNA
                        organism = synthetic construct
SEQUENCE: 68
cagttccatt acaggaatca                                                20

SEQ ID NO: 69           moltype = DNA  length = 20
FEATURE                 Location/Qualifiers
source                  1..20
                        mol_type = other DNA
                        organism = synthetic construct
SEQUENCE: 69
cttcaggaac actgtgtgat                                                20

SEQ ID NO: 70           moltype = DNA  length = 20
FEATURE                 Location/Qualifiers
source                  1..20
                        mol_type = other DNA
                        organism = synthetic construct
SEQUENCE: 70
atctatttct tcaggaacac                                                20

SEQ ID NO: 71           moltype = DNA  length = 20
FEATURE                 Location/Qualifiers
source                  1..20
                        mol_type = other DNA
                        organism = synthetic construct
SEQUENCE: 71
agtactgtat cagctatatc                                                20

SEQ ID NO: 72           moltype = DNA  length = 20
FEATURE                 Location/Qualifiers
source                  1..20
                        mol_type = other DNA
                        organism = synthetic construct
SEQUENCE: 72
tcattgagta ctgtatcagc                                                20

SEQ ID NO: 73           moltype = DNA  length = 20
FEATURE                 Location/Qualifiers
source                  1..20
                        mol_type = other DNA
                        organism = synthetic construct
SEQUENCE: 73
tcatcatcat tgagtactgt                                                20

SEQ ID NO: 74           moltype = DNA  length = 20
FEATURE                 Location/Qualifiers
source                  1..20
                        mol_type = other DNA
                        organism = synthetic construct
SEQUENCE: 74
ccaatatcat catcattgag                                                20

SEQ ID NO: 75           moltype = DNA  length = 20
FEATURE                 Location/Qualifiers
source                  1..20
                        mol_type = other DNA
                        organism = synthetic construct
SEQUENCE: 75
tcatgacagc tgtcaccaat                                                20

SEQ ID NO: 76           moltype = DNA  length = 20
FEATURE                 Location/Qualifiers
source                  1..20
```

```
                        mol_type = other DNA
                        organism = synthetic construct
SEQUENCE: 76
aagccttcat gacagctgtc                                                   20

SEQ ID NO: 77           moltype = DNA  length = 20
FEATURE                 Location/Qualifiers
source                  1..20
                        mol_type = other DNA
                        organism = synthetic construct
SEQUENCE: 77
agaagaaagc cttcatgaca                                                   20

SEQ ID NO: 78           moltype = DNA  length = 20
FEATURE                 Location/Qualifiers
source                  1..20
                        mol_type = other DNA
                        organism = synthetic construct
SEQUENCE: 78
tacttgagaa gaaagccttc                                                   20

SEQ ID NO: 79           moltype = DNA  length = 20
FEATURE                 Location/Qualifiers
source                  1..20
                        mol_type = other DNA
                        organism = synthetic construct
SEQUENCE: 79
attcttactt gagaagaaag                                                   20

SEQ ID NO: 80           moltype = DNA  length = 20
FEATURE                 Location/Qualifiers
source                  1..20
                        mol_type = other DNA
                        organism = synthetic construct
SEQUENCE: 80
aaaaattctt acttgagaag                                                   20

SEQ ID NO: 81           moltype = DNA  length = 20
FEATURE                 Location/Qualifiers
source                  1..20
                        mol_type = other DNA
                        organism = synthetic construct
SEQUENCE: 81
agatggtatc tgcttcatcc                                                   20

SEQ ID NO: 82           moltype = DNA  length = 20
FEATURE                 Location/Qualifiers
source                  1..20
                        mol_type = other DNA
                        organism = synthetic construct
SEQUENCE: 82
caatctaagt agacagtctg                                                   20

SEQ ID NO: 83           moltype = DNA  length = 20
FEATURE                 Location/Qualifiers
source                  1..20
                        mol_type = other DNA
                        organism = synthetic construct
SEQUENCE: 83
ttaagcaaca gttcaaatac                                                   20

SEQ ID NO: 84           moltype = DNA  length = 20
FEATURE                 Location/Qualifiers
source                  1..20
                        mol_type = other DNA
                        organism = synthetic construct
SEQUENCE: 84
ctttaaatag caaatggaat                                                   20

SEQ ID NO: 85           moltype = DNA  length = 20
FEATURE                 Location/Qualifiers
source                  1..20
                        mol_type = other DNA
                        organism = synthetic construct
SEQUENCE: 85
gccatgattt cttgtctggg                                                   20

SEQ ID NO: 86           moltype = DNA  length = 20
FEATURE                 Location/Qualifiers
```

```
source                  1..20
                        mol_type = other DNA
                        organism = synthetic construct
SEQUENCE: 86
gctttaatga gaagtaaaac                                                20

SEQ ID NO: 87           moltype = DNA  length = 20
FEATURE                 Location/Qualifiers
source                  1..20
                        mol_type = other DNA
                        organism = synthetic construct
SEQUENCE: 87
tctacagtac aacttaatat                                                20

SEQ ID NO: 88           moltype = DNA  length = 20
FEATURE                 Location/Qualifiers
source                  1..20
                        mol_type = other DNA
                        organism = synthetic construct
SEQUENCE: 88
ataattttgt tctacgccta                                                20

SEQ ID NO: 89           moltype = DNA  length = 20
FEATURE                 Location/Qualifiers
source                  1..20
                        mol_type = other DNA
                        organism = synthetic construct
SEQUENCE: 89
cactgctgga tggaaaaaga                                                20

SEQ ID NO: 90           moltype = DNA  length = 20
FEATURE                 Location/Qualifiers
source                  1..20
                        mol_type = other DNA
                        organism = synthetic construct
SEQUENCE: 90
tggtttaagg gcacaaactc                                                20

SEQ ID NO: 91           moltype = DNA  length = 20
FEATURE                 Location/Qualifiers
source                  1..20
                        mol_type = other DNA
                        organism = synthetic construct
SEQUENCE: 91
ttgcccacgg gtacacagca                                                20

SEQ ID NO: 92           moltype = DNA  length = 20
FEATURE                 Location/Qualifiers
source                  1..20
                        mol_type = other DNA
                        organism = synthetic construct
SEQUENCE: 92
cagatgagga aataggtgta                                                20

SEQ ID NO: 93           moltype = DNA  length = 20
FEATURE                 Location/Qualifiers
source                  1..20
                        mol_type = other DNA
                        organism = synthetic construct
SEQUENCE: 93
acacattagg tactattact                                                20

SEQ ID NO: 94           moltype = DNA  length = 20
FEATURE                 Location/Qualifiers
source                  1..20
                        mol_type = other DNA
                        organism = synthetic construct
SEQUENCE: 94
tttttatgtt ccaggcactg                                                20

SEQ ID NO: 95           moltype = DNA  length = 20
FEATURE                 Location/Qualifiers
source                  1..20
                        mol_type = other DNA
                        organism = synthetic construct
SEQUENCE: 95
aataggaaat gttagctatg                                                20

SEQ ID NO: 96           moltype = DNA  length = 20
```

```
FEATURE                Location/Qualifiers
source                 1..20
                       mol_type = other DNA
                       organism = synthetic construct
SEQUENCE: 96
ggcactcaac aaatactggc                                              20

SEQ ID NO: 97          moltype = DNA  length = 20
FEATURE                Location/Qualifiers
source                 1..20
                       mol_type = other DNA
                       organism = synthetic construct
SEQUENCE: 97
tacatgtaaa gcaactagta                                              20

SEQ ID NO: 98          moltype = DNA  length = 20
FEATURE                Location/Qualifiers
source                 1..20
                       mol_type = other DNA
                       organism = synthetic construct
SEQUENCE: 98
taaaatttca tgaaaatctg                                              20

SEQ ID NO: 99          moltype = DNA  length = 20
FEATURE                Location/Qualifiers
source                 1..20
                       mol_type = other DNA
                       organism = synthetic construct
SEQUENCE: 99
aagtgaatac tttatacttt                                              20

SEQ ID NO: 100         moltype = DNA  length = 20
FEATURE                Location/Qualifiers
source                 1..20
                       mol_type = other DNA
                       organism = synthetic construct
SEQUENCE: 100
catcatgagc ctaaaggaaa                                              20

SEQ ID NO: 101         moltype = DNA  length = 20
FEATURE                Location/Qualifiers
source                 1..20
                       mol_type = other DNA
                       organism = synthetic construct
SEQUENCE: 101
ggctcttagg ttaaacacac                                              20

SEQ ID NO: 102         moltype = DNA  length = 20
FEATURE                Location/Qualifiers
source                 1..20
                       mol_type = other DNA
                       organism = synthetic construct
SEQUENCE: 102
tgcttctgat tcaagccatt                                              20

SEQ ID NO: 103         moltype = DNA  length = 20
FEATURE                Location/Qualifiers
source                 1..20
                       mol_type = other DNA
                       organism = synthetic construct
SEQUENCE: 103
atacaggact aaagtgcttc                                              20

SEQ ID NO: 104         moltype = DNA  length = 20
FEATURE                Location/Qualifiers
source                 1..20
                       mol_type = other DNA
                       organism = synthetic construct
SEQUENCE: 104
caaatgggat ttaaaatgat                                              20

SEQ ID NO: 105         moltype = DNA  length = 20
FEATURE                Location/Qualifiers
source                 1..20
                       mol_type = other DNA
                       organism = synthetic construct
SEQUENCE: 105
tgacatgtag agagattaag                                              20
```

-continued

```
SEQ ID NO: 106          moltype = DNA  length = 20
FEATURE                 Location/Qualifiers
source                  1..20
                        mol_type = other DNA
                        organism = synthetic construct
SEQUENCE: 106
ttattgaaat accatcattt                                              20

SEQ ID NO: 107          moltype = DNA  length = 20
FEATURE                 Location/Qualifiers
source                  1..20
                        mol_type = other DNA
                        organism = synthetic construct
SEQUENCE: 107
tagtcagtat aatatcattt                                              20

SEQ ID NO: 108          moltype = DNA  length = 20
FEATURE                 Location/Qualifiers
source                  1..20
                        mol_type = other DNA
                        organism = synthetic construct
SEQUENCE: 108
gcattgagaa gaaagccttc                                              20

SEQ ID NO: 109          moltype = DNA  length = 20
FEATURE                 Location/Qualifiers
source                  1..20
                        mol_type = other DNA
                        organism = synthetic construct
SEQUENCE: 109
aagacctgat ccaggaaggc                                              20

SEQ ID NO: 110          moltype = DNA  length = 20
FEATURE                 Location/Qualifiers
source                  1..20
                        mol_type = other DNA
                        organism = synthetic construct
SEQUENCE: 110
tgagctgatg gcattgagaa                                              20

SEQ ID NO: 111          moltype = DNA  length = 20
FEATURE                 Location/Qualifiers
source                  1..20
                        mol_type = other DNA
                        organism = synthetic construct
SEQUENCE: 111
acaacggaac agccacaggt                                              20

SEQ ID NO: 112          moltype = DNA  length = 20
FEATURE                 Location/Qualifiers
source                  1..20
                        mol_type = other DNA
                        organism = synthetic construct
SEQUENCE: 112
ttagtgtcaa ggcttttctg                                              20

SEQ ID NO: 113          moltype = DNA  length = 20
FEATURE                 Location/Qualifiers
source                  1..20
                        mol_type = other DNA
                        organism = synthetic construct
SEQUENCE: 113
gacggctgac acaccaagcg                                              20

SEQ ID NO: 114          moltype = DNA  length = 20
FEATURE                 Location/Qualifiers
source                  1..20
                        mol_type = other DNA
                        organism = synthetic construct
SEQUENCE: 114
tgatggcatt gagaagaaag                                              20

SEQ ID NO: 115          moltype = DNA  length = 20
FEATURE                 Location/Qualifiers
source                  1..20
                        mol_type = other DNA
                        organism = synthetic construct
SEQUENCE: 115
tttactttct ctgcactgct                                              20
```

```
SEQ ID NO: 116          moltype = DNA  length = 20
FEATURE                 Location/Qualifiers
source                  1..20
                        mol_type = other DNA
                        organism = synthetic construct
SEQUENCE: 116
tcttatttac tttctctgca                                               20

SEQ ID NO: 117          moltype = DNA  length = 20
FEATURE                 Location/Qualifiers
source                  1..20
                        mol_type = other DNA
                        organism = synthetic construct
SEQUENCE: 117
ggcataatgt tctgactatc                                               20

SEQ ID NO: 118          moltype = DNA  length = 20
FEATURE                 Location/Qualifiers
source                  1..20
                        mol_type = other DNA
                        organism = synthetic construct
SEQUENCE: 118
ataacctgga gcattttctc                                               20

SEQ ID NO: 119          moltype = DNA  length = 20
FEATURE                 Location/Qualifiers
source                  1..20
                        mol_type = other DNA
                        organism = synthetic construct
SEQUENCE: 119
ccctgactca tatttaaatg                                               20

SEQ ID NO: 120          moltype = DNA  length = 20
FEATURE                 Location/Qualifiers
source                  1..20
                        mol_type = other DNA
                        organism = synthetic construct
SEQUENCE: 120
ccagttgaat cctttagcag                                               20

SEQ ID NO: 121          moltype = DNA  length = 20
FEATURE                 Location/Qualifiers
source                  1..20
                        mol_type = other DNA
                        organism = synthetic construct
SEQUENCE: 121
catacatgac ttgccggaaa                                               20

SEQ ID NO: 122          moltype = DNA  length = 20
FEATURE                 Location/Qualifiers
source                  1..20
                        mol_type = other DNA
                        organism = synthetic construct
SEQUENCE: 122
gacatccaca tctatgtgtg                                               20

SEQ ID NO: 123          moltype = DNA  length = 20
FEATURE                 Location/Qualifiers
source                  1..20
                        mol_type = other DNA
                        organism = synthetic construct
SEQUENCE: 123
tgttcatgac agggtggcat                                               20

SEQ ID NO: 124          moltype = DNA  length = 20
FEATURE                 Location/Qualifiers
source                  1..20
                        mol_type = other DNA
                        organism = synthetic construct
SEQUENCE: 124
ttataaatat gttcatgaca                                               20

SEQ ID NO: 125          moltype = DNA  length = 20
FEATURE                 Location/Qualifiers
source                  1..20
                        mol_type = other DNA
                        organism = synthetic construct
SEQUENCE: 125
```

```
cagctcggat ctcatgtatc                                              20

SEQ ID NO: 126          moltype = DNA  length = 20
FEATURE                 Location/Qualifiers
source                  1..20
                        mol_type = other DNA
                        organism = synthetic construct
SEQUENCE: 126
ctccagaagg ctgtcagctc                                              20

SEQ ID NO: 127          moltype = DNA  length = 20
FEATURE                 Location/Qualifiers
source                  1..20
                        mol_type = other DNA
                        organism = synthetic construct
SEQUENCE: 127
gtatcctgag ccatgtcttc                                              20

SEQ ID NO: 128          moltype = DNA  length = 20
FEATURE                 Location/Qualifiers
source                  1..20
                        mol_type = other DNA
                        organism = synthetic construct
SEQUENCE: 128
aatcaggagt aaagctttcg                                              20

SEQ ID NO: 129          moltype = DNA  length = 20
FEATURE                 Location/Qualifiers
source                  1..20
                        mol_type = other DNA
                        organism = synthetic construct
SEQUENCE: 129
aaaatattca aatcaggagt                                              20

SEQ ID NO: 130          moltype = DNA  length = 20
FEATURE                 Location/Qualifiers
source                  1..20
                        mol_type = other DNA
                        organism = synthetic construct
SEQUENCE: 130
tctctgtgta agacatcttg                                              20

SEQ ID NO: 131          moltype = DNA  length = 20
FEATURE                 Location/Qualifiers
source                  1..20
                        mol_type = other DNA
                        organism = synthetic construct
SEQUENCE: 131
gagtgtctct gtgtaagaca                                              20

SEQ ID NO: 132          moltype = DNA  length = 20
FEATURE                 Location/Qualifiers
source                  1..20
                        mol_type = other DNA
                        organism = synthetic construct
SEQUENCE: 132
cactagagtg tctctgtgta                                              20

SEQ ID NO: 133          moltype = DNA  length = 20
FEATURE                 Location/Qualifiers
source                  1..20
                        mol_type = other DNA
                        organism = synthetic construct
SEQUENCE: 133
gctttcacta gagtgtctct                                              20

SEQ ID NO: 134          moltype = DNA  length = 20
FEATURE                 Location/Qualifiers
source                  1..20
                        mol_type = other DNA
                        organism = synthetic construct
SEQUENCE: 134
gatccaggaa ggctttcact                                              20

SEQ ID NO: 135          moltype = DNA  length = 20
FEATURE                 Location/Qualifiers
source                  1..20
                        mol_type = other DNA
                        organism = synthetic construct
```

-continued

```
SEQUENCE: 135
aaagtacttc tgagagataa                                               20

SEQ ID NO: 136          moltype = DNA  length = 20
FEATURE                 Location/Qualifiers
source                  1..20
                        mol_type = other DNA
                        organism = synthetic construct
SEQUENCE: 136
aactgtgcaa ggaaagtact                                               20

SEQ ID NO: 137          moltype = DNA  length = 20
FEATURE                 Location/Qualifiers
source                  1..20
                        mol_type = other DNA
                        organism = synthetic construct
SEQUENCE: 137
gtcaaggctt ttctgtgaag                                               20

SEQ ID NO: 138          moltype = DNA  length = 20
FEATURE                 Location/Qualifiers
source                  1..20
                        mol_type = other DNA
                        organism = synthetic construct
SEQUENCE: 138
agagatttaa agggcttttt                                               20

SEQ ID NO: 139          moltype = DNA  length = 20
FEATURE                 Location/Qualifiers
source                  1..20
                        mol_type = other DNA
                        organism = synthetic construct
SEQUENCE: 139
atcttcaggt tccgaagaga                                               20

SEQ ID NO: 140          moltype = DNA  length = 20
FEATURE                 Location/Qualifiers
source                  1..20
                        mol_type = other DNA
                        organism = synthetic construct
SEQUENCE: 140
ccctctgctg ttaaatcaag                                               20

SEQ ID NO: 141          moltype = DNA  length = 20
FEATURE                 Location/Qualifiers
source                  1..20
                        mol_type = other DNA
                        organism = synthetic construct
SEQUENCE: 141
tgttaagatc gccctctgct                                               20

SEQ ID NO: 142          moltype = DNA  length = 20
FEATURE                 Location/Qualifiers
source                  1..20
                        mol_type = other DNA
                        organism = synthetic construct
SEQUENCE: 142
attattatgt taagatcgcc                                               20

SEQ ID NO: 143          moltype = DNA  length = 20
FEATURE                 Location/Qualifiers
source                  1..20
                        mol_type = other DNA
                        organism = synthetic construct
SEQUENCE: 143
agagccatta ttatgttaag                                               20

SEQ ID NO: 144          moltype = DNA  length = 20
FEATURE                 Location/Qualifiers
source                  1..20
                        mol_type = other DNA
                        organism = synthetic construct
SEQUENCE: 144
ataaaagagt gtaggcctgg                                               20

SEQ ID NO: 145          moltype = DNA  length = 20
FEATURE                 Location/Qualifiers
source                  1..20
                        mol_type = other DNA
```

-continued

```
                        organism = synthetic construct
SEQUENCE: 145
acactagtgt agaaaggtct                                              20

SEQ ID NO: 146          moltype = DNA  length = 20
FEATURE                 Location/Qualifiers
source                  1..20
                        mol_type = other DNA
                        organism = synthetic construct
SEQUENCE: 146
gttcttgcac actagtgtag                                              20

SEQ ID NO: 147          moltype = DNA  length = 20
FEATURE                 Location/Qualifiers
source                  1..20
                        mol_type = other DNA
                        organism = synthetic construct
SEQUENCE: 147
taaaaagtca ttagaacatc                                              20

SEQ ID NO: 148          moltype = DNA  length = 20
FEATURE                 Location/Qualifiers
source                  1..20
                        mol_type = other DNA
                        organism = synthetic construct
SEQUENCE: 148
tattaagtta cacatttaaa                                              20

SEQ ID NO: 149          moltype = DNA  length = 20
FEATURE                 Location/Qualifiers
source                  1..20
                        mol_type = other DNA
                        organism = synthetic construct
SEQUENCE: 149
ctttaccagc gatcatgatt                                              20

SEQ ID NO: 150          moltype = DNA  length = 20
FEATURE                 Location/Qualifiers
source                  1..20
                        mol_type = other DNA
                        organism = synthetic construct
SEQUENCE: 150
ttctggagta tgatccaggg                                              20

SEQ ID NO: 151          moltype = DNA  length = 20
FEATURE                 Location/Qualifiers
source                  1..20
                        mol_type = other DNA
                        organism = synthetic construct
SEQUENCE: 151
acttaactgc aattgctgag                                              20

SEQ ID NO: 152          moltype = DNA  length = 20
FEATURE                 Location/Qualifiers
source                  1..20
                        mol_type = other DNA
                        organism = synthetic construct
SEQUENCE: 152
tgtagtgtaa cttacttaac                                              20

SEQ ID NO: 153          moltype = DNA  length = 20
FEATURE                 Location/Qualifiers
source                  1..20
                        mol_type = other DNA
                        organism = synthetic construct
SEQUENCE: 153
atgcacctga catcccctca                                              20

SEQ ID NO: 154          moltype = DNA  length = 20
FEATURE                 Location/Qualifiers
source                  1..20
                        mol_type = other DNA
                        organism = synthetic construct
SEQUENCE: 154
cccaaaagca taaatctagg                                              20

SEQ ID NO: 155          moltype = DNA  length = 20
FEATURE                 Location/Qualifiers
source                  1..20
```

```
                        mol_type = other DNA
                        organism = synthetic construct
SEQUENCE: 155
atatttatta tattgtaaac                                                20

SEQ ID NO: 156          moltype = DNA  length = 20
FEATURE                 Location/Qualifiers
source                  1..20
                        mol_type = other DNA
                        organism = synthetic construct
SEQUENCE: 156
agcaataata tttattatat                                                20

SEQ ID NO: 157          moltype = DNA  length = 20
FEATURE                 Location/Qualifiers
source                  1..20
                        mol_type = other DNA
                        organism = synthetic construct
SEQUENCE: 157
agatagcaat aatatttatt                                                20

SEQ ID NO: 158          moltype = DNA  length = 20
FEATURE                 Location/Qualifiers
source                  1..20
                        mol_type = other DNA
                        organism = synthetic construct
SEQUENCE: 158
aaagatagca ataatattta                                                20

SEQ ID NO: 159          moltype = DNA  length = 20
FEATURE                 Location/Qualifiers
source                  1..20
                        mol_type = other DNA
                        organism = synthetic construct
SEQUENCE: 159
ttaaaagata gcaataatat                                                20

SEQ ID NO: 160          moltype = DNA  length = 20
FEATURE                 Location/Qualifiers
source                  1..20
                        mol_type = other DNA
                        organism = synthetic construct
SEQUENCE: 160
atctttaaaa gatagcaata                                                20

SEQ ID NO: 161          moltype = DNA  length = 20
FEATURE                 Location/Qualifiers
source                  1..20
                        mol_type = other DNA
                        organism = synthetic construct
SEQUENCE: 161
atatctttaa aagatagcaa                                                20

SEQ ID NO: 162          moltype = DNA  length = 20
FEATURE                 Location/Qualifiers
source                  1..20
                        mol_type = other DNA
                        organism = synthetic construct
SEQUENCE: 162
attatatctt taaaagatag                                                20

SEQ ID NO: 163          moltype = DNA  length = 20
FEATURE                 Location/Qualifiers
source                  1..20
                        mol_type = other DNA
                        organism = synthetic construct
SEQUENCE: 163
tattattata tctttaaaag                                                20

SEQ ID NO: 164          moltype = DNA  length = 20
FEATURE                 Location/Qualifiers
source                  1..20
                        mol_type = other DNA
                        organism = synthetic construct
SEQUENCE: 164
caagtttaca tcctattatt                                                20

SEQ ID NO: 165          moltype = DNA  length = 20
FEATURE                 Location/Qualifiers
```

```
source                  1..20
                        mol_type = other DNA
                        organism = synthetic construct
SEQUENCE: 165
aaaacagtag ttgtggtcaa                                                 20

SEQ ID NO: 166          moltype = DNA  length = 20
FEATURE                 Location/Qualifiers
source                  1..20
                        mol_type = other DNA
                        organism = synthetic construct
SEQUENCE: 166
aaaaaacagt agttgtggtc                                                 20

SEQ ID NO: 167          moltype = DNA  length = 20
FEATURE                 Location/Qualifiers
source                  1..20
                        mol_type = other DNA
                        organism = synthetic construct
SEQUENCE: 167
tgaatcatgt atttcaaaaa                                                 20

SEQ ID NO: 168          moltype = DNA  length = 20
FEATURE                 Location/Qualifiers
source                  1..20
                        mol_type = other DNA
                        organism = synthetic construct
SEQUENCE: 168
gccaactcag atttcacctt                                                 20

SEQ ID NO: 169          moltype = DNA  length = 20
FEATURE                 Location/Qualifiers
source                  1..20
                        mol_type = other DNA
                        organism = synthetic construct
SEQUENCE: 169
ctacacacca aagaatgcca                                                 20

SEQ ID NO: 170          moltype = DNA  length = 20
FEATURE                 Location/Qualifiers
source                  1..20
                        mol_type = other DNA
                        organism = synthetic construct
SEQUENCE: 170
agttttcagt tgattgcaga                                                 20

SEQ ID NO: 171          moltype = DNA  length = 20
FEATURE                 Location/Qualifiers
source                  1..20
                        mol_type = other DNA
                        organism = synthetic construct
SEQUENCE: 171
catcctatgt tcaagctcac                                                 20

SEQ ID NO: 172          moltype = DNA  length = 20
FEATURE                 Location/Qualifiers
source                  1..20
                        mol_type = other DNA
                        organism = synthetic construct
SEQUENCE: 172
taaacatctg cttgatcaat                                                 20

SEQ ID NO: 173          moltype = DNA  length = 20
FEATURE                 Location/Qualifiers
source                  1..20
                        mol_type = other DNA
                        organism = synthetic construct
SEQUENCE: 173
aatccacaaa gtaggatcta                                                 20

SEQ ID NO: 174          moltype = DNA  length = 20
FEATURE                 Location/Qualifiers
source                  1..20
                        mol_type = other DNA
                        organism = synthetic construct
SEQUENCE: 174
attagacatt tctacagact                                                 20

SEQ ID NO: 175          moltype = DNA  length = 20
```

-continued

```
FEATURE                 Location/Qualifiers
source                  1..20
                        mol_type = other DNA
                        organism = synthetic construct
SEQUENCE: 175
ctcaactaca tagaatatca                                        20

SEQ ID NO: 176          moltype = DNA  length = 20
FEATURE                 Location/Qualifiers
source                  1..20
                        mol_type = other DNA
                        organism = synthetic construct
SEQUENCE: 176
ttggcaacaa ttactaaaac                                        20

SEQ ID NO: 177          moltype = DNA  length = 20
FEATURE                 Location/Qualifiers
source                  1..20
                        mol_type = other DNA
                        organism = synthetic construct
SEQUENCE: 177
tcaaaaataa tgaaaattaa                                        20

SEQ ID NO: 178          moltype = DNA  length = 20
FEATURE                 Location/Qualifiers
source                  1..20
                        mol_type = other DNA
                        organism = synthetic construct
SEQUENCE: 178
caatttggct caaaaataat                                        20

SEQ ID NO: 179          moltype = DNA  length = 20
FEATURE                 Location/Qualifiers
source                  1..20
                        mol_type = other DNA
                        organism = synthetic construct
SEQUENCE: 179
ggcacaggag gtgcacattt                                        20

SEQ ID NO: 180          moltype = DNA  length = 20
FEATURE                 Location/Qualifiers
source                  1..20
                        mol_type = other DNA
                        organism = synthetic construct
SEQUENCE: 180
tagattttct aaggagaaaa                                        20

SEQ ID NO: 181          moltype = DNA  length = 20
FEATURE                 Location/Qualifiers
source                  1..20
                        mol_type = other DNA
                        organism = synthetic construct
SEQUENCE: 181
actgaccagt gaaatctgaa                                        20

SEQ ID NO: 182          moltype = DNA  length = 20
FEATURE                 Location/Qualifiers
source                  1..20
                        mol_type = other DNA
                        organism = synthetic construct
SEQUENCE: 182
ggtaagactt agcaagaaga                                        20

SEQ ID NO: 183          moltype = DNA  length = 20
FEATURE                 Location/Qualifiers
source                  1..20
                        mol_type = other DNA
                        organism = synthetic construct
SEQUENCE: 183
tctcagagtt gcaatgattg                                        20

SEQ ID NO: 184          moltype = DNA  length = 20
FEATURE                 Location/Qualifiers
source                  1..20
                        mol_type = other DNA
                        organism = synthetic construct
SEQUENCE: 184
agatcttatt agttagtata                                        20
```

```
SEQ ID NO: 185          moltype = DNA  length = 20
FEATURE                 Location/Qualifiers
source                  1..20
                        mol_type = other DNA
                        organism = synthetic construct
SEQUENCE: 185
agtactcaag gaactatttt                                            20

SEQ ID NO: 186          moltype = DNA  length = 20
FEATURE                 Location/Qualifiers
source                  1..20
                        mol_type = other DNA
                        organism = synthetic construct
SEQUENCE: 186
ggcaaacagc aacaacttca                                            20

SEQ ID NO: 187          moltype = DNA  length = 20
FEATURE                 Location/Qualifiers
source                  1..20
                        mol_type = other DNA
                        organism = synthetic construct
SEQUENCE: 187
gcacttcagt aaaatttctc                                            20

SEQ ID NO: 188          moltype = DNA  length = 20
FEATURE                 Location/Qualifiers
source                  1..20
                        mol_type = other DNA
                        organism = synthetic construct
SEQUENCE: 188
ggtccaaacg cattaagaaa                                            20

SEQ ID NO: 189          moltype = DNA  length = 20
FEATURE                 Location/Qualifiers
source                  1..20
                        mol_type = other DNA
                        organism = synthetic construct
SEQUENCE: 189
gaattatatt aatcagttat                                            20

SEQ ID NO: 190          moltype = DNA  length = 20
FEATURE                 Location/Qualifiers
source                  1..20
                        mol_type = other DNA
                        organism = synthetic construct
SEQUENCE: 190
tgtgtttgtg taactacaat                                            20

SEQ ID NO: 191          moltype = DNA  length = 20
FEATURE                 Location/Qualifiers
source                  1..20
                        mol_type = other DNA
                        organism = synthetic construct
SEQUENCE: 191
atattacttc cagaatttta                                            20

SEQ ID NO: 192          moltype = DNA  length = 20
FEATURE                 Location/Qualifiers
source                  1..20
                        mol_type = other DNA
                        organism = synthetic construct
SEQUENCE: 192
ggcagaaggg ctctattacc                                            20

SEQ ID NO: 193          moltype = DNA  length = 20
FEATURE                 Location/Qualifiers
source                  1..20
                        mol_type = other DNA
                        organism = synthetic construct
SEQUENCE: 193
cattcgaaca tgtcattttg                                            20

SEQ ID NO: 194          moltype = DNA  length = 20
FEATURE                 Location/Qualifiers
source                  1..20
                        mol_type = other DNA
                        organism = synthetic construct
SEQUENCE: 194
ctgattcatg atgggaaagc                                            20
```

```
SEQ ID NO: 195          moltype = DNA  length = 20
FEATURE                 Location/Qualifiers
source                  1..20
                        mol_type = other DNA
                        organism = synthetic construct
SEQUENCE: 195
gtggttgtct aaaacatcaa                                              20

SEQ ID NO: 196          moltype = DNA  length = 20
FEATURE                 Location/Qualifiers
source                  1..20
                        mol_type = other DNA
                        organism = synthetic construct
SEQUENCE: 196
atgactgagc tacagtacaa                                              20

SEQ ID NO: 197          moltype = DNA  length = 20
FEATURE                 Location/Qualifiers
source                  1..20
                        mol_type = other DNA
                        organism = synthetic construct
SEQUENCE: 197
gggacactac aaggtagtat                                              20

SEQ ID NO: 198          moltype = DNA  length = 20
FEATURE                 Location/Qualifiers
source                  1..20
                        mol_type = other DNA
                        organism = synthetic construct
SEQUENCE: 198
ttaaataaga atctaccatg                                              20

SEQ ID NO: 199          moltype = DNA  length = 20
FEATURE                 Location/Qualifiers
source                  1..20
                        mol_type = other DNA
                        organism = synthetic construct
SEQUENCE: 199
gctttaataa cttatttcac                                              20

SEQ ID NO: 200          moltype = DNA  length = 20
FEATURE                 Location/Qualifiers
source                  1..20
                        mol_type = other DNA
                        organism = synthetic construct
SEQUENCE: 200
aggagaaaag atatataaca                                              20

SEQ ID NO: 201          moltype = DNA  length = 20
FEATURE                 Location/Qualifiers
source                  1..20
                        mol_type = other DNA
                        organism = synthetic construct
SEQUENCE: 201
ccatttagga gaaaagatat                                              20

SEQ ID NO: 202          moltype = DNA  length = 20
FEATURE                 Location/Qualifiers
source                  1..20
                        mol_type = other DNA
                        organism = synthetic construct
SEQUENCE: 202
ttcaccctca gcgagtactg                                              20

SEQ ID NO: 203          moltype = DNA  length = 20
FEATURE                 Location/Qualifiers
source                  1..20
                        mol_type = other DNA
                        organism = synthetic construct
SEQUENCE: 203
aggctgcggt tgtttccctc                                              20

SEQ ID NO: 204          moltype = DNA  length = 20
FEATURE                 Location/Qualifiers
source                  1..20
                        mol_type = other DNA
                        organism = synthetic construct
SEQUENCE: 204
```

```
gccagatccc catcccttgt                                                20

SEQ ID NO: 205          moltype = DNA  length = 20
FEATURE                 Location/Qualifiers
source                  1..20
                        mol_type = other DNA
                        organism = synthetic construct
SEQUENCE: 205
tcacttcctt taagcaagtc                                                20

SEQ ID NO: 206          moltype = DNA  length = 20
FEATURE                 Location/Qualifiers
source                  1..20
                        mol_type = other DNA
                        organism = synthetic construct
SEQUENCE: 206
agtgatgccc aagtcacaat                                                20

SEQ ID NO: 207          moltype = DNA  length = 20
FEATURE                 Location/Qualifiers
source                  1..20
                        mol_type = other DNA
                        organism = synthetic construct
SEQUENCE: 207
agtcaagtga tgcccaagtc                                                20

SEQ ID NO: 208          moltype = DNA  length = 20
FEATURE                 Location/Qualifiers
source                  1..20
                        mol_type = other DNA
                        organism = synthetic construct
SEQUENCE: 208
ccatcagtca agtgatgccc                                                20

SEQ ID NO: 209          moltype = DNA  length = 20
FEATURE                 Location/Qualifiers
source                  1..20
                        mol_type = other DNA
                        organism = synthetic construct
SEQUENCE: 209
gattaccatc agtcaagtga                                                20

SEQ ID NO: 210          moltype = DNA  length = 20
FEATURE                 Location/Qualifiers
source                  1..20
                        mol_type = other DNA
                        organism = synthetic construct
SEQUENCE: 210
caactgatta ccatcagtca                                                20

SEQ ID NO: 211          moltype = DNA  length = 20
FEATURE                 Location/Qualifiers
source                  1..20
                        mol_type = other DNA
                        organism = synthetic construct
SEQUENCE: 211
gcagtttcca actgattcag                                                20

SEQ ID NO: 212          moltype = DNA  length = 20
FEATURE                 Location/Qualifiers
source                  1..20
                        mol_type = other DNA
                        organism = synthetic construct
SEQUENCE: 212
cgttcttgtt tcagatgtac                                                20

SEQ ID NO: 213          moltype = DNA  length = 20
FEATURE                 Location/Qualifiers
source                  1..20
                        mol_type = other DNA
                        organism = synthetic construct
SEQUENCE: 213
gccaaacaaa atattttatc                                                20

SEQ ID NO: 214          moltype = DNA  length = 20
FEATURE                 Location/Qualifiers
source                  1..20
                        mol_type = other DNA
                        organism = synthetic construct
```

-continued

```
SEQUENCE: 214
taggtaggct aacctagtcc                                            20

SEQ ID NO: 215         moltype = DNA  length = 20
FEATURE                Location/Qualifiers
source                 1..20
                       mol_type = other DNA
                       organism = synthetic construct
SEQUENCE: 215
tcccagccca aagagaagca                                            20

SEQ ID NO: 216         moltype = DNA  length = 20
FEATURE                Location/Qualifiers
source                 1..20
                       mol_type = other DNA
                       organism = synthetic construct
SEQUENCE: 216
ggatcatagc tctcggtaac                                            20

SEQ ID NO: 217         moltype = DNA  length = 20
FEATURE                Location/Qualifiers
source                 1..20
                       mol_type = other DNA
                       organism = synthetic construct
SEQUENCE: 217
aatcataaag ccctcacttc                                            20

SEQ ID NO: 218         moltype = DNA  length = 20
FEATURE                Location/Qualifiers
source                 1..20
                       mol_type = other DNA
                       organism = synthetic construct
SEQUENCE: 218
ctgattggta tttagaaagg                                            20

SEQ ID NO: 219         moltype = DNA  length = 20
FEATURE                Location/Qualifiers
source                 1..20
                       mol_type = other DNA
                       organism = synthetic construct
SEQUENCE: 219
atgcagacat gattacatta                                            20

SEQ ID NO: 220         moltype = DNA  length = 20
FEATURE                Location/Qualifiers
source                 1..20
                       mol_type = other DNA
                       organism = synthetic construct
SEQUENCE: 220
ttcatcatta aactgaaaat                                            20

SEQ ID NO: 221         moltype = DNA  length = 20
FEATURE                Location/Qualifiers
source                 1..20
                       mol_type = other DNA
                       organism = synthetic construct
SEQUENCE: 221
cttttaggtt aaaaaggtgg                                            20

SEQ ID NO: 222         moltype = DNA  length = 20
FEATURE                Location/Qualifiers
source                 1..20
                       mol_type = other DNA
                       organism = synthetic construct
SEQUENCE: 222
atacagagcc tggcaaaaca                                            20

SEQ ID NO: 223         moltype = DNA  length = 20
FEATURE                Location/Qualifiers
source                 1..20
                       mol_type = other DNA
                       organism = synthetic construct
SEQUENCE: 223
ttctatttac agagcattag                                            20

SEQ ID NO: 224         moltype = DNA  length = 20
FEATURE                Location/Qualifiers
source                 1..20
                       mol_type = other DNA
```

```
                      organism = synthetic construct
SEQUENCE: 224
gccttcacat taattcacca                                        20

SEQ ID NO: 225        moltype = DNA  length = 20
FEATURE               Location/Qualifiers
source                1..20
                      mol_type = other DNA
                      organism = synthetic construct
SEQUENCE: 225
tgtgttattg cccctaaaaa                                        20

SEQ ID NO: 226        moltype = DNA  length = 20
FEATURE               Location/Qualifiers
source                1..20
                      mol_type = other DNA
                      organism = synthetic construct
SEQUENCE: 226
tgtattcact atactatgcc                                        20

SEQ ID NO: 227        moltype = DNA  length = 20
FEATURE               Location/Qualifiers
source                1..20
                      mol_type = other DNA
                      organism = synthetic construct
SEQUENCE: 227
aagttattta aagtatagca                                        20

SEQ ID NO: 228        moltype = DNA  length = 20
FEATURE               Location/Qualifiers
source                1..20
                      mol_type = other DNA
                      organism = synthetic construct
SEQUENCE: 228
gacattgaag tatcaagaca                                        20

SEQ ID NO: 229        moltype = DNA  length = 20
FEATURE               Location/Qualifiers
source                1..20
                      mol_type = other DNA
                      organism = synthetic construct
SEQUENCE: 229
tgttaagtaa tcttagaaaa                                        20

SEQ ID NO: 230        moltype = DNA  length = 20
FEATURE               Location/Qualifiers
source                1..20
                      mol_type = other DNA
                      organism = synthetic construct
SEQUENCE: 230
ggcatacatt tagaaattca                                        20

SEQ ID NO: 231        moltype = DNA  length = 20
FEATURE               Location/Qualifiers
source                1..20
                      mol_type = other DNA
                      organism = synthetic construct
SEQUENCE: 231
accttatgca tccatattct                                        20

SEQ ID NO: 232        moltype = DNA  length = 20
FEATURE               Location/Qualifiers
source                1..20
                      mol_type = other DNA
                      organism = synthetic construct
SEQUENCE: 232
gaattctctt gggaaccatt                                        20

SEQ ID NO: 233        moltype = DNA  length = 20
FEATURE               Location/Qualifiers
source                1..20
                      mol_type = other DNA
                      organism = synthetic construct
SEQUENCE: 233
atattcaact acaggattta                                        20

SEQ ID NO: 234        moltype = DNA  length = 20
FEATURE               Location/Qualifiers
source                1..20
```

```
                        mol_type = other DNA
                        organism = synthetic construct
SEQUENCE: 234
atgtgttctt tagatacatc                                                20

SEQ ID NO: 235          moltype = DNA  length = 20
FEATURE                 Location/Qualifiers
source                  1..20
                        mol_type = other DNA
                        organism = synthetic construct
SEQUENCE: 235
ccttatacag atacatgctg                                                20

SEQ ID NO: 236          moltype = DNA  length = 20
FEATURE                 Location/Qualifiers
source                  1..20
                        mol_type = other DNA
                        organism = synthetic construct
SEQUENCE: 236
tagatgcaat tactattttc                                                20

SEQ ID NO: 237          moltype = DNA  length = 20
FEATURE                 Location/Qualifiers
source                  1..20
                        mol_type = other DNA
                        organism = synthetic construct
SEQUENCE: 237
tgtacttccc aaacttgaac                                                20

SEQ ID NO: 238          moltype = DNA  length = 20
FEATURE                 Location/Qualifiers
source                  1..20
                        mol_type = other DNA
                        organism = synthetic construct
SEQUENCE: 238
ctgaagctca acaacaccaa                                                20

SEQ ID NO: 239          moltype = DNA  length = 20
FEATURE                 Location/Qualifiers
source                  1..20
                        mol_type = other DNA
                        organism = synthetic construct
SEQUENCE: 239
gtctatagaa tcaaactgaa                                                20

SEQ ID NO: 240          moltype = DNA  length = 20
FEATURE                 Location/Qualifiers
source                  1..20
                        mol_type = other DNA
                        organism = synthetic construct
SEQUENCE: 240
ttgaatcaat acctaacctc                                                20

SEQ ID NO: 241          moltype = DNA  length = 20
FEATURE                 Location/Qualifiers
source                  1..20
                        mol_type = other DNA
                        organism = synthetic construct
SEQUENCE: 241
tgcctctttt agaaaagatc                                                20

SEQ ID NO: 242          moltype = DNA  length = 20
FEATURE                 Location/Qualifiers
source                  1..20
                        mol_type = other DNA
                        organism = synthetic construct
SEQUENCE: 242
atggaatcat tggtttatcg                                                20

SEQ ID NO: 243          moltype = DNA  length = 20
FEATURE                 Location/Qualifiers
source                  1..20
                        mol_type = other DNA
                        organism = synthetic construct
SEQUENCE: 243
aaagctcact tttattcttt                                                20

SEQ ID NO: 244          moltype = DNA  length = 20
FEATURE                 Location/Qualifiers
```

-continued

```
source                  1..20
                        mol_type = other DNA
                        organism = synthetic construct
SEQUENCE: 244
ggtgccgcca ccatgcccgg                                                        20

SEQ ID NO: 245          moltype = DNA  length = 20
FEATURE                 Location/Qualifiers
source                  1..20
                        mol_type = other DNA
                        organism = synthetic construct
SEQUENCE: 245
gagagaagct gggcaataaa                                                        20

SEQ ID NO: 246          moltype = DNA  length = 20
FEATURE                 Location/Qualifiers
source                  1..20
                        mol_type = other DNA
                        organism = synthetic construct
SEQUENCE: 246
tctgaccctg cacaataaag                                                        20

SEQ ID NO: 247          moltype = DNA  length = 20
FEATURE                 Location/Qualifiers
source                  1..20
                        mol_type = other DNA
                        organism = synthetic construct
SEQUENCE: 247
atagtgtgtg attcaaaacg                                                        20

SEQ ID NO: 248          moltype = DNA  length = 20
FEATURE                 Location/Qualifiers
source                  1..20
                        mol_type = other DNA
                        organism = synthetic construct
SEQUENCE: 248
actgtatcag ctatctaaaa                                                        20

SEQ ID NO: 249          moltype = DNA  length = 20
FEATURE                 Location/Qualifiers
source                  1..20
                        mol_type = other DNA
                        organism = synthetic construct
SEQUENCE: 249
ttatttgtat aggaacctac                                                        20

SEQ ID NO: 250          moltype = DNA  length = 20
FEATURE                 Location/Qualifiers
source                  1..20
                        mol_type = other DNA
                        organism = synthetic construct
SEQUENCE: 250
tgtgagctga tggcactgta                                                        20

SEQ ID NO: 251          moltype = DNA  length = 20
FEATURE                 Location/Qualifiers
source                  1..20
                        mol_type = other DNA
                        organism = synthetic construct
SEQUENCE: 251
ccttatttac tttctctgca                                                        20

SEQ ID NO: 252          moltype = DNA  length = 20
FEATURE                 Location/Qualifiers
source                  1..20
                        mol_type = other DNA
                        organism = synthetic construct
SEQUENCE: 252
ggaataaggt cactagttcg                                                        20

SEQ ID NO: 253          moltype = DNA  length = 20
FEATURE                 Location/Qualifiers
source                  1..20
                        mol_type = other DNA
                        organism = synthetic construct
SEQUENCE: 253
atttgcaaca atttttaaat                                                        20

SEQ ID NO: 254          moltype = DNA  length = 20
```

```
FEATURE                 Location/Qualifiers
source                  1..20
                        mol_type = other DNA
                        organism = synthetic construct
SEQUENCE: 254
ataaactacc aatgatatcc                                              20

SEQ ID NO: 255          moltype = DNA  length = 20
FEATURE                 Location/Qualifiers
source                  1..20
                        mol_type = other DNA
                        organism = synthetic construct
SEQUENCE: 255
tacctgatcc aggaaggctt                                              20

SEQ ID NO: 256          moltype = DNA  length = 20
FEATURE                 Location/Qualifiers
source                  1..20
                        mol_type = other DNA
                        organism = synthetic construct
SEQUENCE: 256
ttcccgaagc ataaatctag                                              20

SEQ ID NO: 257          moltype = DNA  length = 20
FEATURE                 Location/Qualifiers
source                  1..20
                        mol_type = other DNA
                        organism = synthetic construct
SEQUENCE: 257
ttgagaagca tgaaattcca                                              20

SEQ ID NO: 258          moltype = DNA  length = 20
FEATURE                 Location/Qualifiers
source                  1..20
                        mol_type = other DNA
                        organism = synthetic construct
SEQUENCE: 258
gcgggacacc gtaggttacg                                              20

SEQ ID NO: 259          moltype = DNA  length = 20
FEATURE                 Location/Qualifiers
source                  1..20
                        mol_type = other DNA
                        organism = synthetic construct
SEQUENCE: 259
ctttcctagc gggacaccgt                                              20

SEQ ID NO: 260          moltype = DNA  length = 20
FEATURE                 Location/Qualifiers
source                  1..20
                        mol_type = other DNA
                        organism = synthetic construct
SEQUENCE: 260
gcacctctct ttcctagcgg                                              20

SEQ ID NO: 261          moltype = DNA  length = 20
FEATURE                 Location/Qualifiers
source                  1..20
                        mol_type = other DNA
                        organism = synthetic construct
SEQUENCE: 261
tgtttgacgc acctctcttt                                              20

SEQ ID NO: 262          moltype = DNA  length = 20
FEATURE                 Location/Qualifiers
source                  1..20
                        mol_type = other DNA
                        organism = synthetic construct
SEQUENCE: 262
cttgtcgctg tttgacgcac                                              20

SEQ ID NO: 263          moltype = DNA  length = 20
FEATURE                 Location/Qualifiers
source                  1..20
                        mol_type = other DNA
                        organism = synthetic construct
SEQUENCE: 263
gggcggaact tgtcgctgtt                                              20
```

```
SEQ ID NO: 264          moltype = DNA  length = 20
FEATURE                 Location/Qualifiers
source                  1..20
                        mol_type = other DNA
                        organism = synthetic construct
SEQUENCE: 264
gcagcaggga cggctgacac                                              20

SEQ ID NO: 265          moltype = DNA  length = 20
FEATURE                 Location/Qualifiers
source                  1..20
                        mol_type = other DNA
                        organism = synthetic construct
SEQUENCE: 265
agaagcaacc gggcagcagg                                              20

SEQ ID NO: 266          moltype = DNA  length = 20
FEATURE                 Location/Qualifiers
source                  1..20
                        mol_type = other DNA
                        organism = synthetic construct
SEQUENCE: 266
cccaaaagag aagcaaccgg                                              20

SEQ ID NO: 267          moltype = DNA  length = 20
FEATURE                 Location/Qualifiers
source                  1..20
                        mol_type = other DNA
                        organism = synthetic construct
SEQUENCE: 267
accccgcccc caaaagagaa                                              20

SEQ ID NO: 268          moltype = DNA  length = 20
FEATURE                 Location/Qualifiers
source                  1..20
                        mol_type = other DNA
                        organism = synthetic construct
SEQUENCE: 268
cttgctagac cccgccccca                                              20

SEQ ID NO: 269          moltype = DNA  length = 20
FEATURE                 Location/Qualifiers
source                  1..20
                        mol_type = other DNA
                        organism = synthetic construct
SEQUENCE: 269
cacctgctct tgctagaccc                                              20

SEQ ID NO: 270          moltype = DNA  length = 20
FEATURE                 Location/Qualifiers
source                  1..20
                        mol_type = other DNA
                        organism = synthetic construct
SEQUENCE: 270
taaacccaca cctgctcttg                                              20

SEQ ID NO: 271          moltype = DNA  length = 20
FEATURE                 Location/Qualifiers
source                  1..20
                        mol_type = other DNA
                        organism = synthetic construct
SEQUENCE: 271
ctcctaaacc cacacctgct                                              20

SEQ ID NO: 272          moltype = DNA  length = 20
FEATURE                 Location/Qualifiers
source                  1..20
                        mol_type = other DNA
                        organism = synthetic construct
SEQUENCE: 272
acacacacct cctaaaccca                                              20

SEQ ID NO: 273          moltype = DNA  length = 20
FEATURE                 Location/Qualifiers
source                  1..20
                        mol_type = other DNA
                        organism = synthetic construct
SEQUENCE: 273
aaacaaaaac acacacctcc                                              20
```

```
SEQ ID NO: 274          moltype = DNA  length = 20
FEATURE                 Location/Qualifiers
source                  1..20
                        mol_type = other DNA
                        organism = synthetic construct
SEQUENCE: 274
ggtgggaaaa acaaaaacac                                              20

SEQ ID NO: 275          moltype = DNA  length = 20
FEATURE                 Location/Qualifiers
source                  1..20
                        mol_type = other DNA
                        organism = synthetic construct
SEQUENCE: 275
ctgtgagagc aagtagtggg                                              20

SEQ ID NO: 276          moltype = DNA  length = 20
FEATURE                 Location/Qualifiers
source                  1..20
                        mol_type = other DNA
                        organism = synthetic construct
SEQUENCE: 276
agcgagtact gtgagagcaa                                              20

SEQ ID NO: 277          moltype = DNA  length = 20
FEATURE                 Location/Qualifiers
source                  1..20
                        mol_type = other DNA
                        organism = synthetic construct
SEQUENCE: 277
tcaccctcag cgagtactgt                                              20

SEQ ID NO: 278          moltype = DNA  length = 20
FEATURE                 Location/Qualifiers
source                  1..20
                        mol_type = other DNA
                        organism = synthetic construct
SEQUENCE: 278
tcaggtcttt tcttgttcac                                              20

SEQ ID NO: 279          moltype = DNA  length = 20
FEATURE                 Location/Qualifiers
source                  1..20
                        mol_type = other DNA
                        organism = synthetic construct
SEQUENCE: 279
aatctttatc aggtcttttc                                              20

SEQ ID NO: 280          moltype = DNA  length = 20
FEATURE                 Location/Qualifiers
source                  1..20
                        mol_type = other DNA
                        organism = synthetic construct
SEQUENCE: 280
ttctggttaa tctttatcag                                              20

SEQ ID NO: 281          moltype = DNA  length = 20
FEATURE                 Location/Qualifiers
source                  1..20
                        mol_type = other DNA
                        organism = synthetic construct
SEQUENCE: 281
ttgttttctt ctggttaatc                                              20

SEQ ID NO: 282          moltype = DNA  length = 20
FEATURE                 Location/Qualifiers
source                  1..20
                        mol_type = other DNA
                        organism = synthetic construct
SEQUENCE: 282
ttccctcctt gttttcttct                                              20

SEQ ID NO: 283          moltype = DNA  length = 20
FEATURE                 Location/Qualifiers
source                  1..20
                        mol_type = other DNA
                        organism = synthetic construct
SEQUENCE: 283
```

```
gcggttgttt ccctccttgt                                              20

SEQ ID NO: 284         moltype = DNA  length = 20
FEATURE                Location/Qualifiers
source                 1..20
                       mol_type = other DNA
                       organism = synthetic construct
SEQUENCE: 284
tacaggctgc ggttgtttcc                                              20

SEQ ID NO: 285         moltype = DNA  length = 20
FEATURE                Location/Qualifiers
source                 1..20
                       mol_type = other DNA
                       organism = synthetic construct
SEQUENCE: 285
gagcttgcta caggctgcgg                                              20

SEQ ID NO: 286         moltype = DNA  length = 20
FEATURE                Location/Qualifiers
source                 1..20
                       mol_type = other DNA
                       organism = synthetic construct
SEQUENCE: 286
gagttccaga gcttgctaca                                              20

SEQ ID NO: 287         moltype = DNA  length = 20
FEATURE                Location/Qualifiers
source                 1..20
                       mol_type = other DNA
                       organism = synthetic construct
SEQUENCE: 287
cgactcctga gttccagagc                                              20

SEQ ID NO: 288         moltype = DNA  length = 20
FEATURE                Location/Qualifiers
source                 1..20
                       mol_type = other DNA
                       organism = synthetic construct
SEQUENCE: 288
cccggcccct agcgcgcgac                                              20

SEQ ID NO: 289         moltype = DNA  length = 20
FEATURE                Location/Qualifiers
source                 1..20
                       mol_type = other DNA
                       organism = synthetic construct
SEQUENCE: 289
gccccggccc cggcccctag                                              20

SEQ ID NO: 290         moltype = DNA  length = 20
FEATURE                Location/Qualifiers
source                 1..20
                       mol_type = other DNA
                       organism = synthetic construct
SEQUENCE: 290
accacgcccc ggccccggcc                                              20

SEQ ID NO: 291         moltype = DNA  length = 20
FEATURE                Location/Qualifiers
source                 1..20
                       mol_type = other DNA
                       organism = synthetic construct
SEQUENCE: 291
ccgccccgac cacgccccgg                                              20

SEQ ID NO: 292         moltype = DNA  length = 20
FEATURE                Location/Qualifiers
source                 1..20
                       mol_type = other DNA
                       organism = synthetic construct
SEQUENCE: 292
ccccgggccc gccccgacca                                              20

SEQ ID NO: 293         moltype = DNA  length = 20
FEATURE                Location/Qualifiers
source                 1..20
                       mol_type = other DNA
                       organism = synthetic construct
```

```
SEQUENCE: 293
cgccccgggc ccgcccccgg                                              20

SEQ ID NO: 294          moltype = DNA  length = 20
FEATURE                 Location/Qualifiers
source                  1..20
                        mol_type = other DNA
                        organism = synthetic construct
SEQUENCE: 294
cgcagccccg ccccgggccc                                              20

SEQ ID NO: 295          moltype = DNA  length = 20
FEATURE                 Location/Qualifiers
source                  1..20
                        mol_type = other DNA
                        organism = synthetic construct
SEQUENCE: 295
accgcaaccg cagccccgcc                                              20

SEQ ID NO: 296          moltype = DNA  length = 20
FEATURE                 Location/Qualifiers
source                  1..20
                        mol_type = other DNA
                        organism = synthetic construct
SEQUENCE: 296
gcgcaggcac cgcaaccgca                                              20

SEQ ID NO: 297          moltype = DNA  length = 20
FEATURE                 Location/Qualifiers
source                  1..20
                        mol_type = other DNA
                        organism = synthetic construct
SEQUENCE: 297
ggcgcaggca ccgcaaccgc                                              20

SEQ ID NO: 298          moltype = DNA  length = 20
FEATURE                 Location/Qualifiers
source                  1..20
                        mol_type = other DNA
                        organism = synthetic construct
SEQUENCE: 298
cgcctccgcc gccgcgggcg                                              20

SEQ ID NO: 299          moltype = DNA  length = 20
FEATURE                 Location/Qualifiers
source                  1..20
                        mol_type = other DNA
                        organism = synthetic construct
SEQUENCE: 299
accgcctgcg cctccgccgc                                              20

SEQ ID NO: 300          moltype = DNA  length = 20
FEATURE                 Location/Qualifiers
source                  1..20
                        mol_type = other DNA
                        organism = synthetic construct
SEQUENCE: 300
cactcgccac cgcctgcgcc                                              20

SEQ ID NO: 301          moltype = DNA  length = 20
FEATURE                 Location/Qualifiers
source                  1..20
                        mol_type = other DNA
                        organism = synthetic construct
SEQUENCE: 301
ccactcgcca ccgcctgcgc                                              20

SEQ ID NO: 302          moltype = DNA  length = 20
FEATURE                 Location/Qualifiers
source                  1..20
                        mol_type = other DNA
                        organism = synthetic construct
SEQUENCE: 302
ggtccccggg aaggagacag                                              20

SEQ ID NO: 303          moltype = DNA  length = 20
FEATURE                 Location/Qualifiers
source                  1..20
                        mol_type = other DNA
```

```
                       organism = synthetic construct
SEQUENCE: 303
aacaactggt gcatggcaac                                              20

SEQ ID NO: 304         moltype = DNA  length = 20
FEATURE                Location/Qualifiers
source                 1..20
                       mol_type = other DNA
                       organism = synthetic construct
SEQUENCE: 304
gtttcagatg tactatcagc                                              20

SEQ ID NO: 305         moltype = DNA  length = 20
FEATURE                Location/Qualifiers
source                 1..20
                       mol_type = other DNA
                       organism = synthetic construct
SEQUENCE: 305
aaggtgaagt tcatatcact                                              20

SEQ ID NO: 306         moltype = DNA  length = 20
FEATURE                Location/Qualifiers
source                 1..20
                       mol_type = other DNA
                       organism = synthetic construct
SEQUENCE: 306
ggtaacttca aactcttggg                                              20

SEQ ID NO: 307         moltype = DNA  length = 20
FEATURE                Location/Qualifiers
source                 1..20
                       mol_type = other DNA
                       organism = synthetic construct
SEQUENCE: 307
ggttcatgag aggtttccca                                              20

SEQ ID NO: 308         moltype = DNA  length = 20
FEATURE                Location/Qualifiers
source                 1..20
                       mol_type = other DNA
                       organism = synthetic construct
SEQUENCE: 308
tactgaattg cttagtttta                                              20

SEQ ID NO: 309         moltype = DNA  length = 20
FEATURE                Location/Qualifiers
source                 1..20
                       mol_type = other DNA
                       organism = synthetic construct
SEQUENCE: 309
ctaacagaat aagaaaaaaa                                              20

SEQ ID NO: 310         moltype = DNA  length = 20
FEATURE                Location/Qualifiers
source                 1..20
                       mol_type = other DNA
                       organism = synthetic construct
SEQUENCE: 310
gagcattaga tgagtgcttt                                              20

SEQ ID NO: 311         moltype = DNA  length = 20
FEATURE                Location/Qualifiers
source                 1..20
                       mol_type = other DNA
                       organism = synthetic construct
SEQUENCE: 311
tgcattccta agcaatgtgt                                              20

SEQ ID NO: 312         moltype = DNA  length = 20
FEATURE                Location/Qualifiers
source                 1..20
                       mol_type = other DNA
                       organism = synthetic construct
SEQUENCE: 312
tctaggcctt cacattaatt                                              20

SEQ ID NO: 313         moltype = DNA  length = 20
FEATURE                Location/Qualifiers
source                 1..20
```

```
                        mol_type = other DNA
                        organism = synthetic construct
SEQUENCE: 313
cctgtctatg cctaggtgaa                                              20

SEQ ID NO: 314          moltype = DNA  length = 20
FEATURE                 Location/Qualifiers
source                  1..20
                        mol_type = other DNA
                        organism = synthetic construct
SEQUENCE: 314
tagcacatac aattattaca                                              20

SEQ ID NO: 315          moltype = DNA  length = 20
FEATURE                 Location/Qualifiers
source                  1..20
                        mol_type = other DNA
                        organism = synthetic construct
SEQUENCE: 315
gaggagaaga acataaacgc                                              20

SEQ ID NO: 316          moltype = DNA  length = 20
FEATURE                 Location/Qualifiers
source                  1..20
                        mol_type = other DNA
                        organism = synthetic construct
SEQUENCE: 316
taccacaagt ctggagccat                                              20

SEQ ID NO: 317          moltype = DNA  length = 20
FEATURE                 Location/Qualifiers
source                  1..20
                        mol_type = other DNA
                        organism = synthetic construct
SEQUENCE: 317
gatactggat tgttgaaact                                              20

SEQ ID NO: 318          moltype = DNA  length = 20
FEATURE                 Location/Qualifiers
source                  1..20
                        mol_type = other DNA
                        organism = synthetic construct
SEQUENCE: 318
tagtatgact ggagatttgg                                              20

SEQ ID NO: 319          moltype = DNA  length = 20
FEATURE                 Location/Qualifiers
source                  1..20
                        mol_type = other DNA
                        organism = synthetic construct
SEQUENCE: 319
atcaaaaccc caaatgattt                                              20

SEQ ID NO: 320          moltype = DNA  length = 20
FEATURE                 Location/Qualifiers
source                  1..20
                        mol_type = other DNA
                        organism = synthetic construct
SEQUENCE: 320
atccaaatgc tccggagata                                              20

SEQ ID NO: 321          moltype = DNA  length = 20
FEATURE                 Location/Qualifiers
source                  1..20
                        mol_type = other DNA
                        organism = synthetic construct
SEQUENCE: 321
tcgacatcac tgcattccaa                                              20

SEQ ID NO: 322          moltype = DNA  length = 20
FEATURE                 Location/Qualifiers
source                  1..20
                        mol_type = other DNA
                        organism = synthetic construct
SEQUENCE: 322
caacagctgg agatggcggt                                              20

SEQ ID NO: 323          moltype = DNA  length = 20
FEATURE                 Location/Qualifiers
```

```
source                1..20
                      mol_type = other DNA
                      organism = synthetic construct
SEQUENCE: 323
atttgccact taaagcaatc                                       20

SEQ ID NO: 324        moltype = DNA  length = 20
FEATURE               Location/Qualifiers
source                1..20
                      mol_type = other DNA
                      organism = synthetic construct
SEQUENCE: 324
gtacctgttc tgtctttgga                                       20

SEQ ID NO: 325        moltype = DNA  length = 20
FEATURE               Location/Qualifiers
source                1..20
                      mol_type = other DNA
                      organism = synthetic construct
SEQUENCE: 325
caagaaaagt tatttctcca                                       20

SEQ ID NO: 326        moltype = DNA  length = 20
FEATURE               Location/Qualifiers
source                1..20
                      mol_type = other DNA
                      organism = synthetic construct
SEQUENCE: 326
gaaggatttc tccatttaga                                       20

SEQ ID NO: 327        moltype = DNA  length = 20
FEATURE               Location/Qualifiers
source                1..20
                      mol_type = other DNA
                      organism = synthetic construct
SEQUENCE: 327
ttacatctat agcaccactc                                       20

SEQ ID NO: 328        moltype = DNA  length = 20
FEATURE               Location/Qualifiers
source                1..20
                      mol_type = other DNA
                      organism = synthetic construct
SEQUENCE: 328
tcactccctt ttcagacaag                                       20

SEQ ID NO: 329        moltype = DNA  length = 20
FEATURE               Location/Qualifiers
source                1..20
                      mol_type = other DNA
                      organism = synthetic construct
SEQUENCE: 329
agtttccatc aaagattaat                                       20

SEQ ID NO: 330        moltype = DNA  length = 20
FEATURE               Location/Qualifiers
source                1..20
                      mol_type = other DNA
                      organism = synthetic construct
SEQUENCE: 330
atagtccata tgtgctgcga                                       20

SEQ ID NO: 331        moltype = DNA  length = 20
FEATURE               Location/Qualifiers
source                1..20
                      mol_type = other DNA
                      organism = synthetic construct
SEQUENCE: 331
aactaagttc tgtctgtgga                                       20

SEQ ID NO: 332        moltype = DNA  length = 20
FEATURE               Location/Qualifiers
source                1..20
                      mol_type = other DNA
                      organism = synthetic construct
SEQUENCE: 332
caacacacac tctatgaagt                                       20

SEQ ID NO: 333        moltype = DNA  length = 20
```

-continued

```
FEATURE                Location/Qualifiers
source                 1..20
                       mol_type = other DNA
                       organism = synthetic construct
SEQUENCE: 333
ttcctttccg gattatatgt                                              20

SEQ ID NO: 334         moltype = DNA  length = 20
FEATURE                Location/Qualifiers
source                 1..20
                       mol_type = other DNA
                       organism = synthetic construct
SEQUENCE: 334
tttccattac aggaatcact                                              20

SEQ ID NO: 335         moltype = DNA  length = 20
FEATURE                Location/Qualifiers
source                 1..20
                       mol_type = other DNA
                       organism = synthetic construct
SEQUENCE: 335
atcagcctat atctatttcc                                              20

SEQ ID NO: 336         moltype = DNA  length = 20
FEATURE                Location/Qualifiers
source                 1..20
                       mol_type = other DNA
                       organism = synthetic construct
SEQUENCE: 336
tcaatgacca ggcggtcccc                                              20

SEQ ID NO: 337         moltype = DNA  length = 20
FEATURE                Location/Qualifiers
source                 1..20
                       mol_type = other DNA
                       organism = synthetic construct
SEQUENCE: 337
ctttttatgg aaaaggaaaa                                              20

SEQ ID NO: 338         moltype = DNA  length = 20
FEATURE                Location/Qualifiers
source                 1..20
                       mol_type = other DNA
                       organism = synthetic construct
SEQUENCE: 338
tgtttcccca aaaatttctg                                              20

SEQ ID NO: 339         moltype = DNA  length = 20
FEATURE                Location/Qualifiers
source                 1..20
                       mol_type = other DNA
                       organism = synthetic construct
SEQUENCE: 339
agatatccac tcgccaccgc                                              20

SEQ ID NO: 340         moltype = DNA  length = 20
FEATURE                Location/Qualifiers
source                 1..20
                       mol_type = other DNA
                       organism = synthetic construct
SEQUENCE: 340
ccggccccgg ccccggcccc                                              20

SEQ ID NO: 341         moltype = DNA  length = 20
FEATURE                Location/Qualifiers
source                 1..20
                       mol_type = other DNA
                       organism = synthetic construct
SEQUENCE: 341
cccggccccg gccccggccc                                              20

SEQ ID NO: 342         moltype = DNA  length = 20
FEATURE                Location/Qualifiers
source                 1..20
                       mol_type = other DNA
                       organism = synthetic construct
SEQUENCE: 342
ccccggcccc ggccccggcc                                              20
```

```
SEQ ID NO: 343          moltype = DNA  length = 20
FEATURE                 Location/Qualifiers
source                  1..20
                        mol_type = other DNA
                        organism = synthetic construct
SEQUENCE: 343
gccccggccc cggccccggc                                              20

SEQ ID NO: 344          moltype = DNA  length = 20
FEATURE                 Location/Qualifiers
source                  1..20
                        mol_type = other DNA
                        organism = synthetic construct
SEQUENCE: 344
ggccccggcc ccggccccgg                                              20

SEQ ID NO: 345          moltype = DNA  length = 20
FEATURE                 Location/Qualifiers
source                  1..20
                        mol_type = other DNA
                        organism = synthetic construct
SEQUENCE: 345
cggccccggc cccggccccg                                              20

SEQ ID NO: 346          moltype = DNA  length = 19
FEATURE                 Location/Qualifiers
source                  1..19
                        mol_type = other DNA
                        organism = synthetic construct
SEQUENCE: 346
cggccccggc cccggcccc                                               19

SEQ ID NO: 347          moltype = DNA  length = 19
FEATURE                 Location/Qualifiers
source                  1..19
                        mol_type = other DNA
                        organism = synthetic construct
SEQUENCE: 347
ccggccccgg ccccggccc                                               19

SEQ ID NO: 348          moltype = DNA  length = 19
FEATURE                 Location/Qualifiers
source                  1..19
                        mol_type = other DNA
                        organism = synthetic construct
SEQUENCE: 348
cccggccccg gccccggcc                                               19

SEQ ID NO: 349          moltype = DNA  length = 19
FEATURE                 Location/Qualifiers
source                  1..19
                        mol_type = other DNA
                        organism = synthetic construct
SEQUENCE: 349
ccccggcccc ggccccggc                                               19

SEQ ID NO: 350          moltype = DNA  length = 19
FEATURE                 Location/Qualifiers
source                  1..19
                        mol_type = other DNA
                        organism = synthetic construct
SEQUENCE: 350
gccccggccc cggccccgg                                               19

SEQ ID NO: 351          moltype = DNA  length = 19
FEATURE                 Location/Qualifiers
source                  1..19
                        mol_type = other DNA
                        organism = synthetic construct
SEQUENCE: 351
ggccccggcc ccggccccg                                               19

SEQ ID NO: 352          moltype = DNA  length = 18
FEATURE                 Location/Qualifiers
source                  1..18
                        mol_type = other DNA
                        organism = synthetic construct
SEQUENCE: 352
ggccccggcc ccggcccc                                                18
```

```
SEQ ID NO: 353          moltype = DNA  length = 18
FEATURE                 Location/Qualifiers
source                  1..18
                        mol_type = other DNA
                        organism = synthetic construct
SEQUENCE: 353
cggccccggc cccggccc                                                18

SEQ ID NO: 354          moltype = DNA  length = 18
FEATURE                 Location/Qualifiers
source                  1..18
                        mol_type = other DNA
                        organism = synthetic construct
SEQUENCE: 354
ccggccccgg ccccggcc                                                18

SEQ ID NO: 355          moltype = DNA  length = 18
FEATURE                 Location/Qualifiers
source                  1..18
                        mol_type = other DNA
                        organism = synthetic construct
SEQUENCE: 355
cccggccccg gccccggc                                                18

SEQ ID NO: 356          moltype = DNA  length = 18
FEATURE                 Location/Qualifiers
source                  1..18
                        mol_type = other DNA
                        organism = synthetic construct
SEQUENCE: 356
ccccggcccc ggccccgg                                                18

SEQ ID NO: 357          moltype = DNA  length = 18
FEATURE                 Location/Qualifiers
source                  1..18
                        mol_type = other DNA
                        organism = synthetic construct
SEQUENCE: 357
gccccggccc cggccccg                                                18

SEQ ID NO: 358          moltype = DNA  length = 17
FEATURE                 Location/Qualifiers
source                  1..17
                        mol_type = other DNA
                        organism = synthetic construct
SEQUENCE: 358
gccccggccc cggcccc                                                 17

SEQ ID NO: 359          moltype = DNA  length = 17
FEATURE                 Location/Qualifiers
source                  1..17
                        mol_type = other DNA
                        organism = synthetic construct
SEQUENCE: 359
ggccccggcc ccggccc                                                 17

SEQ ID NO: 360          moltype = DNA  length = 17
FEATURE                 Location/Qualifiers
source                  1..17
                        mol_type = other DNA
                        organism = synthetic construct
SEQUENCE: 360
cggccccggc cccggcc                                                 17

SEQ ID NO: 361          moltype = DNA  length = 17
FEATURE                 Location/Qualifiers
source                  1..17
                        mol_type = other DNA
                        organism = synthetic construct
SEQUENCE: 361
ccggccccgg ccccggc                                                 17

SEQ ID NO: 362          moltype = DNA  length = 17
FEATURE                 Location/Qualifiers
source                  1..17
                        mol_type = other DNA
                        organism = synthetic construct
SEQUENCE: 362
```

```
cccggccccg gccccgg                                                17

SEQ ID NO: 363          moltype = DNA  length = 17
FEATURE                 Location/Qualifiers
source                  1..17
                        mol_type = other DNA
                        organism = synthetic construct
SEQUENCE: 363
ccccggcccc ggccccg                                                17

SEQ ID NO: 364          moltype = DNA  length = 16
FEATURE                 Location/Qualifiers
source                  1..16
                        mol_type = other DNA
                        organism = synthetic construct
SEQUENCE: 364
ccccggcccc ggcccc                                                 16

SEQ ID NO: 365          moltype = DNA  length = 16
FEATURE                 Location/Qualifiers
source                  1..16
                        mol_type = other DNA
                        organism = synthetic construct
SEQUENCE: 365
gccccggccc cggccc                                                 16

SEQ ID NO: 366          moltype = DNA  length = 16
FEATURE                 Location/Qualifiers
source                  1..16
                        mol_type = other DNA
                        organism = synthetic construct
SEQUENCE: 366
ggccccggcc ccggcc                                                 16

SEQ ID NO: 367          moltype = DNA  length = 16
FEATURE                 Location/Qualifiers
source                  1..16
                        mol_type = other DNA
                        organism = synthetic construct
SEQUENCE: 367
cggccccggc cccggc                                                 16

SEQ ID NO: 368          moltype = DNA  length = 16
FEATURE                 Location/Qualifiers
source                  1..16
                        mol_type = other DNA
                        organism = synthetic construct
SEQUENCE: 368
ccggccccgg ccccgg                                                 16

SEQ ID NO: 369          moltype = DNA  length = 16
FEATURE                 Location/Qualifiers
source                  1..16
                        mol_type = other DNA
                        organism = synthetic construct
SEQUENCE: 369
cccggccccg gccccg                                                 16

SEQ ID NO: 370          moltype = DNA  length = 20
FEATURE                 Location/Qualifiers
source                  1..20
                        mol_type = other DNA
                        organism = synthetic construct
modified_base           1
                        mod_base = OTHER
                        note = 2'-MOE guanosine 3'-phosphorothioate
modified_base           2
                        mod_base = OTHER
                        note = 2'-MOE adenosine 3'-phosphodiester
modified_base           3..4
                        mod_base = OTHER
                        note = 2'-MOE 5-methylcytidine 3'-phosphodiester
modified_base           5
                        mod_base = OTHER
                        note = 2'-MOE guanosine 3'-phosphorothioate
modified_base           6
                        mod_base = OTHER
                        note = 5-methyl-2'-deoxycytidine 3'-phosphorothioate
modified_base           7..8
```

-continued

```
                        mod_base = OTHER
                        note = 2'-deoxythymidine 3'-phosphorothioate
modified_base           9
                        mod_base = OTHER
                        note = 2'-deoxyguanosine 3'-phosphorothioate
modified_base           10
                        mod_base = OTHER
                        note = 2'-deoxyadenosine 3'-phosphorothioate
modified_base           11
                        mod_base = OTHER
                        note = 2'-deoxyguanosine 3'-phosphorothioate
modified_base           12..14
                        mod_base = OTHER
                        note = 2'-deoxythymidine 3'-phosphorothioate
modified_base           15
                        mod_base = OTHER
                        note = 2'-deoxyguanosine 3'-phosphorothioate
modified_base           16..17
                        mod_base = OTHER
                        note = 2'-MOE 5-methylcytidine 3'-phosphodiester
modified_base           18
                        mod_base = OTHER
                        note = 2'-MOE adenosine 3'-phosphodiester
modified_base           19
                        mod_base = OTHER
                        note = 2'-MOE 5-methylcytidine 3'-phosphorothioate
modified_base           20
                        mod_base = OTHER
                        note = 2'-MOE adenosine
SEQUENCE: 370
gaccgcttga gtttgccaca                                              20
```

COMPOSITIONS FOR MODULATING C9ORF72 EXPRESSION

CROSS-REFERENCE TO RELATED APPLICATIONS

This application is a continuation of U.S. application Ser. No. 16/546,283, filed Aug. 20, 2019, which is a continuation of U.S. application Ser. No. 14/436,024, filed Apr. 15, 2015, now U.S. Pat. No. 10,443,052, which is a national stage application under 35 U.S.C. § 371 of International Patent Application No. PCT/US2013/065073, filed Oct. 15, 2013, which claims the benefit of priority of U.S. Provisional Application No. 61/714,132, filed Oct. 15, 2012, each of which is incorporated by reference herein in its entirety for any purpose.

SEQUENCE LISTING

The present application contains a Sequence Listing which has been submitted electronically in XML format. Said XML copy, created on May 30, 2023, is named "BIOL0211SEQ.xml" and is 415,802 bytes in size. The information in the electronic format of the sequence listing is incorporated herein by reference in its entirety.

FIELD

Provided are compositions and methods for reducing expression of C9ORF72 mRNA and protein in an animal. Such methods are useful to treat, prevent, or ameliorate neurodegenerative diseases, including amyotrophic lateral sclerosis (ALS), frontotemporal dementia (FTD), cortical-basal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The chromosome 9p21ALS-FTD locus in the last major autosomal-dominant gene whose mutation is causative of ALS. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Provided herein are compositions and methods for modulating levels of C9ORF72 mRNA and protein in cells, tissues, and animals. In certain embodiments, C9ORF72 specific inhibitors modulate expression of C9ORF72 mRNA and protein. In certain embodiments, C9ORF72 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 mRNA levels are reduced. In certain embodiments, C9ORF72 protein levels are reduced. In certain embodiments, certain C9ORF72 mRNA variants are preferentially reduced. In certain embodiments, the C9ORF72 mRNA variants preferentially reduced are variants containing intron 1. In certain embodiments, intron 1 contains a hexanucleotide repeat expansion. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats. In certain embodiments, the hexanucleotide repeat expansion is associated with nuclear foci. In certain embodiments, the compositions and methods described herein are useful for reducing C9ORF72 mRNA levels, C9ORF72 protein levels, and nuclear foci. Such reduction can occur in a time-dependent manner or in a dose-dependent manner.

Also provided are methods useful for preventing, treating, and ameliorating diseases, disorders, and conditions associated with C9ORF72. In certain embodiments, such diseases, disorders, and conditions associated with C9ORF72 are neurodegenerative diseases. In certain embodiments, the neurodegenerative disease is amyotrophic lateral sclerosis (ALS), frontotemporal dementia (FTD), corticalbasal degeneration syndrome (CBD), atypical Parkinsonian syndrome, and olivopontocerellar degeneration (OPCD).

Such diseases, disorders, and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 specific inhibitor to an individual in need thereof. In certain embodiments, the C9ORF72 specific inhibitor is a nucleic acid. In certain embodiments, the nucleic acid is an antisense compound. In certain embodiments, the antisense compound is a single-stranded antisense oligonucleotide. In certain embodiments, the single-stranded antisense oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl group" (also 2'-MOE and 2'-$OCH_2CH_2$—$OCH_3$ and MOE) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-O-methoxyethyl group.

"5-methylcytosine" means a cytosine modified with a methyl group attached to the 5' position. A 5-methylcytosine is a modified nucleobase.

"About" means within +7% of a value. For example, if it is stated, "the compounds affected at least about 70% inhibition of C9ORF72", it is implied that the C9ORF72 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds. Antisense mechanisms include, without limitation, RNase H mediated antisense; RNAi mechanisms, which utilize the RISC pathway and include, without limitation, siRNA, ssRNA and microRNA mechanisms; and occupancy based mechanisms, including, without limitation uniform modified oligonucleotides. Certain antisense compounds may act through more than one such mechanism and/or through additional mechanisms.

"Antisense inhibition" means reduction of target nucleic acid levels or target protein levels in the presence of an antisense compound complementary to a target nucleic acid compared to target nucleic acid levels or target protein levels in the absence of the antisense compound. Inhibition may be any means including RNase H degradation, such as with a gapmer, and steric blockage, such as with a uniformly modified oligonucleotide.

"Antisense oligonucleotide" means a single-stranded oligonucleotide having a nucleobase sequence that permits hybridization to a corresponding segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 associated disease" means any disease associated with any C9ORF72 nucleic acid or expression product thereof. Such diseases may include a neurodegenerative disease. Such neurodegenerative diseases may include ALS and FTD.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise GGGGCC, GGGGGG, GGGGGC, or GGGGCG repeated at least 30 times. Such diseases may include a neurodegenerative disease. Such neurodegenerative diseases may include ALS and FTD.

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 (including genomic DNA comprising introns and exons), and an mRNA sequence encoding C9ORF72. "C9ORF72 mRNA" means an mRNA encoding a C9ORF72 protein.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of pharmaceutical agent sufficient to effectuate a desired physiological outcome in an individual in need of the pharmaceutical agent. The effective amount may vary among individuals depending on the health and physical condition of the individual to be treated, the taxonomic group of the individuals to be treated, the formulation of the composition, assessment of the individual's medical condition, and other relevant factors.

"Expression" means conversion of the information from a C9ORF72 gene into mRNA via transcription and then to protein via translation. Expression may result in a phenotypic manifestation of the C9ORF72 gene.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include an antisense compound and a target nucleic acid.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing expression of C9ORF72 mRNA and/or protein levels in the presence of a C9ORF72 specific inhibitor, including a C9ORF72 antisense oligonucleotide, as compared to expression of C9ORF72 mRNA and/or protein levels in the absence of a C9ORF72 specific inhibitor, such as a C9ORF72 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical agent" means the substance or substances in a pharmaceutical composition that provide a therapeutic benefit when administered to an individual. For example, in certain embodiments an antisense oligonucleotide targeted to C9ORF72 is a pharmaceutical agent.

"Pharmaceutical composition" means a mixture of substances suitable for administering to an individual. For example, a pharmaceutical composition may comprise one or more pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P═S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

CERTAIN EMBODIMENTS

Certain embodiments provide methods for decreasing C9ORF72 mRNA and protein expression.

Certain embodiments provide methods for the treatment, prevention, or amelioration of diseases, disorders, and conditions associated with C9ORF72 in an individual in need thereof. Also contemplated are methods for the preparation of a medicament for the treatment, prevention, or amelioration of a disease, disorder, or condition associated with C9ORF72. C9ORF72 associated diseases, disorders, and conditions include neurodegenerative diseases. In certain embodiments, the neurodegenerative disease may be ALS or FTD. In certain embodiments, the neurodegenerative disease may be familial or sporadic.

Certain embodiments provide for the use of a C9ORF72 specific inhibitor for treating, preventing, or ameliorating a C9ORF72 associated disease. Certain embodiments provide for the use of a C9ORF72 specific inhibitor for treating, preventing, or ameliorating a C9ORF72 hexanucleotide repeat expansion associated disease. In certain embodiments, the hexanucleotide repeat expansion may comprise GGGGCC, GGGGGG, GGGGGC, or GGGGCG. In certain embodiments, C9ORF72 specific inhibitors are nucleic acids (including antisense compounds), peptides, antibodies, small molecules, and other agents capable of inhibiting the expression of C9ORF72 mRNA and/or C9ORF72 protein.

Described herein are compounds comprising a single-stranded antisense oligonucleotide complementary to a C9ORF72 nucleic acid or a C9ORF72 homolog nucleic acid.

In certain embodiments, the C9ORF72 nucleic acid is a human C9ORF72 nucleic acid.

In certain embodiments, the C9ORF72 nucleic acid contains a hexanucleotide repeat expansion.

In certain embodiments, the C9ORF72 nucleic acid does not contain a hexanucleotide repeat expansion.

In certain embodiments, the single-stranded antisense oligonucleotide is specifically hybridizable to a human C9ORF72 nucleic acid.

In certain embodiments, the single-stranded antisense oligonucleotide is at least 75%, at least 80%, at least 85%, at least 90%, at least 95%, or 100% complementary to an equal length portion of a human C9ORF72 nucleic acid.

In certain embodiments, the single-stranded antisense oligonucleotide is complementary to any of exon, an intron, the 5' UTR, the 3' UTR, a repeat region, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a human C9ORF72 nucleic acid.

Described herein are compounds comprising a single-stranded antisense oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 contiguous nucleobases of SEQ ID NO: 30-369.

In certain embodiments, the single-stranded antisense oligonucleotide comprises at least one modification.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the single-stranded antisense oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-$(CH_2)_n$—O-2' bridge, wherein n is 1 or 2; and 4'-$CH_2$—O—$CH_2$-2'.

In certain embodiments, the bicyclic sugar comprises a 4'-$CH(CH_3)$—O-2' bridge.

In certain embodiments, the at least one modified nucleoside having a modified sugar comprises a non-bicyclic 2'-modified modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:

a gap segment consisting of linked deoxynucleosides;

a 5' wing segment consisting of linked nucleosides;

a 3' wing segment consisting of linked nucleosides;

wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned immediately adjacent and between the 5' wing segment and the 3' wing segment, wherein each nucleoside of each wing segment comprises a 2'-O— methoxyethyl sugar; and wherein each internucleoside linkage is a phosphorothioate linkage.

In certain embodiments, the single-stranded antisense oligonucleotide consists of 15 linked nucleosides.

In certain embodiments, the single-stranded antisense oligonucleotide consists of 16 linked nucleosides.

In certain embodiments, the single-stranded antisense oligonucleotide consists of 17 linked nucleosides.

In certain embodiments, the single-stranded antisense oligonucleotide consists of 18 linked nucleosides.

In certain embodiments, the single-stranded antisense oligonucleotide consists of 19 linked nucleosides.

In certain embodiments, the single-stranded antisense oligonucleotide consists of 20 linked nucleosides.

In certain embodiments, the single-stranded antisense oligonucleotide consists of 21 linked nucleosides.

In certain embodiments, the single-stranded antisense oligonucleotide consists of 22 linked nucleosides.

In certain embodiments, the single-stranded antisense oligonucleotide consists of 23 linked nucleosides.

In certain embodiments, the single-stranded antisense oligonucleotide consists of 24 linked nucleosides.

In certain embodiments, the single-stranded antisense oligonucleotide consists of 25 linked nucleosides.

Described herein are uses of the compound for the manufacture of a medicament for treating a neurodegenerative disease.

Provided herein are methods of preferentially inhibiting expression of mRNA transcripts containing a hexanucleotide repeat expansion by contacting a cell with an antisense oligonucleotide targeting upstream of exon 1B.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)_n$—O-2' bridge, where n=1 or n=2 and 4'-$CH_2$—O—$CH_2$-2'). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-10-4 gapmer motif.

In certain embodiments, antisense compounds targeted to a C9ORF72 nucleic acid possess a 4-10-4 gapmer motif.

In certain embodiments, antisense compounds targeted to a C9ORF72 nucleic acid possess a 4-10-3 gapmer motif.

In certain embodiments, antisense compounds targeted to a C9ORF72 nucleic acid possess a 5-9-5 gapmer motif.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-$(CH_2)_n$—O-2' bridge, wherein n is 1 or 2; and 4'-$CH_2$—O—$CH_2$-2'. In certain embodiments, the bicyclic sugar is comprises a 4'-CH($CH_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a C9ORF72 nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleosides is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group. In certain embodiments, uniformly modified antisense compounds may target C9ORF72, or any portion thereof, such as a hexanucleotide repeat expansion. In certain embodiments, targeting the hexanucleotide repeat expansion with a uniformly modified antisense compound reduces the repeat RNA by blocking the interaction with RNA binding proteins. In certain embodiments, this results in the toxic RNA being absent from foci and being degraded instead.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_l)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'—$(CH_2)_2$—O-2' (ENA); 4'-$CH(CH_3)$—O-2' and 4'-CH $(CH_2OCH_3)$—O-2' (and analogs thereof see U.S. Pat. No. 7,399,845, issued on Jul. 15, 2008); 4'-$C(CH_3)(CH_3)$—O-2'

(and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—(—$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron,* 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs,* 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Serial Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-$CH_2$-2',4'—($CH_2$)$_2$-2', 4'—($CH_2$)$_3$-2',4'—$CH_2$—O-2',4'—($CH_2$)$_2$—O-2',4'—$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-CH($CH_3$)—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

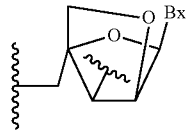

(A)

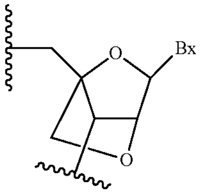

(B)

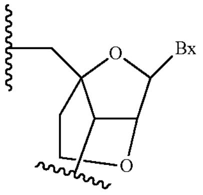

(C)

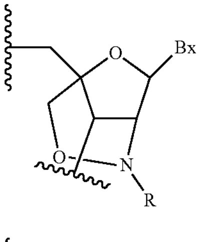

(D)

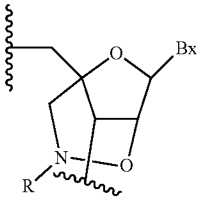

(E)

-continued (F)

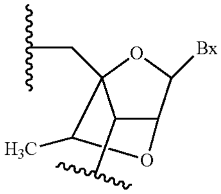

(G)

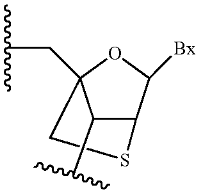

(H)

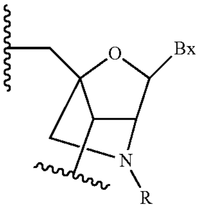

(I)

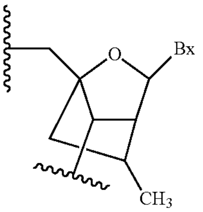

(J)

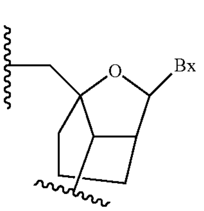

wherein Bx is the base moiety and R is independently H, a protecting group or $C_1$-$C_{12}$ alkyl.

In certain embodiments, bicyclic nucleosides are provided having Formula I:

I

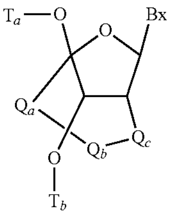

wherein:

Bx is a heterocyclic base moiety;

-$Q_a$-$Q_b$-$Q_c$- is —$CH_2$—$N(R_c)$—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

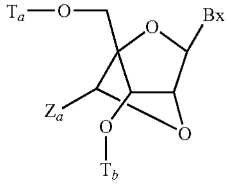

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_e$C(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

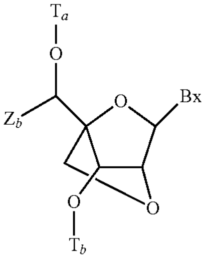

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

IV

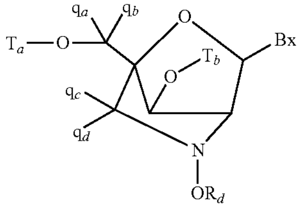

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

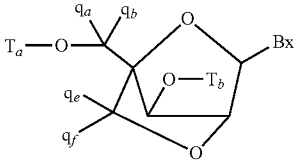

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C({=}O)OJ_j$, $C({=}O)NJ_jJ_k$, $C({=}O)J_j$, $O{-}C({=}O)NJ_jJ_k$, $N(H)C({=}NH)NJ_jJ_k$, $N(H)C({=}O)NJ_jJ_k$ or $N(H)C({=}S)NJ_jJ_k$;

or $q_e$ and $q_f$ together are $={C}(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

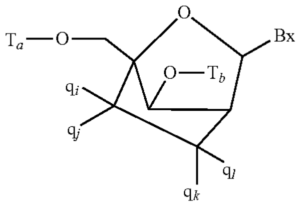

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C({=}O)OJ_j$, $C({=}O)NJ_jJ_k$, $C({=}O)J_j$, $O{-}C({=}O)NJ_jJ_k$, $N(H)C({=}NH)NJ_jJ_k$, $N(H)C({=}O)NJ_jJ_k$ or $N(H)C({=}S)NJ_jJ_k$; and $q_i$ and $q_j$ or $q_l$ and $q_k$ together are $={C}(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH—CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

VII

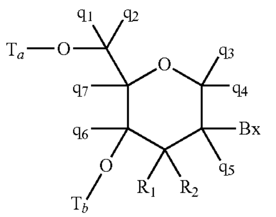

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassus, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides are mixed with LIPOFECTIN in OPTI-MEM 1 (Invitrogen, Carlsbad, CA) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of certain variants of C9ORF72. In certain embodiments, the antisense oligonucleotides described herein preferentially inhibit expression of variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Based on earlier studies directed to repeat expansions, it is not possible to predict if antisense oligonucleotides targeting C9ORF72 outside of the hexanucleotide repeat expansion would successfully inhibit expression of C9ORF72 for two reasons. First, the C9ORF72 repeat expansion is located in an intron and it is not known if the RNA in the foci contains only the repeats or also the flanking intronic sequence. For example, an earlier study on myotonic dystrophy type 2 (DM2), which is a disease caused by a CCTG expansion mutation in intron 1 of the ZNF9 gene, determined that large DM2 expansions did not prevent allele-specific pre-mRNA splicing, nuclear export of the transcripts, or steady-state mRNA or protein levels. The study further demonstrated that the ribonuclear inclusions found associated with the disease are enriched for the CCUG expansion, but not the flanking intronic sequences. These data suggest that the downstream molecular effects of the DM2 mutation may be triggered by the accumulation of CCUG repeat tract alone. Therefore, this study implies that targeting the CCUG repeat expansion alone would lead to amelioration of the disease, since targeting the flanking sequences, especially the region downstream of the repeat expansion, would not affect the formation of ribonuclear inclusions (Margolis et al. Hum. Mol. Genet., 2006, 15:1808-1815). Second, it is not known how fast intron 1 of C9ORF72, which contains the repeats, is excised and accumulates in foci. Thus, it is not possible to predict if targeting the pre-mRNA would result in elimination of the repeat RNA and foci.

C9OFF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human C9ORF72 in HepG2 Cells

Antisense oligonucleotides were designed targeting a C9ORF72 nucleic acid and were tested for their effects on C9ORF72 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 7,000 nM antisense oligonucleotide. After a treatment period of approximately 24 hours, RNA was isolated from the cells and C9ORF72 mRNA levels were measured by quantitative real-time PCR. Human primer probe set RTS3750 (forward sequence TGTGACAGTTGGAATGCAGTGA, designated herein as SEQ ID NO: 15: reverse sequence GCCACTTAAAGCAATCTCTGTCTTG, designated herein as SEQ ID NO: 16: probe sequence TCGACTCTTTGCCCACCGCCA, designated herein as SEQ ID NO: 17) was used to measure mRNA levels. C9ORF72 mRNA levels were adjusted according to total RNA content, as measured by RIBOGREEN®. Results are presented as percent inhibition of C9ORF72, relative to untreated control cells.

The antisense oligonucleotides in Tables 6-10 were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages throughout each gapmer are phosphorothioate linkages. All cytosine residues throughout each gapmer are 5-methylcytosines. "Start site" indicates the 5'-most nucleoside to which the antisense oligonucleotide is targeted in the human gene sequence. "Stop site" indicates the 3'-most nucleoside to which the antisense oligonucleotide is targeted human gene sequence. Each antisense oligonucleotide listed in Tables 6-9 is targeted to the either human C9ORF72 mRNA sequence, designated herein as SEQ ID NO: 1 (GENBANK Accession No. NM_001256054.1) or the human C9ORF72 genomic sequence, designated herein as SEQ ID NO: 2 (the complement of GENBANK Accession No. NT_008413.18 truncated from nucleosides 27535000 to 27565000), or both. 'n/a' indicates that the antisense oligonucleotide did not target that particular gene sequence. The antisense oligonucleotides of Table 10 are targeted to either SEQ ID NO: 3 (GENBANK Accession No. BQ068108.1) or SEQ ID NO: 4 (GENBANK Accession No. NM_018325.3).

As shown in Tables 6-10, below, several of the oligonucleotides targeting SEQ ID NO: 1 exhibit at least 50% inhibition, including those targeted to nucleobases 90-647, 728-1541, 1598-1863, 1935-2146, 2232-2251, 2429-2576, 2632-2743, 2788-2807, 2860-2879, 2949-2968, 3062-3081, 3132-3151, and 3250-3269 of SEQ ID NO 1. These include SEQ ID NOs: 32, 33, 34, 35, 36, 37, 38, 40, 41, 42, 43, 44, 45, 46, 47, 50, 51, 53, 55, 56, 57, 61, 62, 64, 66, 67, 72, 73, 75, 76, 81, 82, 85, 89, 90, 91, 92, 93, 94, 96, 97, 100, 102, 103, 109, 111, 112, 115, 116, 117, 118, 119, 120, 121, 122, 123, 124, 125, 126, 130, 131, 132, 133, 137, 139, 140, 141, 145, 146, 149, 150, 151, 152, 153, 154, 165, 166, 168, 169, 170, 171, 174, 179, 181, 182, 183, 185, 186, 187, 188, 190, 192, 195, 197, 199, 320, 321, 322, 323, 324, 325, 326, 327, 328, 329, 330, 331, and 332. Several of the oligonucleotides exhibit at least 70% inhibition, including those targeted to nucleobases 90-359, 430-479, 550-569, 617-647, 940-959, 1013-1033, 1446-1465, 1687-1706, 1844-1863, 1935-2007, and 2679-2698 of SEQ ID NO 1. These include SEQ ID NOs: 32, 33, 34, 35, 36, 40, 41, 42, 43, 44, 47, 66, 67, 85, 96, 103, 117, 119, 154, 165, 168, 186, 320, 321, 324, 327, 328, and 331. Several of the oligonucleotides exhibit at least 80% inhibition, including those targeted to nucleobases 90-265 and 310-329. These include SEQ ID NOs: 32, 33, 35, 40, 42, and 321. Several of the oligonucleotides exhibit at least 90% inhibition, including those targeted to nucleobases 190-209 and 310-329 of SEQ ID NO 1. These include SEQ ID NOs: 40 and 321.

As shown in Tables 6-20, below, several of the oligonucleotides targeting SEQ ID NO: 2 exhibit at least 50% inhibition, including those targeted to nucleobases 1552-1572, 2187-2238, 2728-2779, 3452-2471, 3752-3771, 5025-5044, 5656-5675, 6200-6219, 7594-7613, 7840-8328, 9415-9434, 12526-12545, 13357-13524, 13642-13661, 13790-14130, 14243-14335, 14699-14777, 15587-15606, 16395-16488, 18233-18373, 24306-24340, 24472-24491, 24565-24676, 26400-26424, 26606-26982, 27054-27265, 27351-27370, 27548-27998, 28068-28087, 28181-28270, and 28369-28388 of SEQ ID NO 2. These include SEQ ID NOs: 32, 33, 34, 35, 36, 37, 38, 40, 41, 42, 43, 44, 45, 46, 47, 50, 51, 53, 55, 56, 57, 64, 67, 72, 73, 75, 76, 81, 82, 85, 89, 90, 91, 92, 93, 94, 96, 97, 100, 102, 103, 111, 112, 115, 117, 118, 119, 121, 122, 123, 124, 125, 126, 130, 131, 132, 133, 137, 139, 140, 141, 145, 146, 149, 150, 151, 152, 153, 154, 165, 166, 168, 169, 170, 171, 174, 179, 181, 182, 183, 185, 186, 187, 188, 190, 192, 195, 197, 199, 205, 206, 208, 211, 212, 224, 226, 230, 231, 250, 251, 252, 256, 300, 301, 304, 306, 307, 310, 320, 321, 322, 323, 324, 325, 326, 327, 328, 329, 330, 331, and 332. Several of the oligonucleotides exhibit at least 70% inhibition, including those targeted to nucleobases 3452-2471, 7840-8159, 8230-8249, 12526-12545, 13642-13661, 14075-14094, 14316-14335, 14758-14777, 16395-16414, 16469, 16488, 24655-24674, 26963, 26982, 27054-27126, and 27798-27817 of SEQ ID NO 2. These include SEQ ID NOs: 32, 33, 34, 35, 36, 40, 41, 42, 43, 44, 47, 67, 85, 96, 103, 117, 119, 154, 165, 168, 186, 251, 306, 320, 321, 324, 327, 328, and 331. Several of the oligonucleotides exhibit at least 80% inhibition, including those targeted to nucleobases 7848-8023 of SEQ ID NO 2. These include SEQ ID NOs: 32, 33, 35, 40, 42, and 321. Several of the oligonucleotides exhibit at least 90% inhibition, including those targeted to nucleobases 7870-7889 and 7990-8009 of SEQ ID NO 2. These include SEQ ID NOs: 40 and 321.

TABLE 6

| Target Start Site at SEQ ID NO: 1 | Target Start Site at SEQ ID NO: 2 | Sequence | ISIS No | % inhibition | SEQ ID NO |
|---|---|---|---|---|---|
| 3 | 1139 | AGCGGGACACCGTAGGTTAC | 576883 | 0 | 30 |
| 44 | 1180 | GTGGGCGGAACTTGTCGCTG | 576807 | 1 | 31 |
| 90 | 7848 | GTCACATTATCCAAATGCTC | 576808 | 85 | 32 |
| 125 | 7883 | GGTGGGCAAAGAGTCGACAT | 576809 | 82 | 33 |
| 155 | 7913 | ATCTCTGTCTTGGCAACAGC | 576810 | 78 | 34 |
| 160 | 7918 | AAGCAATCTCTGTCTTGGCA | 576811 | 81 | 35 |

TABLE 6-continued

| Target Start Site at SEQ ID NO: 1 | Target Start Site at SEQ ID NO: 2 | Sequence | ISIS No | % inhibition | SEQ ID NO |
|---|---|---|---|---|---|
| 165 | 7923 | ACTTAAAGCAATCTCTGTCT | 576812 | 78 | 36 |
| 170 | 7928 | TTGCCACTTAAAGCAATCTC | 576813 | 67 | 37 |
| 205 | 7963 | CCCAGTAAGCAAAAGTAGCT | 576814 | 66 | 38 |
| 227 | 7985 | ACTCTAGGACCAAGAATATT | 576815 | 11 | 39 |
| 232 | 7990 | GCCTTACTCTAGGACCAAGA | 576816 | 78 | 40 |
| 240 | 7998 | CCAAATGTGCCTTACTCTAG | 576817 | 73 | 41 |
| 246 | 8004 | TGGAGCCCAAATGTGCCTTA | 576818 | 81 | 42 |
| 254 | 8012 | TCTGTCTTTGGAGCCCAAAT | 576819 | 76 | 43 |
| 275 | 8033 | CCATCACTGAGAAGTACCTG | 576820 | 79 | 44 |
| 281 | 8039 | ATTTCTCCATCACTGAGAAG | 576821 | 61 | 45 |
| 288 | 8046 | AAAAGTTATTTCTCCATCAC | 576822 | 57 | 46 |
| 295 | 8053 | TGGCAAGAAAAGTTATTTCT | 576823 | 70 | 47 |
| 302 | 8060 | GTGTGGTTGGCAAGAAAAGT | 576824 | 44 | 48 |
| 313 | 8071 | CTCCATTTAGAGTGTGGTTG | 576825 | 39 | 49 |
| 330 | 8088 | TGCATTTCGAAGGATTTCTC | 576826 | 65 | 50 |
| 338 | 8096 | CCACTCTCTGCATTTCGAAG | 576827 | 67 | 51 |
| 362 | 8120 | ACAAAAAACTTTACATCTAT | 576828 | 22 | 52 |
| 376 | 8134 | CCTTTTCAGACAAGACAAAA | 576829 | 53 | 53 |
| 401 | 8159 | AAGATTAATGAAACAATAAT | 576830 | 0 | 54 |
| 411 | 8169 | GTTTCCATCAAAGATTAATG | 576831 | 62 | 55 |
| 446 | 8204 | ATTGATAGTCCATATGTGCT | 576832 | 59 | 56 |
| 452 | 8210 | AGTATAATTGATAGTCCATA | 571818 | 57 | 57 |
| 481 | 8239 | GGAGGTAGAAACTAAGTTCT | 576833 | 45 | 58 |
| 516 | 8274 | ATGTGTTAATCTATCAACAC | 576834 | 48 | 59 |
| 545 | 8303 | TGCATCCATATTCTTCCTTT | 576835 | 43 | 60 |
| 552 | n/a | TTCCTTATGCATCCATATTC | 576836 | 64 | 61 |
| 559 | n/a | CTTGTCTTTCCTTATGCATC | 576837 | 57 | 62 |
| 566 | n/a | ACATTTTCTTGTCTTTCCTT | 576838 | 43 | 63 |
| 571 | 9415 | TCTGGACATTTTCTTGTCTT | 576839 | 61 | 64 |
| 578 | 9422 | ATAATCTTCTGGACATTTTC | 576840 | 37 | 65 |
| 617 | n/a | CTCTGACCCTGATCTTCCAT | 576841 | 79 | 66 |
| 628 | 12526 | TTGGAATAATACTCTGACCC | 576842 | 73 | 67 |
| 663 | 12561 | CAGTTCCATTACAGGAATCA | 576843 | 45 | 68 |
| 697 | 12595 | CTTCAGGAACACTGTGTGAT | 576844 | 20 | 69 |
| 705 | 12603 | ATCTATTTCTTCAGGAACAC | 576845 | 46 | 70 |
| 722 | n/a | AGTACTGTATCAGCTATATC | 576846 | 46 | 71 |
| 728 | 13357 | TCATTGAGTACTGTATCAGC | 576847 | 52 | 72 |

TABLE 6-continued

| Target Start Site at SEQ ID NO: 1 | Target Start Site at SEQ ID NO: 2 | Sequence | ISIS No | % inhibition | SEQ ID NO |
|---|---|---|---|---|---|
| 734 | 13363 | TCATCATCATTGAGTACTGT | 576848 | 67 | 73 |
| 740 | 13369 | CCAATATCATCATCATTGAG | 576849 | 47 | 74 |
| 755 | 13384 | TCATGACAGCTGTCACCAAT | 576850 | 51 | 75 |
| 761 | 13390 | AAGCCTTCATGACAGCTGTC | 576851 | 52 | 76 |
| 767 | 13396 | AGAAGAAAGCCTTCATGACA | 576852 | 23 | 77 |
| 773 | 13402 | TACTTGAGAAGAAAGCCTTC | 576853 | 24 | 78 |
| 778 | 13407 | ATTCTTACTTGAGAAGAAAG | 576854 | 12 | 79 |
| 782 | 13411 | AAAAATTCTTACTTGAGAAG | 576855 | 0 | 80 |
| 817 | 13446 | AGATGGTATCTGCTTCATCC | 576856 | 61 | 81 |
| 876 | 13505 | CAATCTAAGTAGACAGTCTG | 576857 | 57 | 82 |
| 911 | 13540 | TTAAGCAACAGTTCAAATAC | 576858 | 40 | 83 |
| 978 | 13607 | CTTTAAATAGCAAATGGAAT | 576859 | 26 | 84 |
| 1013 | 13642 | GCCATGATTTCTTGTCTGGG | 576860 | 79 | 85 |
| 1056 | 13685 | GCTTTAATGAGAAGTAAAAC | 576861 | 17 | 86 |
| 1091 | 13720 | TCTACAGTACAACTTAATAT | 576862 | 39 | 87 |
| 1126 | 13755 | ATAATTTTGTTCTACGCCTA | 576863 | 44 | 88 |
| 1161 | 13790 | CACTGCTGGATGGAAAAAGA | 576864 | 65 | 89 |
| 1196 | 13825 | TGGTTTAAGGGCACAAACTC | 576865 | 52 | 90 |
| 1231 | 13860 | TTGCCCACGGGTACACAGCA | 576866 | 63 | 91 |
| 1268 | 13897 | CAGATGAGGAAATAGGTGTA | 576867 | 62 | 92 |
| 1303 | 13932 | ACACATTAGGTACTATTACT | 576868 | 63 | 93 |
| 1372 | 14001 | TTTTTATGTTCCAGGCACTG | 576869 | 59 | 94 |
| 1407 | 14036 | AATAGGAAATGTTAGCTATG | 576870 | 30 | 95 |
| 1446 | 14075 | GGCACTCAACAAATACTGGC | 576871 | 72 | 96 |
| 1482 | 14111 | TACATGTAAAGCAACTAGTA | 576872 | 55 | 97 |
| 1539 | 14168 | TAAAATTTCATGAAAATCTG | 576873 | 0 | 98 |
| 1579 | 14208 | AAGTGAATACTTTATACTTT | 576874 | 0 | 99 |
| 1614 | 14243 | CATCATGAGCCTAAAGGAAA | 576875 | 51 | 100 |
| 1651 | 14280 | GGCTCTTAGGTTAAACACAC | 576876 | 43 | 101 |
| 1673 | 14302 | TGCTTCTGATTCAAGCCATT | 576877 | 65 | 102 |
| 1687 | 14316 | ATACAGGACTAAAGTGCTTC | 576878 | 74 | 103 |
| 1731 | 14360 | CAAATGGGATTTAAAATGAT | 576879 | 0 | 104 |
| 1766 | 14395 | TGACATGTAGAGAGATTAAG | 576880 | 26 | 105 |
| 1801 | 14430 | TTATTGAAATACCATCATTT | 576881 | 34 | 106 |
| 1836 | 14465 | TAGTCAGTATAATATCATTT | 576882 | 18 | 107 |

TABLE 7

| Target Start Site at SEQ ID NO: 1 | Target Start Site at SEQ ID NO: 2 | Sequence | ISIS No | % inhibition | SEQ ID NO |
|---|---|---|---|---|---|
| 851 | n/a | GCATTGAGAAGAAAGCCTTC | 571824 | 25 | 108 |
| 1337 | n/a | AAGACCTGATCCAGGAAGGC | 571836 | 53 | 109 |
| 861 | n/a | TGAGCTGATGGCATTGAGAA | 571981 | 41 | 110 |
| 890 | 14726 | ACAACGGAACAGCCACAGGT | 571983 | 66 | 111 |
| 1420 | 26405 | TTAGTGTCAAGGCTTTTCTG | 572007 | 60 | 112 |
| 75 | 1211 | GACGGCTGACACACCAAGCG | 576884 | 8 | 113 |
| 856 | n/a | TGATGGCATTGAGAAGAAAG | 576891 | 6 | 114 |
| 917 | 14753 | TTTACTTTCTCTGCACTGCT | 576892 | 68 | 115 |
| 922 | n/a | TCTTATTTACTTTCTCTGCA | 576893 | 63 | 116 |
| 940 | 16395 | GGCATAATGTTCTGACTATC | 576894 | 71 | 117 |
| 979 | 16434 | ATAACCTGGAGCATTTTCTC | 576895 | 65 | 118 |
| 1014 | 16469 | CCCTGACTCATATTTAAATG | 576896 | 70 | 119 |
| 1049 | n/a | CCAGTTGAATCCTTTAGCAG | 576897 | 51 | 120 |
| 1084 | 18233 | CATACATGACTTGCCGGAAA | 576898 | 66 | 121 |
| 1119 | 18268 | GACATCCACATCTATGTGTG | 576899 | 63 | 122 |
| 1154 | 18303 | TGTTCATGACAGGGTGGCAT | 576900 | 66 | 123 |
| 1163 | 18312 | TTATAAATATGTTCATGACA | 576901 | 51 | 124 |
| 1191 | 18340 | CAGCTCGGATCTCATGTATC | 576902 | 52 | 125 |
| 1205 | 18354 | CTCCAGAAGGCTGTCAGCTC | 576903 | 59 | 126 |
| 1238 | 18387 | GTATCCTGAGCCATGTCTTC | 576904 | 33 | 127 |
| 1273 | 18422 | AATCAGGAGTAAAGCTTTCG | 576905 | 48 | 128 |
| 1283 | n/a | AAAATATTCAAATCAGGAGT | 576906 | 23 | 129 |
| 1304 | 24306 | TCTCTGTGTAAGACATCTTG | 576907 | 51 | 130 |
| 1309 | 24311 | GAGTGTCTCTGTGTAAGACA | 576908 | 54 | 131 |
| 1314 | 24316 | CACTAGAGTGTCTCTGTGTA | 576909 | 50 | 132 |
| 1319 | 24321 | GCTTTCACTAGAGTGTCTCT | 576910 | 60 | 133 |
| 1330 | 24332 | GATCCAGGAAGGCTTTCACT | 576911 | 35 | 134 |
| 1373 | 26358 | AAAGTACTTCTGAGAGATAA | 576912 | 38 | 135 |
| 1385 | 26370 | AACTGTGCAAGGAAAGTACT | 576913 | 43 | 136 |
| 1415 | 26400 | GTCAAGGCTTTTCTGTGAAG | 576914 | 65 | 137 |
| 1472 | 26591 | AGAGATTTAAAGGGCTTTTT | 576915 | 46 | 138 |
| 1487 | 26606 | ATCTTCAGGTTCCGAAGAGA | 576916 | 53 | 139 |
| 1511 | 26630 | CCCTCTGCTGTTAAATCAAG | 576917 | 51 | 140 |
| 1522 | 26641 | TGTTAAGATCGCCCTCTGCT | 576918 | 64 | 141 |
| 1529 | 26648 | ATTATTATGTTAAGATCGCC | 576919 | 46 | 142 |
| 1535 | 26654 | AGAGCCATTATTATGTTAAG | 576920 | 36 | 143 |
| 1571 | 26690 | ATAAAAGAGTGTAGGCCTGG | 576921 | 46 | 144 |

TABLE 7-continued

| Target Start Site at SEQ ID NO: 1 | Target Start Site at SEQ ID NO: 2 | Sequence | ISIS No | % inhibition | SEQ ID NO |
|---|---|---|---|---|---|
| 1598 | 26717 | ACACTAGTGTAGAAAGGTCT | 576922 | 55 | 145 |
| 1606 | 26725 | GTTCTTGCACACTAGTGTAG | 576923 | 62 | 146 |
| 1628 | 26747 | TAAAAAGTCATTAGAACATC | 576924 | 10 | 147 |
| 1644 | 26763 | TATTAAGTTACACATTTAAA | 576925 | 20 | 148 |
| 1679 | 26798 | CTTTACCAGCGATCATGATT | 576926 | 57 | 149 |
| 1725 | 26844 | TTCTGGAGTATGATCCAGGG | 576927 | 64 | 150 |
| 1752 | 24472<br>26871 | ACTTAACTGCAATTGCTGAG | 576928 | 66 | 151 |
| 1765 | 26884 | TGTAGTGTAACTTACTTAAC | 576929 | 60 | 152 |
| 1802 | 26921 | ATGCACCTGACATCCCCTCA | 576930 | 56 | 153 |
| 1844 | 26963 | CCCAAAAGCATAAATCTAGG | 576931 | 71 | 154 |
| 1876 | 24596<br>26995 | ATATTTATTATATTGTAAAC | 576932 | 0 | 155 |
| 1883 | 24603<br>27002 | AGCAATAATATTTATTATAT | 576933 | 1 | 156 |
| 1887 | 24607<br>27006 | AGATAGCAATAATATTTATT | 576934 | 0 | 157 |
| 1889 | 24609<br>27008 | AAAGATAGCAATAATATTTA | 576935 | 0 | 158 |
| 1892 | 24612<br>27011 | TTAAAAGATAGCAATAATAT | 576936 | 3 | 159 |
| 1896 | 24616<br>27015 | ATCTTTAAAAGATAGCAATA | 576937 | 14 | 160 |
| 1898 | 24618<br>27017 | ATATCTTTAAAAGATAGCAA | 576938 | 15 | 161 |
| 1901 | 24621<br>27020 | ATTATATCTTTAAAAGATAG | 576939 | 12 | 162 |
| 1905 | 24625<br>27024 | TATTATTATATCTTTAAAAG | 576940 | 6 | 163 |
| 1918 | 27037 | CAAGTTTACATCCTATTATT | 576941 | 48 | 164 |
| 1935 | 24655<br>27054 | AAAACAGTAGTTGTGGTCAA | 576942 | 77 | 165 |
| 1937 | 24657<br>27056 | AAAAAACAGTAGTTGTGGTC | 576943 | 69 | 166 |
| 1953 | 27072 | TGAATCATGTATTTCAAAAA | 576944 | 17 | 167 |
| 1988 | 27107 | GCCAACTCAGATTTCACCTT | 576945 | 71 | 168 |
| 2036 | 27155 | CTACACACCAAAGAATGCCA | 576946 | 69 | 169 |
| 2071 | 27190 | AGTTTTCAGTTGATTGCAGA | 576947 | 58 | 170 |
| 2127 | 27246 | CATCCTATGTTCAAGCTCAC | 576948 | 51 | 171 |
| 2162 | 27281 | TAAACATCTGCTTGATCAAT | 576949 | 44 | 172 |
| 2197 | 27316 | AATCCACAAAGTAGGATCTA | 576950 | 42 | 173 |
| 2232 | 27351 | ATTAGACATTTCTACAGACT | 576951 | 56 | 174 |
| 2325 | 27444 | CTCAACTACATAGAATATCA | 576952 | 45 | 175 |

TABLE 7-continued

| Target Start Site at SEQ ID NO: 1 | Target Start Site at SEQ ID NO: 2 | Sequence | ISIS No | % inhibition | SEQ ID NO |
|---|---|---|---|---|---|
| 2371 | 27490 | TTGGCAACAATTACTAAAAC | 576953 | 48 | 176 |
| 2400 | 27519 | TCAAAAATAATGAAAATTAA | 576954 | 0 | 177 |
| 2409 | 27528 | CAATTTGGCTCAAAAATAAT | 576955 | 3 | 178 |
| 2429 | 27548 | GGCACAGGAGGTGCACATTT | 576956 | 60 | 179 |

TABLE 8

| Target Start Site at SEQ ID NO: 1 | Target Start Site at SEQ ID NO: 2 | Sequence | ISIS No | % inhibition | SEQ ID NO |
|---|---|---|---|---|---|
| 2451 | 27570 | TAGATTTTCTAAGGAGAAAA | 576957 | 8 | 180 |
| 2486 | 27605 | ACTGACCAGTGAAATCTGAA | 576958 | 50 | 181 |
| 2522 | 27641 | GGTAAGACTTAGCAAGAAGA | 576959 | 59 | 182 |
| 2557 | 27676 | TCTCAGAGTTGCAATGATTG | 576960 | 63 | 183 |
| 2597 | 27716 | AGATCTTATTAGTTAGTATA | 576961 | 18 | 184 |
| 2632 | 27751 | AGTACTCAAGGAACTATTTT | 576962 | 57 | 185 |
| 2679 | 27798 | GGCAAACAGCAACAACTTCA | 576963 | 71 | 186 |
| 2724 | 27843 | GCACTTCAGTAAAATTTCTC | 576964 | 69 | 187 |
| 2788 | 27907 | GGTCCAAACGCATTAAGAAA | 576965 | 58 | 188 |
| 2825 | 27944 | GAATTATATTAATCAGTTAT | 576966 | 0 | 189 |
| 2860 | 27979 | TGTGTTTGTGTAACTACAAT | 576967 | 67 | 190 |
| 2895 | 28014 | ATATTACTTCCAGAATTTTA | 576968 | 19 | 191 |
| 2949 | 28068 | GGCAGAAGGGCTCTATTACC | 576969 | 59 | 192 |
| 2992 | 28111 | CATTCGAACATGTCATTTTG | 576970 | 40 | 193 |
| 3027 | 28146 | CTGATTCATGATGGGAAAGC | 576971 | 34 | 194 |
| 3062 | 28181 | GTGGTTGTCTAAAACATCAA | 576972 | 58 | 195 |
| 3097 | 28216 | ATGACTGAGCTACAGTACAA | 576973 | 47 | 196 |
| 3132 | 28251 | GGGACACTACAAGGTAGTAT | 576974 | 56 | 197 |
| 3167 | 28286 | TTAAATAAGAATCTACCATG | 576975 | 12 | 198 |
| 3250 | 28369 | GCTTTAATAACTTATTTCAC | 576976 | 54 | 199 |
| 3282 | 28401 | AGGAGAAAAGATATATAACA | 576977 | 0 | 200 |
| 3288 | 28407 | CCATTTAGGAGAAAAGATAT | 576978 | 0 | 201 |
| n/a | 1343 | TTCACCCTCAGCGAGTACTG | 576979 | 0 | 202 |
| n/a | 1403 | AGGCTGCGGTTGTTTCCCTC | 576980 | 0 | 203 |
| n/a | 1800 | GCCAGATCCCCATCCCTTGT | 576981 | 11 | 204 |
| n/a | 2187 | TCACTTCCTTTAAGCAAGTC | 576982 | 52 | 205 |
| n/a | 2209 | AGTGATGCCCAAGTCACAAT | 576983 | 53 | 206 |
| n/a | 2214 | AGTCAAGTGATGCCCAAGTC | 576984 | 47 | 207 |

TABLE 8-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 2219 | CCATCAGTCAAGTGATGCCC | 576985 | 60 | 208 |
| n/a | 2224 | GATTACCATCAGTCAAGTGA | 576986 | 29 | 209 |
| n/a | 2229 | CAACTGATTACCATCAGTCA | 576987 | 42 | 210 |
| n/a | 2728 | GCAGTTTCCAACTGATTCAG | 576988 | 58 | 211 |
| n/a | 2760 | CGTTCTTGTTTCAGATGTAC | 576989 | 57 | 212 |
| n/a | 2862 | GCCAAACAAAATATTTTATC | 576990 | 22 | 213 |
| n/a | 2995 | TAGGTAGGCTAACCTAGTCC | 576991 | 47 | 214 |
| n/a | 3196 | TCCCAGCCCAAAGAGAAGCA | 576992 | 41 | 215 |
| n/a | 3466 | GGATCATAGCTCTCGGTAAC | 576993 | 26 | 216 |
| n/a | 3540 | AATCATAAAGCCCTCACTTC | 576994 | 7 | 217 |
| n/a | 3595 | CTGATTGGTATTTAGAAAGG | 576995 | 3 | 218 |
| n/a | 3705 | ATGCAGACATGATTACATTA | 576996 | 48 | 219 |
| n/a | 4560 | TTCATCATTAAACTGAAAAT | 576997 | 0 | 220 |
| n/a | 4613 | CTTTTAGGTTAAAAAGGTGG | 576998 | 35 | 221 |
| n/a | 4986 | ATACAGAGCCTGGCAAAACA | 576999 | 30 | 222 |
| n/a | 5036 | TTCTATTTACAGAGCATTAG | 577000 | 29 | 223 |
| n/a | 5656 | GCCTTCACATTAATTCACCA | 577001 | 62 | 224 |
| n/a | 6051 | TGTGTTATTGCCCCTAAAAA | 577002 | 24 | 225 |
| n/a | 6200 | TGTATTCACTATACTATGCC | 577003 | 52 | 226 |
| n/a | 6276 | AAGTTATTTAAAGTATAGCA | 577004 | 0 | 227 |
| n/a | 6762 | GACATTGAAGTATCAAGACA | 577005 | 34 | 228 |
| n/a | 6965 | TGTTAAGTAATCTTAGAAAA | 577006 | 0 | 229 |
| n/a | 7594 | GGCATACATTTAGAAATTCA | 577007 | 60 | 230 |
| n/a | 8309 | ACCTTATGCATCCATATTCT | 577008 | 59 | 231 |
| n/a | 8784 | GAATTCTCTTGGGAACCATT | 577009 | 42 | 232 |
| n/a | 8834 | ATATTCAACTACAGGATTTA | 577010 | 13 | 233 |
| n/a | 8884 | ATGTGTTCTTTAGATACATC | 577011 | 42 | 234 |
| n/a | 9510 | CCTTATACAGATACATGCTG | 577012 | 37 | 235 |
| n/a | 9663 | TAGATGCAATTACTATTTTC | 577013 | 34 | 236 |
| n/a | 10742 | TGTACTTCCCAAACTTGAAC | 577014 | 24 | 237 |
| n/a | 10845 | CTGAAGCTCAACAACACCAA | 577015 | 49 | 238 |
| n/a | 11684 | GTCTATAGAATCAAACTGAA | 577016 | 38 | 239 |
| n/a | 11851 | TTGAATCAATACCTAACCTC | 577017 | 23 | 240 |
| n/a | 11991 | TGCCTCTTTTAGAAAAGATC | 577018 | 44 | 241 |
| n/a | 12042 | ATGGAATCATTGGTTTATCG | 577019 | 43 | 242 |
| n/a | 12069 | AAAGCTCACTTTTATTCTTT | 577020 | 37 | 243 |
| n/a | 12333 | | | | |

TABLE 8-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 12170 | GGTGCCGCCACCATGCCCGG | 577021 | 0 | 244 |
| n/a | 12464 | GAGAGAAGCTGGGCAATAAA | 577022 | 2 | 245 |
| n/a | 12514 | TCTGACCCTGCACAATAAAG | 577023 | 0 | 246 |
| n/a | 13016 | ATAGTGTGTGATTCAAAACG | 577024 | 17 | 247 |
| n/a | 13348 | ACTGTATCAGCTATCTAAAA | 577025 | 22 | 248 |
| n/a | 14540 | TTATTTGTATAGGAACCTAC | 577026 | 44 | 249 |
| n/a | 14699 | TGTGAGCTGATGGCACTGTA | 577027 | 61 | 250 |
| n/a | 14758 | CCTTATTTACTTTCTCTGCA | 577028 | 71 | 251 |
| n/a | 15587 | GGAATAAGGTCACTAGTTCG | 577029 | 69 | 252 |
| n/a | 17187 | ATTTGCAACAATTTTTAAAT | 577030 | 8 | 253 |
| n/a | 21808 | ATAAACTACCAATGATATCC | 577031 | 13 | 254 |
| n/a | 24337 | TACCTGATCCAGGAAGGCTT | 577032 | 40 | 255 |
| n/a | 24565 | TTCCCGAAGCATAAATCTAG | 577033 | 53 | 256 |
| n/a | 25549 | TTGAGAAGCATGAAATTCCA | 577034 | 48 | 257 |

TABLE 9

| Target Start Site at SEQ ID NO: 1 | Target Start Site at SEQ ID NO: 2 | Sequence | ISIS No | % inhibition | SEQ ID NO |
|---|---|---|---|---|---|
| 310 | 7990 | GCCTTACTCTAGGACCAAGA | 576816 | 90 | 40 |
| 75 | 1211 | GACGGCTGACACACCAAGCG | 576884 | 0 | 113 |
| 2 | 1138 | GCGGGACACCGTAGGTTACG | 577035 | 0 | 258 |
| 10 | 1146 | CTTTCCTAGCGGGACACCGT | 577036 | 1 | 259 |
| 18 | 1154 | GCACCTCTCTTTCCTAGCGG | 577037 | 0 | 260 |
| 26 | 1162 | TGTTTGACGCACCTCTCTTT | 577038 | 0 | 261 |
| 34 | 1170 | CTTGTCGCTGTTTGACGCAC | 577039 | 0 | 262 |
| 42 | 1178 | GGGCGGAACTTGTCGCTGTT | 577040 | 0 | 263 |
| 83 | 1219 | GCAGCAGGGACGGCTGACAC | 577041 | 0 | 264 |
| 95 | 1231 | AGAAGCAACCGGGCAGCAGG | 577042 | 0 | 265 |
| 103 | 1239 | CCCAAAAGAGAAGCAACCGG | 577043 | 0 | 266 |
| 111 | 1247 | ACCCCGCCCCCAAAAGAGAA | 577044 | 1 | 267 |
| 119 | 1255 | CTTGCTAGACCCCGCCCCCA | 577045 | 0 | 268 |
| 127 | 1263 | CACCTGCTCTTGCTAGACCC | 577046 | 0 | 269 |
| 135 | 1271 | TAAACCCACACCTGCTCTTG | 577047 | 0 | 270 |
| 139 | 1275 | CTCCTAAACCCACACCTGCT | 577048 | 0 | 271 |
| n/a | 1283 | ACACACACCTCCTAAACCCA | 577049 | 0 | 272 |
| n/a | 1291 | AAACAAAAACACACACCTCC | 577050 | 5 | 273 |

TABLE 9-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 1299 | GGTGGGAAAAACAAAAACAC | 577051 | 1 | 274 |
| n/a | 1326 | CTGTGAGAGCAAGTAGTGGG | 577052 | 3 | 275 |
| n/a | 1334 | AGCGAGTACTGTGAGAGCAA | 577053 | 0 | 276 |
| n/a | 1342 | TCACCCTCAGCGAGTACTGT | 577054 | 0 | 277 |
| n/a | 1358 | TCAGGTCTTTTCTTGTTCAC | 577055 | 0 | 278 |
| n/a | 1366 | AATCTTTATCAGGTCTTTTC | 577056 | 16 | 279 |
| n/a | 1374 | TTCTGGTTAATCTTTATCAG | 577057 | 22 | 280 |
| n/a | 1382 | TTGTTTTCTTCTGGTTAATC | 577058 | 19 | 281 |
| n/a | 1390 | TTCCCTCCTTGTTTTCTTCT | 577059 | 28 | 282 |
| n/a | 1398 | GCGGTTGTTTCCCTCCTTGT | 577060 | 17 | 283 |
| n/a | 1406 | TACAGGCTGCGGTTGTTTCC | 577061 | 28 | 284 |
| n/a | 1414 | GAGCTTGCTACAGGCTGCGG | 577062 | 23 | 285 |
| n/a | 1422 | GAGTTCCAGAGCTTGCTACA | 577063 | 14 | 286 |
| n/a | 1430 | CGACTCCTGAGTTCCAGAGC | 577064 | 0 | 287 |
| n/a | 1446 | CCCGGCCCCTAGCGCGCGAC | 577065 | 0 | 288 |
| n/a | 1454 | GCCCCGGCCCCGGCCCCTAG | 577066 | 0 | 289 |
| n/a | 1465 | ACCACGCCCCGGCCCCGGCC | 577067 | 0 | 290 |
| n/a | 1473 | CCGCCCCGACCACGCCCCGG | 577068 | 0 | 291 |
| n/a | 1481 | CCCCGGGCCCGCCCCGACCA | 577069 | 0 | 292 |
| n/a | 1495 | CGCCCCGGGCCCGCCCCCGG | 577070 | 0 | 293 |
| n/a | 1503 | CGCAGCCCCGCCCCGGGCCC | 577071 | 0 | 294 |
| n/a | 1511 | ACCGCAACCGCAGCCCCGCC | 577072 | 0 | 295 |
| n/a | 1519 | GCGCAGGCACCGCAACCGCA | 577073 | 18 | 296 |
| n/a | 1520 | GGCGCAGGCACCGCAACCGC | 577074 | 17 | 297 |
| n/a | 1536 | CGCCTCCGCCGCCGCGGGCG | 577075 | 32 | 298 |
| n/a | 1544 | ACCGCCTGCGCCTCCGCCGC | 577076 | 43 | 299 |
| n/a | 1552 | CACTCGCCACCGCCTGCGCC | 577077 | 52 | 300 |
| n/a | 1553 | CCACTCGCCACCGCCTGCGC | 577078 | 52 | 301 |
| n/a | 1853 | GGTCCCCGGGAAGGAGACAG | 577079 | 41 | 302 |
| n/a | 2453 | AACAACTGGTGCATGGCAAC | 577080 | 42 | 303 |
| n/a | 2753 | GTTTCAGATGTACTATCAGC | 577081 | 63 | 304 |
| n/a | 3053 | AAGGTGAAGTTCATATCACT | 577082 | 10 | 305 |
| n/a | 3452 | GGTAACTTCAAACTCTTGGG | 577083 | 70 | 306 |
| n/a | 3752 | GGTTCATGAGAGGTTTCCCA | 577084 | 53 | 307 |
| n/a | 4052 | TACTGAATTGCTTAGTTTTA | 577085 | 25 | 308 |
| n/a | 4425 | CTAACAGAATAAGAAAAAAA | 577086 | 0 | 309 |
| n/a | 5025 | GAGCATTAGATGAGTGCTTT | 577087 | 52 | 310 |

TABLE 9-continued

| Target Start Site at SEQ ID NO: 1 | Target Start Site at SEQ ID NO: 2 | Sequence | ISIS No | % inhibition | SEQ ID NO |
|---|---|---|---|---|---|
| n/a | 5325 | TGCATTCCTAAGCAATGTGT | 577088 | 28 | 311 |
| n/a | 5661 | TCTAGGCCTTCACATTAATT | 577089 | 37 | 312 |
| n/a | 5961 | CCTGTCTATGCCTAGGTGAA | 577090 | 19 | 313 |
| n/a | 6261 | TAGCACATACAATTATTACA | 577091 | 38 | 314 |
| n/a | 6566 | GAGGAGAAGAACATAAACGC | 577092 | 20 | 315 |
| n/a | 6866 | TACCACAAGTCTGGAGCCAT | 577093 | 27 | 316 |
| n/a | 7166 | GATACTGGATTGTTGAAACT | 577094 | 1 | 317 |
| n/a | 7466 | TAGTATGACTGGAGATTTGG | 577095 | 1 | 318 |
| n/a | 7766 | ATCAAAACCCCAAATGATTT | 577096 | 13 | 319 |
| 160 | 7840 | ATCCAAATGCTCCGGAGATA | 577097 | 78 | 320 |
| 190 | 7870 | TCGACATCACTGCATTCCAA | 577098 | 95 | 321 |
| 220 | 7900 | CAACAGCTGGAGATGGCGGT | 577099 | 56 | 322 |
| 250 | 7930 | ATTTGCCACTTAAAGCAATC | 577100 | 62 | 323 |
| 340 | 8020 | GTACCTGTTCTGTCTTTGGA | 577101 | 76 | 324 |
| 370 | 8050 | CAAGAAAAGTTATTTCTCCA | 577102 | 65 | 325 |
| 400 | 8080 | GAAGGATTTCTCCATTTAGA | 577103 | 50 | 326 |
| 430 | 8110 | TTACATCTATAGCACCACTC | 577104 | 73 | 327 |
| 460 | 8140 | TCACTCCCTTTTCAGACAAG | 577105 | 73 | 328 |
| 490 | 8170 | AGTTTCCATCAAAGATTAAT | 577106 | 55 | 329 |
| 520 | 8200 | ATAGTCCATATGTGCTGCGA | 577107 | 57 | 330 |
| 550 | 8230 | AACTAAGTTCTGTCTGTGGA | 577108 | 71 | 331 |
| 580 | 8260 | CAACACACACTCTATGAAGT | 577109 | 54 | 332 |
| 610 | 8290 | TTCCTTTCCGGATTATATGT | 577110 | 0 | 333 |

TABLE 10

| Target SEQ ID NO | Target Start Site | ISIS No | Sequence | % inhibition | SEQ ID NO |
|---|---|---|---|---|---|
| 3 | 751 | 576885 | TTTCCATTACAGGAATCACT | 63 | 334 |
| 3 | 807 | 576886 | ATCAGCCTATATCTATTTCC | 15 | 335 |
| 3 | 855 | 576887 | TCAATGACCAGGCGGTCCCC | 0 | 336 |
| 3 | 905 | 576888 | CTTTTTATGGAAAAGGAAAA | 0 | 337 |
| 3 | 984 | 576889 | TGTTTCCCCAAAAATTTCTG | 0 | 338 |
| 4 | 50 | 576890 | AGATATCCACTCGCCACCGC | 42 | 339 |

Example 2: Dose-Dependent Antisense Inhibition of Human C9ORF72 in HepG2 Cells Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 82.3 nM, 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3750 was used to measure mRNA levels. C9ORF72 mRNA levels were adjusted according to total RNA content, as measured by RIBOGREEN®. Results are presented as percent inhibition of C9ORF72, relative to untreated control cells.

The half maximal inhibitory concentration ($IC_{50}$) of each oligonucleotide is also presented in Tables 11-13. As illustrated, C9ORF72 mRNA levels were reduced in a dose-dependent manner in the antisense oligonucleotide treated cells.

TABLE 11

| ISIS No | 82.3 nM | 246.9 nM | 740.7 nM | 2222.2 nM | 6666.7 nM | 20000.0 nM | $IC_{50}$ (μM) |
|---|---|---|---|---|---|---|---|
| 576816 | 5 | 23 | 49 | 76 | 91 | 96 | 0.9 |
| 576817 | 8 | 2 | 6 | 29 | 58 | 83 | 4.7 |
| 576818 | 0 | 22 | 31 | 68 | 87 | 90 | 1.4 |
| 576819 | 0 | 12 | 44 | 72 | 81 | 86 | 1.4 |
| 576820 | 18 | 24 | 52 | 78 | 91 | 93 | 0.7 |
| 576841 | 23 | 19 | 29 | 52 | 75 | 85 | 1.6 |
| 576842 | 6 | 12 | 13 | 37 | 53 | 83 | 4.1 |
| 576860 | 9 | 24 | 54 | 70 | 83 | 87 | 1.0 |
| 576878 | 1 | 9 | 26 | 61 | 77 | 83 | 2.0 |
| 576931 | 16 | 21 | 24 | 49 | 77 | 83 | 1.8 |
| 576942 | 6 | 16 | 26 | 57 | 78 | 85 | 1.8 |

TABLE 12

| ISIS No | 82.3 nM | 246.9 nM | 740.7 nM | 2222.2 nM | 6666.7 nM | 20000.0 nM | $IC_{50}$ (μM) |
|---|---|---|---|---|---|---|---|
| 576894 | 9 | 30 | 38 | 61 | 75 | 84 | 1.3 |
| 576896 | 17 | 17 | 28 | 47 | 66 | 76 | 2.5 |
| 576927 | 3 | 26 | 40 | 60 | 79 | 81 | 1.5 |
| 576943 | 37 | 37 | 55 | 77 | 84 | 82 | 0.4 |
| 576945 | 20 | 41 | 56 | 73 | 83 | 84 | 0.6 |
| 576946 | 8 | 28 | 46 | 69 | 81 | 88 | 1.0 |
| 576963 | 0 | 0 | 25 | 51 | 63 | 83 | 2.9 |
| 576964 | 11 | 18 | 37 | 58 | 73 | 77 | 1.8 |
| 576967 | 19 | 31 | 48 | 68 | 77 | 85 | 0.9 |
| 577028 | 6 | 19 | 25 | 59 | 79 | 88 | 1.6 |
| 577029 | 7 | 22 | 44 | 67 | 77 | 85 | 1.3 |

TABLE 13

| ISIS No | 82.3 nM | 246.9 nM | 740.7 nM | 2222.2 nM | 6666.7 nM | 20000.0 nM | $IC_{50}$ (μM) |
|---|---|---|---|---|---|---|---|
| 576960 | 0 | 12 | 28 | 49 | 58 | 78 | 3.2 |
| 576974 | 25 | 45 | 65 | 70 | 65 | 78 | 0.5 |
| 576816 | 18 | 36 | 53 | 82 | 91 | 95 | 0.6 |
| 577097 | 22 | 20 | 31 | 63 | 82 | 94 | 1.1 |
| 577101 | 16 | 23 | 39 | 62 | 80 | 89 | 1.2 |
| 577105 | 0 | 4 | 30 | 48 | 78 | 92 | 2.0 |
| 577104 | 4 | 1 | 16 | 56 | 80 | 92 | 2.0 |
| 577108 | 0 | 0 | 24 | 52 | 76 | 83 | 2.9 |
| 577083 | 0 | 0 | 24 | 50 | 73 | 74 | 3.0 |
| 577078 | 0 | 0 | 10 | 15 | 30 | 75 | 10.8 |
| 577077 | 0 | 0 | 22 | 22 | 51 | 83 | 5.0 |

Example 3: Dose-Dependent Antisense Inhibition of Human C9ORF72 in HepG2 Cells Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 total mRNA levels, as well as mRNA levels of the exon 1 transcript, were measured by quantitative real-time PCR. Human C9ORF72 primer probe set RTS3750 was used to measure total C9ORF72 mRNA levels. Primer probe set RTS3905 (forward sequence GGGTCTAGCAAGAGCAGGTG, designated herein as SEQ ID NO: 18; reverse sequence GTCTTGGCAACAGCTGGAGAT, designated herein as SEQ ID NO: 19; probe sequence TGATGTCGACTCTTTGCCCACCGC, designated herein as SEQ ID NO: 20) was used to measure exon 1 message transcript. C9ORF72 mRNA levels were adjusted according to total RNA content, as measured by RIBOGREEN®. Results are presented as percent inhibition of C9ORF72, relative to untreated control cells.

The half maximal inhibitory concentration ($IC_{50}$) of each oligonucleotide is also presented in Tables 14 and 15. As illustrated, C9ORF72 mRNA levels were reduced in a dose-dependent manner in the antisense oligonucleotide treated cells. 'n.d.' indicates that there is no data for that particular dose.

TABLE 14

| % inhibition of total C9ORF72 mRNA levels | | | | | | |
|---|---|---|---|---|---|---|
| ISIS No | 246.9 nM | 740.7 nM | 2222.2 nM | 6666.7 nM | 20000.0 nM | $IC_{50}$ (μM) |
| 576816 | 29 | 53 | 84 | 90 | 92 | 0.60 |
| 576820 | 20 | 42 | 70 | 87 | 75 | 1.19 |
| 576860 | 25 | 53 | 72 | 86 | 85 | 0.80 |
| 576974 | 36 | 49 | 64 | 65 | 68 | 0.95 |
| 577041 | 3 | 0 | 0 | 0 | 0 | >20.00 |
| 577042 | 0 | 2 | 0 | 3 | 0 | >20.00 |
| 577061 | 0 | 3 | 0 | 4 | 0 | >20.00 |
| 577065 | 7 | 0 | 1 | 6 | 0 | >20.00 |
| 577069 | 3 | 0 | 3 | 0 | 0 | >20.00 |
| 577073 | 7 | 0 | 8 | 11 | 0 | >20.00 |
| 577074 | 0 | 7 | 11 | 15 | 0 | >20.00 |
| 577078 | 0 | 2 | 20 | 65 | 81 | 5.22 |
| 577083 | 0 | 19 | 55 | 71 | 75 | 3.35 |
| 577088 | 6 | 11 | 49 | 61 | 74 | 3.93 |
| 577097 | 3 | 38 | 62 | 78 | 82 | 1.94 |

TABLE 15

| % inhibition of C9ORF72 exon 1 mRNA levels | | | | | | |
|---|---|---|---|---|---|---|
| ISIS No | 246.9 nM | 740.7 nM | 2222.2 nM | 6666.7 nM | 20000.0 nM | $IC_{50}$ (μM) |
| 576794 | 42 | 67 | n.d. | 93 | 87 | 0.27 |
| 576816 | 45 | 78 | 93 | n.d. | n.d. | 0.26 |
| 576820 | 54 | 65 | 92 | 98 | 94 | <0.247 |
| 576860 | 43 | 36 | 71 | 95 | 91 | 0.66 |
| 577041 | 0 | 0 | 49 | 4 | 31 | >20.00 |
| 577042 | 9 | 15 | 0 | 33 | 12 | >20.00 |
| 577061 | 8 | 36 | 70 | 67 | 76 | 2.03 |
| 577065 | 20 | 55 | 67 | 82 | 62 | 1.06 |
| 577069 | 22 | 24 | 61 | 74 | 70 | 2.16 |
| 577073 | 4 | 62 | 69 | 82 | 81 | 1.21 |
| 577074 | 8 | 49 | 69 | 85 | 85 | 1.29 |

TABLE 15-continued

| | % inhibition of C9ORF72 exon 1 mRNA levels | | | | | |
|---|---|---|---|---|---|---|
| ISIS No | 246.9 nM | 740.7 nM | 2222.2 nM | 6666.7 nM | 20000.0 nM | $IC_{50}$ (μM) |
| 577078 | 0 | 21 | 59 | 81 | n.d. | 1.90 |
| 577083 | 30 | 43 | 85 | 88 | 92 | 0.71 |
| 577088 | 38 | 44 | 79 | 87 | 91 | 0.61 |
| 577097 | 17 | 47 | 52 | 94 | 89 | 1.27 |

Example 4: Antisense Inhibition of Human C9ORF72 in HepG2 Cells

Antisense oligonucleotides were designed targeting the hexanucleotide repeat expansion of a C9ORF72 nucleic acid and were tested for their effects on C9ORF72 mRNA in vitro. The antisense oligonucleotides were tested in a series of experiments that had similar culture conditions. The results for each experiment are presented in separate tables shown below. ISIS 576816 and ISIS 577065 were included in these assays for comparison. Cultured C9ORF72 fibroblasts at a density of 35,000 cells per well were transfected using electroporation with 7,000 nM antisense oligonucleotide. After a treatment period of approximately 24 hours, RNA was isolated from the cells and C9ORF72 mRNA levels were measured by quantitative real-time PCR. Human primer probe sets RTS3750, RTS 3905, or RTS4097 (forward sequence CAAGCCACCGTCTCACTCAA, designated herein as SEQ ID NO: 24: reverse sequence GTAGTGCTGTCTACTCCAGAGAGTTACC, designated herein as SEQ ID NO: 25; probe sequence CTTGGCTTCCCTCAAAAGACTGGCTAATGT, designated herein as SEQ ID NO: 26) were used to measure mRNA levels. RTS3750 targets exon 2 of the mRNA transcripts and, therefore, measures total mRNA transcripts. RTS3905 targets the hexanucleotide repeat expansion containing transcript and, therefore, measures only mRNA transcripts that contain the hexanucleotide repeat expansion. RTS4097 targets the gene sequence at a site 3' of the hexanucleotide repeat expansion. mRNA levels were adjusted according to total RNA content, as measured by RIBOGREEN®. Results are presented as percent inhibition of C9ORF72, relative to untreated control cells. 'n.d.' indicates that there is no data for that particular antisense oligonucleotide.

The antisense oligonucleotides in Table 16 were designed as uniform MOE oligonucleotides, or 3-10-3 MOE, 4-10-3 MOE, 4-10-4 MOE, 5-10-4 MOE, or 5-10-5 MOE gapmers. The uniform MOE oligonucleotides are 20 nucleosides in length, wherein each nucleoside comprises a 2'-MOE group. The 3-10-3 MOE gapmers are 16 nucleosides in length, wherein the central gap segment comprises ten 2'-deoxynucleosides and is flanked by wing segments on both the 5' end and on the 3' end comprising three nucleosides each. The 4-10-3 gapmers are 17 nucleosides in length, wherein the central gap segment comprises ten 2'-deoxynucleosides and is flanked by wing segments on both the 5' end and on the 3' end comprising four and three nucleosides, respectively. The 4-10-4 gapmers are 18 nucleosides in length, wherein the central gap segment comprises ten 2'-deoxynucleosides and is flanked by wing segments on both the 5' end and on the 3' end comprising four nucleosides each. The 5-10-4 gapmers are 19 nucleosides in length, wherein the central gap segment comprises ten 2'-deoxynucleosides and is flanked by wing segments on both the 5' end and on the 3' end comprising five and four nucleosides, respectively. The 5-10-5 gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment comprises a 2'-MOE group. The internucleoside linkages throughout each oligonucleotide are phosphorothioate linkages. All cytosine residues throughout each oligonucleotide are 5-methylcytosines. "Start site" indicates the 5'-most nucleoside to which the antisense oligonucleotide is targeted in the human gene sequence. "Stop site" indicates the 3'-most nucleoside to which the antisense oligonucleotide is targeted human gene sequence. Each antisense oligonucleotide listed in Table 16 is targeted to the human C9ORF72 genomic sequence, designated herein as SEQ ID NO: 2 (the complement of GENBANK Accession No. NT_008413.18 truncated from nucleosides 27535000 to 27565000) or SEQ ID NO: 13, which is an expanded version of the hexanucleotide repeat from intron 1 of the C9ORF72 gene.

The data indicates that certain antisense oligonucleotides preferentially inhibit levels of C9ORF72 mRNA transcript levels that contain the hexanucleotide repeat.

TABLE 16

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1457 | 1<br>7<br>13 | Uniform MOE | CCGGCCCCGGCCCCGGCCCC | 573674 | 0 | 34 | 0 | 340 |
| 1458 | 2<br>8<br>14 | Uniform MOE | CCCGGCCCCGGCCCCGGCCC | 573675 | 0 | 28 | 0 | 341 |
| 1459 | 3<br>9<br>15 | Uniform MOE | CCCCGGCCCCGGCCCCGGCC | 573676 | 0 | 34 | 0 | 342 |
| 1460 | 4<br>10<br>16 | Uniform MOE | GCCCCGGCCCCGGCCCCGGC | 573677 | 4 | 41 | 0 | 343 |

TABLE 16-continued

| Target Start Site on SEQ ID NO: 2 | Target Start Site on SEQ ID NO: 13 | Motif | Sequence | ISIS NO | % inhi-bition (RTS3750) | % inhi-bition (RTS3905) | % inhi-bition (RTS4097) | SEQ ID NO |
|---|---|---|---|---|---|---|---|---|
| n/a | 5<br>11<br>17 | Uniform MOE | GGCCCCGGCCCCG GCCCCGG | 573678 | 12 | 11 | 6 | 344 |
| n/a | 6<br>12 | Uniform MOE | CGGCCCCGGCCCC GGCCCCG | 573679 | 0 | 0 | 0 | 345 |
| 1457 | 1<br>7<br>13 | Uniform MOE | CGGCCCCGGCCCC GGCCCC | 573680 | 10 | 6 | 0 | 346 |
| 1458 | 2<br>8<br>14 | Uniform MOE | CCGGCCCCGGCCC CGGCCC | 573681 | 13 | 23 | 0 | 347 |
| 1459 | 3<br>9<br>15 | Uniform MOE | CCCGGCCCCGGCC CCGGCC | 573682 | 2 | 48 | 0 | 348 |
| 1460 | 4<br>10<br>16 | Uniform MOE | CCCCGGCCCCGGC CCCGGC | 573683 | 0 | 38 | 0 | 349 |
| 1461 | 5<br>11<br>17 | Uniform MOE | GCCCCGGCCCCGG CCCCGG | 573684 | 0 | 0 | 0 | 350 |
| n/a | 6<br>12<br>18 | Uniform MOE | GGCCCCGGCCCCG GCCCCG | 573685 | 0 | 27 | 0 | 351 |
| 1457 | 1<br>7<br>13<br>19 | Uniform MOE | GGCCCCGGCCCCG GCCCC | 573686 | 0 | 40 | 0 | 352 |
| 1458 | 2<br>8<br>14 | Uniform MOE | CGGCCCCGGCCCC GGCCC | 573687 | 0 | 0 | 0 | 353 |
| 1459 | 3<br>9<br>15 | Uniform MOE | CCGGCCCCGGCCC CGGCC | 573688 | 22 | 0 | 0 | 354 |
| 1460 | 4<br>10<br>16 | Uniform MOE | CCCGGCCCCGGCC CCGGC | 573689 | 0 | 22 | 0 | 355 |
| 1461 | 5<br>11<br>17 | Uniform MOE | CCCCGGCCCCGGC CCCGG | 573690 | 15 | 43 | 0 | 356 |
| 1462 | 6<br>12<br>18 | Uniform MOE | GCCCCGGCCCCGG CCCCG | 573691 | 10 | 16 | 0 | 357 |
| 1457<br><br>1463 | 1<br>7<br>13<br>19 | Uniform MOE | GCCCCGGCCCCGG CCCC | 573692 | 6 | 65 | 0 | 358 |
| 1458 | 2<br>8<br>14<br>20 | Uniform MOE | GGCCCCGGCCCCG GCCC | 573693 | 9 | 0 | 0 | 359 |
| 1459 | 3<br>9<br>15 | Uniform MOE | CGGCCCCGGCCCC GGCC | 573694 | 10 | 0 | 0 | 360 |
| 1460 | 4<br>10<br>16 | Uniform MOE | CCGGCCCCGGCCC CGGC | 573695 | 3 | 42 | 0 | 361 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1461 | 5<br>11<br>17 | Uniform MOE | CCCGGCCCCGGCCCCGG | 573696 | 0 | 23 | 0 | 362 |
| 1462 | 6<br>12<br>18 | Uniform MOE | CCCCGGCCCCGGCCCCG | 573697 | 0 | 28 | 0 | 363 |
| 1457<br>1463 | 1<br>7<br>13<br>19 | Uniform MOE | CCCCGGCCCCGGCCCC | 573698 | 1 | 68 | 0 | 364 |
| 1458<br>1464 | 2<br>8<br>14<br>20 | Uniform MOE | GCCCCGGCCCCGGCCC | 573699 | 0 | 31 | 0 | 365 |
| 1459 | 3<br>9<br>15<br>21 | Uniform MOE | GGCCCCGGCCCCGGCC | 573700 | 7 | 2 | 2 | 366 |
| 1460 | 4<br>10<br>16 | Uniform MOE | CGGCCCCGGCCCCGGC | 573701 | 15 | 1 | 8 | 367 |
| 1461 | 5<br>11<br>17 | Uniform MOE | CCGGCCCCGGCCCCGG | 573702 | 26 | 0 | 0 | 368 |
| 1462 | 6<br>12<br>18 | Uniform MOE | CCCGGCCCCGGCCCCG | 573703 | 12 | 52 | 10 | 369 |
| 1457 | 1<br>7<br>13 | 5-10-5 MOE | CCGGCCCCGGCCCCGGCCCC | 573716 | 0 | 93 | 46 | 340 |
| 1458 | 2<br>8<br>14 | 5-10-5 MOE | CCCGGCCCCGGCCCCGGCCC | 573717 | 0 | 98 | 0 | 341 |
| 1459 | 3<br>9<br>15 | 5-10-5 MOE | CCCCGGCCCCGGCCCCGGCC | 573718 | 0 | 98 | 2 | 342 |
| 1460 | 4<br>10<br>16 | 5-10-5 MOE | GCCCCGGCCCCGGCCCCGGC | 573719 | 0 | 68 | 19 | 343 |
| n/a | 5<br>11<br>17 | 5-10-5 MOE | GGCCCCGGCCCCGGCCCCGG | 573720 | 13 | 90 | 18 | 344 |
| n/a | 6<br>12 | 5-10-5 MOE | CGGCCCCGGCCCCGGCCCCG | 573721 | 0 | 98 | 18 | 345 |
| 1457 | 1<br>7<br>13 | 5-10-4 MOE | CGGCCCCGGCCCCGGCCCC | 573722 | 0 | 97 | 0 | 346 |
| 1458 | 2<br>8<br>14 | 5-10-4 MOE | CCGGCCCCGGCCCCGGCCC | 573723 | 0 | n.d. | 8 | 347 |
| 1459 | 3<br>9<br>15 | 5-10-4 MOE | CCCGGCCCCGGCCCCGGCC | 573724 | 0 | 94 | 28 | 348 |
| 1460 | 4<br>10<br>16 | 5-10-4 MOE | CCCCGGCCCCGGCCCCGGC | 573725 | 0 | 94 | 7 | 349 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1461 | 5<br>11<br>17 | 5-10-4 MOE | GCCCCGGCCCCGGCCCCGG | 573726 | 0 | n.d. | 28 | 350 |
| n/a | 6<br>12<br>18 | 5-10-4 MOE | GGCCCCGGCCCCGGCCCCG | 573727 | 0 | 98 | 40 | 351 |
| 1457 | 1<br>7<br>13<br>19 | 4-10-4 MOE | GGCCCCGGCCCCGGCCCC | 573728 | 0 | 97 | 19 | 352 |
| 1458 | 2<br>8<br>14 | 4-10-4 MOE | CGGCCCCGGCCCCGGCCC | 573729 | 0 | n.d. | 36 | 353 |
| 1459 | 3<br>9<br>15 | 4-10-4 MOE | CCGGCCCCGGCCCCGGCC | 573730 | 0 | 94 | 24 | 354 |
| 1460 | 4<br>10<br>16 | 4-10-4 MOE | CCCGGCCCCGGCCCCGGC | 573731 | 0 | 97 | 13 | 355 |
| 1461 | 5<br>11<br>17 | 4-10-4 MOE | CCCCGGCCCCGGCCCCGG | 573732 | 0 | 97 | 1 | 356 |
| 1462 | 6<br>12<br>18 | 4-10-4 MOE | GCCCCGGCCCCGGCCCCG | 573733 | 0 | n.d. | 0 | 357 |
| 1457<br><br>1463 | 1<br>7<br>13<br>19 | 4-10-3 MOE | GCCCCGGCCCCGGCCCC | 573734 | 0 | 96 | 0 | 358 |
| 1458 | 2<br>8<br>14<br>20 | 4-10-3 MOE | GGCCCCGGCCCCGGCCC | 573735 | 0 | 94 | 21 | 359 |
| 1459 | 3<br>9<br>15 | 4-10-3 MOE | CGGCCCCGGCCCCGGCC | 573736 | 0 | 93 | 43 | 360 |
| 1460 | 4<br>10<br>16 | 4-10-3 MOE | CCGGCCCCGGCCCCGGC | 573737 | 0 | 96 | 19 | 361 |
| 1461 | 5<br>11<br>17 | 4-10-3 MOE | CCCGGCCCCGGCCCCGG | 573738 | 0 | n.d. | 24 | 362 |
| 1462 | 6<br>12<br>18 | 4-10-3 MOE | CCCCGGCCCCGGCCCCG | 573739 | 0 | n.d. | 34 | 363 |
| 1457<br><br>1463 | 1<br>7<br>13<br>19 | 3-10-3 MOE | CCCCGGCCCCGGCCCC | 573740 | 0 | n.d. | 4 | 364 |
| 1458<br><br>1464 | 2<br>8<br>14<br>20 | 3-10-3 MOE | GCCCCGGCCCCGGCCC | 573741 | 0 | 95 | 6 | 365 |
| 1459 | 3<br>9<br>15<br>21 | 3-10-3 MOE | GGCCCCGGCCCCGGCC | 573742 | 23 | 97 | 49 | 366 |

TABLE 16-continued

| Target Start Site on SEQ ID NO: 2 | Target Start Site on SEQ ID NO: 13 | Motif | Sequence | ISIS NO | % inhibition (RTS3750) | % inhibition (RTS3905) | % inhibition (RTS4097) | SEQ ID NO |
|---|---|---|---|---|---|---|---|---|
| 1460 | 4<br>10<br>16 | 3-10-3 MOE | CGGCCCCGGCCCCGGC | 573743 | 0 | 96 | 0 | 367 |
| 1461 | 5<br>11<br>17 | 3-10-3 MOE | CCGGCCCCGGCCCCGG | 573744 | 0 | 94 | 34 | 368 |
| 1462 | 6<br>12<br>18 | 3-10-3 MOE | CCCGGCCCCGGCCCCG | 573745 | 0 | 94 | 34 | 368 |
| 7990 | n/a | 5-10-5 MOE | GCCTTACTCTAGGACCAAGA | 576816 | 83 | 91 | 29 | 40 |
| 1446 | n/a | 5-10-5 MOE | CCCGGCCCCTAGCGCGCGAC | 577065 | 0 | 87 | 34 | 288 |

Example 5: In Vivo Rodent Inhibition and Tolerability with Treatment of C9ORF72 Antisense Oligonucleotides In order to assess the tolerability of inhibition of C9ORF72 expression in vivo, antisense oligonucleotides targeting a murine C9ORF72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 11 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A: wherein 's' denotes a phosphorothioate internucleoside linkage, 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 12 (GENBANK Accession No. NM_001007702.1).

Mouse Experiment 1

Groups of 4 C57BL/6 mice each were injected with 50 μg, 100 μg, 300 μg, 500 μg, or 700 μg of ISIS 571883 administered via an intracerebroventricular bolus injection. A control group of four C57/BL6 mice were similarly treated with PBS. Animals were anesthetized with 3% isofluorane and placed in a stereotactic frame. After sterilizing the surgical site, each mouse was injected −0.2 mm anterio-posterior from the bregma na d 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9ORF72 mRNA expression. C9ORF72 mRNA expression was measured by RT-PCR. The data is presented in Table 17. The results indicate that treatment with increasing doses of ISIS 571883 resulted in dose-dependent inhibition of C9ORF72 mRNA expression.

The induction of the microglial marker AIF-1 as a measure of CNS toxicity was also assessed. The data is presented in Table 18. The results indicate that treatment with increasing doses of ISIS 571883 did not result in significant increases in AIF-1 mRNA expression. Hence, the injection of ISIS 571883 was deemed tolerable in this model.

TABLE 17

Percentage inhibition of C9ORF72 mRNA expression compared to the PBS control

| Dose (μg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 18

| Percentage expression of AIF-1 mRNA expression compared to the PBS control | | |
|---|---|---|
| Dose (µg) | Posterior brain | Spinal cord |
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 µg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 19 and 20. The results indicate that there were no significant changes in the motor behavior of the mice as a result of antisense inhibition of ISIS 571883 or due to the ICV injection. Hence, antisense inhibition of C9ORF72 was deemed tolerable in this model.

TABLE 19

| Latency to fall (sec) in the rotarod assay | | |
|---|---|---|
| Weeks after injection | PBS | ISIS 571883 |
| 0 | 66 | 66 |
| 4 | 91 | 70 |
| 8 | 94 | 84 |

TABLE 20

| Mean hindlimb grip strength (g) in the grip strength assay | | |
|---|---|---|
| Weeks after injection | PBS | ISIS 571883 |
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 µg, 1,000 µg, or 3,000 µg of ISIS 603538 administered via an intrathecal bolus injection. A control group of four Sprague-Dawley rats were similarly treated with PBS. Animals were anesthetized with 3% isofluorane and placed in a stereotactic frame. After sterilizing the surgical site, each rat was injected with 30 µL of ASO solution administered via 8 cm intrathecal catheter 2 cm into the spinal canal with a 50 µL flush. The rats were allowed to recover for 4 weeks, after which animals were euthanized according to a humane protocol approved by the Institutional Animal Care and Use Committee.

RNA Analysis

RNA was extracted from a 2-3 mm brain section posterior to the injection site, from brain frontal cortex, and from the cervical and lumbar sections of the spinal cord tissue for analysis of C9ORF72 mRNA expression. C9ORF72 mRNA expression was measured by RT-PCR. The data is presented in Table 21. The results indicate that treatment with increasing doses of ISIS 603538 resulted in dose-dependent inhibition of C9ORF72 mRNA expression.

The induction of the microglial marker AIF-1 as a measure of CNS toxicity was also assessed. The data is presented in Table 22. The results indicate that treatment with increasing doses of ISIS 603538 did not result in significant increases in AIF-1 mRNA expression. Hence, the injection of ISIS 603538 was deemed tolerable in this model.

TABLE 21

| Percentage inhibition of C9ORF72 mRNA expression compared to the PBS control | | | | |
|---|---|---|---|---|
| Dose (µg) | Brain (1 mm section) | Cortex | Spinal cord (lumbar) | Spinal cord (cervical) |
| 700 | 21 | 4 | 86 | 74 |
| 1000 | 53 | 49 | 88 | 82 |
| 3000 | 64 | 62 | 88 | 80 |

TABLE 22

| Percentage expression of AIF-1 mRNA expression compared to the PBS control | | | | |
|---|---|---|---|---|
| Dose (µg) | Brain (1 mm section) | Cortex | Spinal cord (lumbar) | Spinal cord (cervical) |
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 23. The results indicate that treatment with increasing doses of ISIS 603538 did not have any significant changes in the body weights of the rats.

TABLE 23

| Body weights of the rats (% initial body weight) | | | | | | |
|---|---|---|---|---|---|---|
| | Dose (µg) | Week 1 | Week 2 | Week 3 | Week 4 | Week 5 |
| PBS | | 100 | 94 | 103 | 105 | 109 |
| ISIS | 700 | 100 | 94 | 98 | 103 | 107 |
| 603538 | 1000 | 100 | 95 | 97 | 101 | 103 |
| | 3000 | 100 | 92 | 98 | 102 | 105 |

Example 6: Preferential Inhibition of Human C9ORF72 Expression in Two Patient Fibroblast Lines Two different fibroblast cell lines from human patients (F09-152 and F09-229) were analyzed with antisense oligonucleotides that target the C9ORF72 pre-mRNA sequence before exon 1B; i.e. antisense oligonucleotides that target the hexanucleotide repeat expansion containing transcript and antisense oligonucleotides that target downstream of exon 1. The target start and stop sites and the target regions with respect to SEQ ID NOs: 1 and 2 for each oligonucleotide are provided in Table 24. ISIS 577061 and ISIS 577065 target C9ORF72 upstream of exon 1B and just upstream of the hexanucleotide repeat. The rest of the ISIS oligonucleotides of Table 24 target C9ORF72 downstream of exon 1B and the hexanucleotide repeat.

TABLE 24

Target Start and Stop sites of ISIS oligonucleotides used in a dose response assay in C9ORF72 patient fibroblasts

| ISIS No | Target Start Site at SEQ ID NO: 1 | Target Start Site at SEQ ID NO: 2 | Target Region |
|---|---|---|---|
| 577061 | n/a | 1406 | Upstream of exon 1B |
| 577065 | n/a | 1446 | Upstream of exon 1B |
| 577083 | n/a | 3452 | Downstream of exon 1B |
| 576816 | 232 | 7990 | Exon 2 |
| 576974 | 3132 | 28251 | Exon 11 |

Cells were plated at a density of 20,000 cells per well and transfected using electroporation with 246.9 nM, 740.7 nM, 2,222.2 nM, 6,666.7 nM, and 20,000.0 nM concentrations of antisense oligonucleotide. After a treatment period of approximately 16 hours, RNA was isolated from the cells and C9ORF72 mRNA levels were measured by quantitative real-time PCR. Two primer probe sets were used: (1) human C9ORF72 primer probe set RTS3750, which measures total mRNA levels, and (2) RTS3905, which targets the hexanucleotide repeat expansion containing transcript, which measures only mRNA transcripts that contain the hexanucleotide repeat expansion. C9ORF72 mRNA levels were adjusted according to total RNA content, as measured by RIBOGREEN®. Results are presented as percent inhibition of C9ORF72, relative to untreated control cells.

As illustrated in Table 25, below, the two oligonucleotides that target upstream of exon 1B and, therefore, target mRNA transcripts containing the hexanucleotide repeat expansion (ISIS 577061 and ISIS 577065), do not inhibit total mRNA levels of C9ORF72 (as measured by RTS3750) as well as ISIS 576974, 576816, and 577083, which target downstream of exon 1B and, therefore, do not target the mRNA transcript containing the hexanucleotide repeat expansion. Expression levels of the C9ORF72 mRNA transcript containing the hexanucleotide repeat expansion are low (about 10% of the total C9ORF72 expression products), therefore, oligonucleotides targeting the mRNA transcript containing the hexanucleotide repeat expansion do not robustly inhibit total C9ORF72 mRNA (as measured by RTS3905), as suggested by Table 25 below. Thus. ISIS 577061 and ISIS 577065 preferentially inhibit expression of mRNA transcripts containing the hexanucleotide repeat expansion.

TABLE 25

Percent inhibition of C9ORF72 total mRNA in F09-152 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 6 | 11 | 0 | 18 | 10 |
| 577065 | 10 | 11 | 30 | 29 | 0 |
| 576974 | 61 | 69 | 72 | 83 | 83 |
| 576816 | 35 | 76 | 82 | 91 | 93 |
| 577083 | 28 | 38 | 52 | 75 | 80 |

TABLE 26

Percent inhibition of C9ORF72 mRNA transcripts containing the hexanucleotide repeat expansion in F09-152 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 4 | 28 | 58 | 81 | 87 |
| 577065 | 25 | 54 | 70 | 90 | 94 |
| 576974 | 57 | 77 | 81 | 93 | 92 |
| 576816 | 37 | 77 | 91 | 97 | 98 |
| 577083 | 37 | 53 | 74 | 93 | 94 |

TABLE 27

Percent inhibition of C9ORF72 total mRNA in F09-229 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 0 | 0 | 0 | 17 | 7 |
| 577065 | 8 | 17 | 17 | 16 | 3 |
| 576974 | 43 | 58 | 85 | 85 | 74 |
| 576816 | 45 | 70 | 85 | 81 | 89 |
| 577083 | 22 | 45 | 56 | 76 | 78 |

TABLE 28

Percent inhibition of C9ORF72 mRNA transcripts containing the hexanucleotide repeat expansion in F09-229 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 14 | 36 | 70 | 87 | 89 |
| 577065 | 26 | 48 | 92 | 91 | 98 |
| 576974 | 63 | 87 | 91 | 92 | 91 |
| 576816 | 62 | 81 | 96 | 98 | 100 |
| 577083 | 36 | 64 | 82 | 98 | 96 |

What is claimed is:

1. A compound comprising a modified oligonucleotide consisting of 12 to 50 linked nucleosides and comprising a nucleobase sequence comprising at least 8 contiguous nucleobases of SEQ ID NOs: 30-107, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned immediately adjacent to and between the 5' wing segment and the 3' wing segment and wherein each nucleoside of each wing segment comprises a modified sugar.

2. The compound of claim 1, wherein the nucleobase sequence of the modified oligonucleotide is at least 75% complementary to an equal length portion of a human C9ORF72 nucleic acid of any one of SEQ ID NOs: 1-10.

3. The compound of claim 1, wherein the modified oligonucleotide comprises at least one modified internucleoside linkage.

4. The compound of claim 3, wherein the modified internucleoside linkage is a phosphorothioate internucleoside linkage.

5. The compound of claim 1, wherein modified the modified sugar comprises a bicyclic sugar moiety or a non-bicyclic 2'-modified sugar moiety.

6. The compound of claim 5, wherein:

(a) the bicyclic sugar comprises a chemical bridge between the 4' and 2' positions of the sugar, wherein the chemical bridge is selected from: 4'-CH(R)—O-2' and 4'-(CH2)2-O-2', wherein R is independently H, C1-C6 alkyl, and C1-C6 alkoxy; or (b) the non-bicyclic 2'-modified sugar moiety comprises a 2'-O-methoxyethyl group or a 2'-O-methyl group.

7. A compound comprising a single-stranded antisense oligonucleotide consisting of 12 to 30 linked nucleosides and comprising a nucleobase sequence comprising at least 8 contiguous nucleobases of SEQ ID NOs: 180-257, wherein the single-stranded antisense oligonucleotide comprises:

a gap segment consisting of linked deoxynucleosides;

a 5' wing segment consisting of linked nucleosides; and a 3' wing segment consisting of linked nucleosides;

wherein the gap segment is positioned immediately adjacent to and between the 5' wing segment and the 3' wing segment and wherein each nucleoside of each wing segment comprises a modified sugar.

8. The compound of claim 7, wherein the nucleobase sequence of the single-stranded antisense oligonucleotide is at least 75% complementary to an equal length portion of a human C9ORF72 nucleic acid of any one of SEQ ID NOs: 1-10.

9. The compound of claim 7, wherein the single-stranded antisense oligonucleotide comprises at least one modified internucleoside linkage.

10. The compound of claim 9, wherein the modified internucleoside linkage is a phosphorothioate internucleoside linkage.

11. The compound of claim 7, wherein the modified sugar comprises a bicyclic sugar moiety or a non-bicyclic 2'-modified sugar moiety.

12. The compound of claim 11, wherein:

(a) the bicyclic sugar comprises a chemical bridge between the 4' and 2' positions of the sugar, wherein the chemical bridge is selected from: 4'-CH(R)—O-2' and 4'-(CH2)2-O-2', wherein R is independently H, C1-C6 alkyl, and C1-C6 alkoxy; or (b) the non-bicyclic 2'-modified sugar moiety comprises a 2'-O-methoxyethyl group or a 2'-O-methyl group.

13. The compound of claim 1, wherein the modified antisense oligonucleotide consists of 12 to 50 linked nucleosides and has a nucleobase sequence comprising a nucleobase sequence having at least 10 contiguous nucleobases of any one of SEQ ID NOs: 30-107.

14. The compound of claim 1, wherein the modified antisense oligonucleotide consists of 12 to 50 linked nucleosides and has a nucleobase sequence comprising a nucleobase sequence having at least 12 contiguous nucleobases of any one of SEQ ID NOs: 30-107.

15. The compound of claim 1, wherein the modified antisense oligonucleotide consists of 14 to 50 linked nucleosides and has a nucleobase sequence comprising a nucleobase sequence having at least 14 contiguous nucleobases of any one of SEQ ID NOs: 30-107.

16. The compound of claim 1, wherein the modified antisense oligonucleotide consists of 16 to 50 linked nucleosides and has a nucleobase sequence comprising a nucleobase sequence having at least 16 contiguous nucleobases of any one of SEQ ID NOs: 30-107.

17. The compound of claim 2, wherein the nucleobase sequence of the modified antisense oligonucleotide is at least 90% complementary to an equal length portion of a human C9ORF72 nucleic acid of any one of SEQ ID NOs: 1-10.

18. The compound of claim 2, wherein the nucleobase sequence of the modified antisense oligonucleotide is 100% complementary to an equal length portion of a human C9ORF72 nucleic acid of any one of SEQ ID NOs: 1-10.

19. The compound of claim 7, wherein the modified antisense oligonucleotide consists of 12 to 50 linked nucleosides and has a nucleobase sequence comprising a nucleobase sequence having at least 10 contiguous nucleobases of any one of SEQ ID NOs: 180-257.

20. The compound of claim 7, wherein the modified antisense oligonucleotide consists of 12 to 50 linked nucleosides and has a nucleobase sequence comprising a nucleobase sequence having at least 12 contiguous nucleobases of any one of SEQ ID NOs: 180-257.

21. The compound of claim 7, wherein the modified antisense oligonucleotide consists of 14 to 50 linked nucleosides and has a nucleobase sequence comprising a nucleobase sequence having at least 14 contiguous nucleobases of any one of SEQ ID NOs: 180-257.

22. The compound of claim 7, wherein the modified antisense oligonucleotide consists of 16 to 50 linked nucleosides and has a nucleobase sequence comprising a nucleobase sequence having at least 16 contiguous nucleobases of any one of SEQ ID NOs: 180-257.

23. The compound of claim 8, wherein the nucleobase sequence of the modified antisense oligonucleotide is at least 90% complementary to an equal length portion of a human C9ORF72 nucleic acid of any one of SEQ ID NOs: 1-10.

24. The compound of claim 8, wherein the nucleobase sequence of the modified antisense oligonucleotide is 100% complementary to an equal length portion of a human C9ORF72 nucleic acid of any one of SEQ ID NOs: 1-10.

* * * * *